US012636519B2

(12) United States Patent
Roberts et al.

(10) Patent No.: US 12,636,519 B2
(45) Date of Patent: May 26, 2026

(54) INTRA-OPERATIVE RADIATION THERAPY CAPSULE WITH CYLINDRICAL SHELL RADIATION CONTAINMENT SHUTTER SYSTEM

(71) Applicant: SRIORT, LLC, Baltimore, MD (US)

(72) Inventors: Walter A. Roberts, Jasper, IN (US); Brooke Schumm, III, Ellicott City, MD (US)

(73) Assignee: SRIORT, LLC, Ellicott City, MD (US)

( * ) Notice: Subject to any disclaimer, the term of this patent is extended or adjusted under 35 U.S.C. 154(b) by 210 days.

(21) Appl. No.: 16/494,476

(22) PCT Filed: Feb. 8, 2018

(86) PCT No.: PCT/US2018/017495

§ 371 (c)(1),
(2) Date: Sep. 16, 2019

(87) PCT Pub. No.: WO2018/148464

PCT Pub. Date: Aug. 16, 2018

(65) Prior Publication Data

US 2024/0238617 A1      Jul. 18, 2024

Related U.S. Application Data

(60) Provisional application No. 62/562,959, filed on Sep. 25, 2017, provisional application No. 62/456,151, filed on Feb. 8, 2017.

(51) Int. Cl.
*A61N 5/10*        (2006.01)
*A61B 34/35*       (2016.01)
(Continued)

(52) U.S. Cl.
CPC ............ *A61N 5/1007* (2013.01); *A61B 34/35* (2016.02); *A61B 90/361* (2016.02); *A61B 90/37* (2016.02);
(Continued)

(58) Field of Classification Search
CPC .. A61N 5/1007; A61N 5/1015; A61N 5/1048; A61N 2005/1052;
(Continued)

(56) References Cited

U.S. PATENT DOCUMENTS 6,241,670 B1 * 6/2001 Nambu ................ A61N 5/1048
                                                              378/65
6,246,200 B1    6/2001 Blumenkranz et al.
(Continued)

*Primary Examiner* — Sunita Reddy
(74) *Attorney, Agent, or Firm* — Brooke Schumm, III; Brooke Schumm PA

(57) ABSTRACT

This invention proposes a capsule to administer radiation to a patient to be mounted on an arm, preferably a robotic arm such as on and in coordination with a Da Vinci® Surgical Robot, in order to control radiation exposure using a cylindrical shell shutter system designed to minimize leakage from a centrally located radiation source, while permitting full exposure of irradiated subject material or space when the cylindrical shell shutter system is opened. Using a series of concentric cylindrical shells which each contain an offset conically-shaped aperture from that of an adjacent cylindrical shell, when the cylindrical shells rotate into an "open" position, the apertures form a smooth cone to an outer emission aperture and expose the radiation source to adjacent tissue. When rotated to be "closed" or "off, the offset apertures and shells occlude the source, preventing full-strength radiation exposure and minimizing radiation leakage.

40 Claims, 36 Drawing Sheets

(51) Int. Cl.
*A61B 90/00* (2016.01)
*A61B 90/30* (2016.01)

(52) U.S. Cl.
CPC ......... *A61N 5/1015* (2013.01); *A61N 5/1048* (2013.01); *A61B 2090/061* (2016.02); *A61B 2090/306* (2016.02); *A61B 2090/365* (2016.02); *A61B 2090/374* (2016.02); *A61B 2090/3762* (2016.02); *A61B 2090/3966* (2016.02); *A61N 2005/1052* (2013.01); *A61N 2005/1055* (2013.01); *A61N 2005/1061* (2013.01); *A61N 2005/1094* (2013.01)

(58) Field of Classification Search
CPC .... A61N 2005/1055; A61N 2005/1061; A61N 2005/1094; A61N 5/1001; A61B 34/35; A61B 90/361; A61B 90/37; A61B 2090/061; A61B 2090/306; A61B 2090/365; A61B 2090/374; A61B 2090/3762; A61B 2090/3966; A61B 2090/309; A61B 2090/3614; A61B 2090/373; A61B 2090/378
USPC ........................................................ 600/1–8
See application file for complete search history.

(56) References Cited

U.S. PATENT DOCUMENTS

| | | | | |
|---|---|---|---|---|
| 6,468,265 | B1 | 10/2002 | Evans et al. | |
| 6,491,699 | B1 * | 12/2002 | Henderson ............. | A61B 34/20 |
| | | | | 606/130 |
| 6,684,129 | B2 | 1/2004 | Salisbury, Jr. et al. | |
| 7,413,565 | B2 | 8/2008 | Wang et al. | |
| 8,092,370 | B2 | 1/2012 | Roberts | |
| 8,920,300 | B2 | 12/2014 | Roberts | |
| 2005/0008121 | A1 * | 1/2005 | Low .................... | A61N 5/1027 |
| | | | | 378/65 |
| 2008/0119687 | A1 * | 5/2008 | van't Hooft ......... | A61N 5/1027 |
| | | | | 600/7 |
| 2008/0247510 | A1 * | 10/2008 | Gertner ................. | A61B 6/508 |
| | | | | 378/65 |
| 2012/0016175 | A1 * | 1/2012 | Roberts ............... | A61N 5/1001 |
| | | | | 600/3 |
| 2013/0035536 | A1 * | 2/2013 | Francescatti ......... | A61N 5/1083 |
| | | | | 600/3 |
| 2016/0184605 | A1 * | 6/2016 | Roberts ............... | A61N 5/1014 |
| | | | | 600/7 |
| 2016/0193476 | A1 * | 7/2016 | Helekar .................. | A61N 2/12 |
| | | | | 600/15 |

* cited by examiner

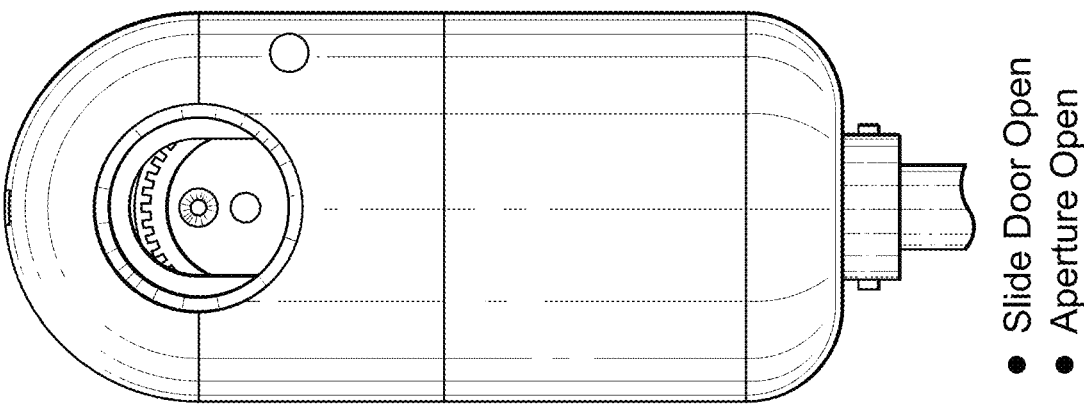
- Slide Door Open
- Aperture Open
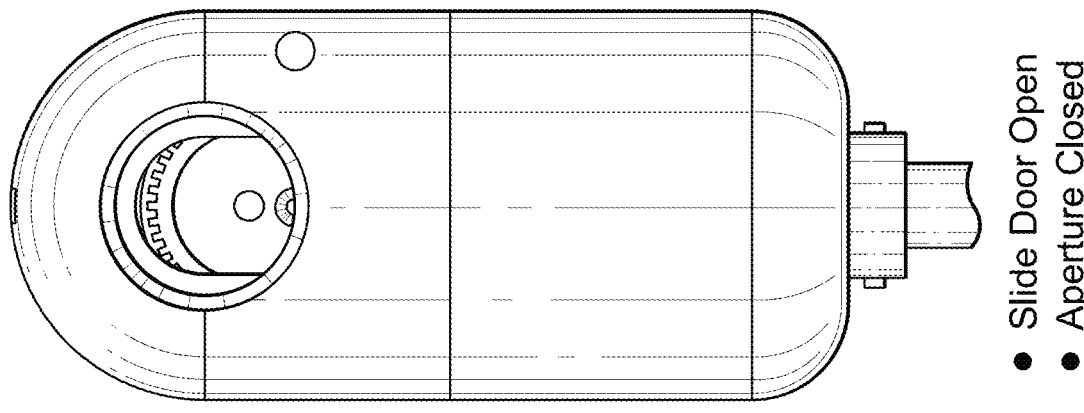
- Slide Door Open
- Aperture Closed
*FIG. 3*
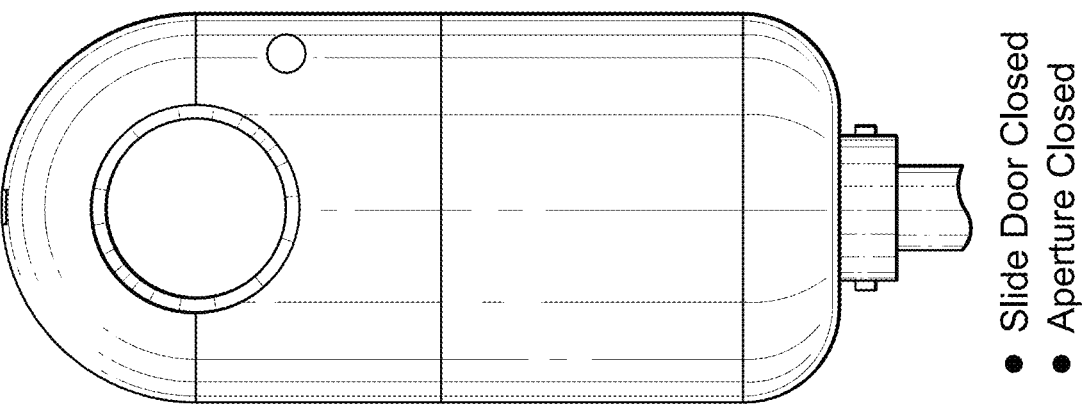
- Slide Door Closed
- Aperture Closed

SIDE VIEW

TOP VIEW

34

Longitudinal
cross-section
of push arm
and plates
showing tongue (47)
and grove (38)

27

Tab on Cap Piece

Coil Spring Closure Mechaniism

Coil
Spring

Coil Spring Retention Closure

INTRA-OPERATIVE RADIATION THERAPY CAPSULE WITH CYLINDRICAL SHELL RADIATION CONTAINMENT SHUTTER SYSTEM

FIELD OF INVENTION

This invention relates to an improvement on prior U.S. and foreign patents of radiation cancer treatment by a mobile miniature capsule or cassette containing a radioactive source deployed internally to a patient which is robotically manipulated having an openable aperture to allow radiation emission to more precisely destroy tumors, especially those on organs, and to obtain a quality margin while not destroying underlying healthy, essential tissue. The key improvement is the use of a series of cylindrical rotating shells about a central axis interior to a capsule to occlude radiation and expose a patient to radiation by a capsule on the end of a robot arm with a suitable operating mechanism. Cams as defined later are proposed to be driven by a motor, or less likely, a solenoid.

The invention enables close-confines radiation therapy. The invention enables the practical use of intraoperative irradiation, with alpha, beta and neutrons, x-ray, gamma or a combination thereof.

The text and figures of U.S. Pat. No. 8,092,370 Direct Visualization Robotic Intra-Operative Radiation Therapy Applicator Device, and the text and figures of U.S. Pat. No. 8,920,300 are adopted herein by reference, including the electromechanical elements, means, and methods of connection with a surgical robot. Large portions of prior description from those inventions in the '370 and '300 patents are repeated to illustrate the basic principles upon which this novel invention and its new elements are based. This invention has a re-designed shutter system to better attenuate radiation by a significant multiple using different elements which can be broadly used where a radiation source, is used in a patient for a radiation application device where compact size, highly directional irradiation, and limited leakage is of paramount importance using a series of concentric cylinders which when aligned form a uniform cone, and when offset correctly, maximize occlusion of radiation, and enable a compact arrangement with fewer air gaps.

SUMMARY

This invention proposes a robotic applicator device to be deployed internally to a patient having a capsule (also referred to as a cassette) and aperture with a means of alternately occluding and exposing a radioactive source through the aperture. The invention proposes some alternative shutter systems and retains the text of prior applications for contextual reference. The capsule and aperture will be integrated with a surgical robot to create a robotic IORT (intra-operative radiation therapy) applicator device as more fully described below. The capsule, radiation source, and IORT applicator arm would be integrated to enable a physician, physicist or technician to interactively internally view and select tissue for exposure to ionizing radiation in sufficient quantities to deliver therapeutic radiation doses to tissue, while avoiding exposure to personnel. Via the robotic manipulation device, the physician and physicist would remotely apply radiation to not only the tissue to be exposed, but also control the length of time of the exposure. Control means would be added to identify and calculate margin and depth of tissue to be treated and the proper radiation source or radioactive isotope (which can be any particle emitter, including neutron, x-ray, alpha, beta or gamma emitter) to obtain the desired therapeutic effects.

This invention described herein comprises the integration of a radiation application device with a surgical robotic machine for the purpose of allowing a novel form of radiotherapy treatment internally to a person having a cancer or other neoplasm consisting of one or more tumors by attaching and integrating a capsule containing a radiation producing isotope or x-ray or particle generator with an occlusive shielding mechanism to permit the introduction, visualization and aiming of a precise radiation field to expose the cancerous and benign tumors to a lethal dose of radiation under the remote guidance of the surgical robot systems. This invention will permit, under robotic control, the selection of a capsule, attachment to the surgical robotic arms and introduction of the radiation into the patient under direct and imaging guided visualization for the purpose of exposing cancerous tissues, intra-operatively to doses of radiation by exposing the tumor cells to a radiation field for an adequate amount of time to render them incapable of further growth and thus, limiting further growth of the diseased tumor cells.

As this invention is intended to be used intra-operatively, surgeons skilled in the art of cancer surgery, together with radiation oncologists and medical physicists skilled in the art of using and delivering radiation treatments will use the invention cooperatively at the time of surgical removal of the tumor and at subsequent intervals as may be necessary to deliver radiation treatments intra-operatively as part of a planned surgical procedure to deliver curative doses of radiation to tumors. The invention, using imaging techniques such as ultrasound, MRI, CT, PET or PET/CT or some combination of medical imaging guidance, a priori or contemporaneously with the surgical procedure to guide and direct the radiation oncologist in the correct and accurate placement of the radiation field inside the patient and timing of tissue exposures to produce a curative dose of radiation without delivering doses to uninvolved tissues to minimize, to the greatest extent possible the complications associated with radiation treatment and delivery. The invention described herein will allow the operator to identify neoplastic tissue (benign or cancerous) of interest to the operator via medical imaging as described above, real time guidance via spatial depiction of the key anatomical landmarks at the time of insertion of the capsule for irradiation intra-operatively, real-time depiction in 3-dimensions on the imaging display system of the precise position of the applicator through the surgical robots' positioning reporting technologies and under direct visualization using visible light techniques and permit the operator to precisely position the intraoperative radiotherapy capsule in such a way, within the human body, using the surgical robotic manipulator arms under remote control of the robot by the physician, to deliver the proper type and exposure of radiation to the neoplastic tumors, thus enhancing the probability of curing and/or better managing the disease.

One optimal application would be a radiation ablation capsule mounted onto an arm of a da Vinci® surgical robot machine. The preferred isotope for the preferred mode is for an Iridium-192 radioactive isotope that will emit radiation to eliminate cancerous tissue. The capsule would enable the radiation oncologist and surgeon, upon completion of surgery, to immediately, while the patient is under anesthesia, ablate (bombard with radiation) cancer sites internal to the patient, view them visually in real time and examine the tissue and determine if any further ablation is needed.

BACKGROUND

Traditionally, intraoperative radiation therapy has been delivered via large, cumbersome linear accelerators and via injections of radioactive substances, both of which can cause substantial collateral damage and resultant morbidity and have not been shown to substantially improve outcomes.

A significant and longstanding problem with many cancers, such as ovarian cancer, is that upon resection (surgery), it is difficult to obtain what is referred to as a clear margin, or optimal debulking, that is a complete surgical removal of all cancer, including microscopic cancer. As a result, residual cancer cells frequently remain, and may (and often do) break off from the primary cancer and migrate to other locations which are difficult to reach and destroy. Moreover, the other sites to which the cancer cells may migrate (metastasize), are often adjacent to and on sensitive organ tissue, even if they have not invaded the organ at the time of discovery. The metastatic cancer cells will then begin to grow using the local blood supply of the new site of involvement, eventually compromising organ function, and ultimately destroying the organ, frequently resulting in death.

Traditional external beam radiation therapy techniques frequently are ineffective in treating such localized metastases due to the relative toxicity of radiation delivered to the involved organ. A dose of radiation sufficient to destroy the cancer will be likewise fatal to the involved tissue or organ at issue due to the inability in the non-operative setting to deliver a specific dose to only the cancerous lesions. The inability of external beam radiotherapy to precisely target a small metastatic lesion is well documented and relates to a.) inability to visualize small lesions on CT/MR/PET with high precision b.) inability to identify and track organ motion in real time for the period needed to precisely target a small cancerous lesion c.) inability to restrict the external beam dose using conventional, conformal, IMRT, cyberknife or tomography techniques to the cancerous lesions enough to deliver sufficient dose to the tumor without unacceptable normal organ damage.

The statistics supporting complete removal (i.e. optimal surgical excision) are very compelling. Research has demonstrated that for locally advanced ovarian cancer, the prognosis is dismal and for Stage III ovarian cancers, comprising 51% of all ovarian cancer cases, as an example, the five year survival rate for optimally debulked cancers (no gross residual disease apparent), is between 21% and 5%, and there has been little change in mortality in the last 25 years, despite advances in chemotherapy and surgical techniques. [Gunderson].

The volume of residual disease is an important prognostic indicator supported by numerous studies demonstrating the value of cytoreductive surgery (i.e. the complete removal of all visible cancer cells), both in primary and secondary procedures. That is, the larger the volume of residual disease, the poorer the prognosis. Cytoreductive procedures have been shown to prolong progression free survival intervals and overall survival for patients with disease less than cm remaining. For these patients, treatment with chemotherapeutic agents has been helpful, but ovarian cancer progression and death remains high. The value of reducing residual disease has been shown to be important. With no residual disease, median survival was 39 months, with <0.5 cm residual disease, median survival dropped to 29 months, with residual disease between 0.5 cm and 1.5 cm, 18 months and less than 11 months for residual disease greater than 1.5 cm. [Griffiths].

Radiation therapy is a well known treatment modality for neoplastic (cancerous) disease. Radiation therapy has been tried without success in treating abdominal cancers in general, due the inability to deliver dose specifically to sites of residual disease without producing unacceptable morbidity and mortality due to the highly sensitive normal tissues in the abdomen. Intraoperative radiation therapy has not been widely adapted due to the previous inability to precisely deliver radiation to tumors while minimizing dose to normal tissues.

Other attempts at delivering radioactive seeds include placing catheters, but absent a robotic arm device and the dose delivery apparatus contemplated in this invention and the real time dosimetry and source selection during the surgical procedures, the delivery methods are inflexible and cannot be precisely guided in the way that the invention proposes, and cannot be rapidly repositioned during the course of the treatment. In other words, once a catheter has been placed, it is fixed and immobile absent a second operation, while the proposed invention will allow immediate and precise positioning at the time of the surgery, allowing flexibility and precision unobtainable with the traditional methods of catheter placement.

This invention proposes to be integrated with recent technologies developed and owned by Intuitive Surgical, Inc., called the DaVinci Robotic Surgery Device, a form of intra-operative robotic surgical device, and more generally to intra-operative robotic surgical devices, including a Bright Lase Ultra Laser™ surgical laser mad by QPC Lasers of Sylvan, CA. Examples of technology related to intra-operative robotic surgical devices can be found in "Performing cardiac surgery without cardioplegia," Evans et al, U.S. Pat. No. 6,468,265, Oct. 22, 2002; "Manipulator positioning linkage for robotic surgery," Blumenkranz et al, U.S. Pat. No. 6,246,200, Jun. 12, 2001, "Master having redundant degrees of freedom," Salisbury, Jr. et al, U.S. Pat. No. 6,684,129, Jan. 27, 2004; and devices illustrating automated control such as "Minimally invasive surgical training using robotics and telecollaboration," Wang et al, U.S. Pat. No. 7,413,565, Aug. 19, 2008, the descriptions in which are adopted by reference to illustrate surgical robotic intra-operative surgical devices and integrated surgical robotic intra-operative systems. The field of radiation oncology has changed markedly with the introduction of imaging based radiation therapy treatment planning in the early 1990s for external beam radiation therapy. After physically removing as much of the tumor as possible, at present, a linear accelerator is used to deliver a concentrated dosage of radiation directly onto the exposed cancerous tissue. An example of such a linear accelerator is the IntraOp Mobetron® electron linear accelerator (registered trademark of IntraOp Medical Corp.), now manufactured by Phillips which uses a linear acceleration radiation system. The technologies that make this possible have allowed the design of precision radiation fields to treat cancers in ways that were previously not possible, but have a clumsy aspect because of their size. which renders them unable to be precisely manipulated into a position where the therapeutic beam can be optimally aimed to provide maximum therapeutic advantage: i.e., the targeting of high risk tumor areas while avoiding dose to uninvolved tissue. This difficulty is particularly problematic in the treatment of abdominal cancers where tumors are often on or near radiation-sensitive vital organs. The radiation oncologist is not able to manipulate an external beam of radiation sufficiently to avoid collateral damage of other healthy tissues in the abdominal cavity.

There has been a long felt need to be able to precisely target cancers and other tumors in the intra-operative setting as well. The development of the DaVinci style intra-operative surgical device and like devices (also more generically referred to as a "surgical robot") creates a new avenue to exploit in the pursuit of this goal, which avenue is the subject of this invention.

For the purposes of this invention, a device which proposes to stabilize the patient and then robotically undertake surgery and treatment with the physician operating at least one robotic device or arm shall be referred to as a surgical robot. For the purposes of this invention, a surgical robot which uses the radiotherapy capsule or cassette and related guidance systems as an attachment to a robotic manipulator arm shall be referred to as a surgical robotic intra-operative radiation therapy device, or SRIORT.

This invention is unique in that the device allows the physician to identify and deliver a lethal radiation dose to one or more tumor sites at the time of surgery in real time under direct visualization. By contrast, under the present art, an applicator is put in place and at a later date and time post-operatively deliver radiation using devices such as the Mammosite® balloon/catheter type devices or a flat square of material containing afterloading catheters through which a radioactive source may be placed at a later date and time.

As previously stated, intraoperative radiation post-surgical therapy and therapy during surgery have been delivered via large, cumbersome linear accelerators and via injections of radioactive substances, both of which can cause substantial collateral damage and resultant morbidity and have not been shown to substantially improve outcomes.

Other approaches are inflexible and cannot be precisely guided in the way that the invention proposes, and cannot be rapidly repositioned during the course of the treatment. In other words, once a catheter has been placed, it is fixed and immobile absent a second operation, while the proposed invention will allow immediate and precise positioning at the time of the surgery, allowing flexibility and precision unobtainable with the traditional methods of catheter placement. An additional benefit is that the proposed invention will permit the introduction of intra-operative radiation therapy during a closed laparoscopic procedure rather than requiring an open procedure as is presently required with linear accelerator based intra-operative techniques.

This invention proposes a new addition to IORT that enables a much more highly specific targeted treatment of cancerous tissue and can direct radiation from different angles as needed to minimize vital organ damage while applying lethal doses of radiation localized to the cancerous lesion.

The SRIORT device will overcome disadvantages in the present art by combining the ability to deliver precise, robotically performed surgery using a surgical robot, followed by the ability, in the operating room, using the same surgical robot, to attach the SRIORT device containing a radioisotope with high specific activity and energy characteristics, combined with a movable aperture, aiming device and dosing and timing logic which will enable the delivery of radiation in a highly localized manner to treat areas of known or suspected residual disease while sparing normal tissue radiation dose, thus creating a substantial therapeutic advantage. This device will combine PET/CT/MR and direct imaging modalities, including video imaging, intraoperative ultrasonic imaging, and tactile response sensors to precisely identify the areas to be treated, the depth of desired treatment and the radiation dose needed.

As the SRIORT device will permit the intra-operative placement of a radiation field directly on a tumor site, in real time, without the need for an open laparotomy as is the case in conventional intraoperative radiotherapy, and at the same time the robotic component will permit the surgeon and radiation oncologist to safely place the desired treatments in real time in the operating room with minimal to no personnel exposure to ionizing radiation, this invention represents a dramatic step forward in the art of radiation therapy. It will eliminate the need for open surgery, utilize minimally invasive surgery, and will reduce the need for a second operation for traditional catheter based brachytherapy.

The application of the invention also contemplates delivery of radiation to what have been viewed as "inoperable" cancers because of proximity to critical tissue. This invention enables stereotactical intervention by radiation in a precise manner adjacent to radiosensitive tissue not ordinarily amenable to radiation therapy without lethal or undesired consequences.

By way of further background, currently, intra-operative radiation therapy has been delivered via large, cumbersome linear accelerators. These have been shown to substantially improve outcomes, but have harsh side effects. For ablation of internal tissue by a linear accelerator, a patient has to be surgically open and due to the large size and heavy shielding requirements, the procedure is infrequently used or not available. The invention would permit frequent use and would function in conjunction with an already existing machine, the da Vinci Surgical System® intra-operative surgical robot produced by Intuitive Surgical, Inc. of Sunnyvale, California. Side effects are significantly reduced because the capsule delivers precise radiation to tumor sites, while the dose to normal tissue is minimized.

Intra-operative radiation therapy contemplated in this invention is used primarily to treat tumors that cannot be completely removed surgically because of their close proximity to vital, healthy tissue.

This invention proposes a method and mechanism of controlling radiation exposure using a capsule to administer radiation to a patient to be mounted on an arm, preferably a robotic arm such as on and in coordination with a Da Vinci® Surgical Robot, in order to administer and control radiation exposure using a cylindrical shell shutter mechanism designed to minimize leakage from a centrally located radiation source, while permitting full exposure of irradiated subject material or space when the shutter is opened. The invention uses a different set of elements and structure from prior art in order to achieve homogeneous solid angle divergence of beam port from the radiation source and virtually eliminate significant voids with minimal radiation attenuation in the voids. Using a series of concentric cylindrical shells which each contain an offset conically-shaped aperture from that of an adjacent cylindrical shell, when the cylindrical shells rotate into an "open" position, the apertures form a smooth cone to an outer emission aperture and expose the radiation source to adjacent tissue. When rotated to be "closed" or "off", the offset apertures and shells occlude the source, preventing full-strength radiation exposure and minimizing radiation leakage.

The proposed shutter mechanism permits a very stable fixed location source with exposure controlled by exposing and occluding the source. It limits leakage by preventing a large gap in the radiation source to applicator surface at any given point and augments the effectiveness of a fail-safe mechanism by means of an automatic closure mechanism which will continue to function albeit at reduced effectiveness even if one of the shells jams, giving time to remove the compact applicator from the working environment to a safe area, which will minimize unplanned exposure.

Due to the nature of radiation, conventional shutter systems using single plane shutters must be large enough and have a high enough electron density (high atomic number or Z and material density) construction to prevent or minimize radiation leakage from byproduct material radiation sources. Present methods of occluding a radiation source include moving the source mechanically away from the aperture to an area with increased shielding, or closing, obstructing jaws. However, such methods and devices may leave large air voids which create a need for shielding in order to compensate for the void to diminish radiation exterior to the device. This results in a larger than necessary device to accommodate extra shielding. In addition, due to the need for mechanical components to actuate and drive the sliding shutter, differential shielding is obtained resulting in uneven leakage or a localized hot spot. The sliding shutter approach also typically leaves a non-uniform path length in the region the shutter is parked when radiation is desired, which could result in undesirable penumbra effects due to partial excess transmission of radiation through the thinner regions of the shutter resulting in uneven irradiation to the subject material which could cause underexposure at the boundaries of the field, or necessitates even further voids to avoid penumbra. (FIG. 15). Because the shutter must close the beam path completely, and the beam path must accommodate the shutter, there will be resulting air gaps along the radiation pathway which will create undesirable variances in the radiation beam intensity at the target, or, alternatively, require the device to be much larger than anticipated (double the length) to create a second position on the sliding shutter, containing the desired transmission pathway to insure a uniform distance through shielding material with minimal transmission path lengths through air or excess material.

OBJECTIVES OF THE INVENTION

A first objective of the invention is to enable non-surgical precise improvement of margins by intra-body irradiation which cannot be safely done by a human in close proximity to the capsule and tissue to be irradiated. The capsule must be small enough to be mobile within a human body cavity. The capsule should adequately shield both patient and surgeon from unwanted radiation exposure A second objective is to enable visual examination of tissue adjacent to surgically removed tissue, and on a real-time basis, irradiate tissue that needs to be eliminated, or irradiate tissue to increase the margin from removed tissue.

A third objective is to enable removal of tissue to precise depths by irradiation inside the patient's body, including while visually examining such tissue, so that "inoperable," meaning tissue that is radiosensitive, or dangerous to excise, can be precisely removed or avoided. The aperture through which radiation is emitted must align accurately with radiation source for successful exposure.

A fourth objective is to enable visualization and removal of small lesions, including those detected on CT/MR/PET, with high precision.

A fifth objective is to identify and track organ or tissue motion in real time for the period needed to precisely target a small cancerous lesion, and adjust irradiation to coordination with organ or tissue motion.

A sixth objective is to restrict irradiation to benign, malignant, or cancerous lesions enough to deliver sufficient dose to the tumor without unacceptable normal organ damage, and avoid the imprecision and collateral damage from the inability to restrict the external beam dose using conventional, conformal, IMRT, cyberknife or tomography techniques to the precise lesion and desired margin. The radiation must produce a circular pattern of a known diameter through a conical hole with minimal penumbra. The doors or shutters must fully open and close for every cycle.

A seventh objective is to use the increased velocity and accuracy with which a surgical robot can move to minimize invasive time that would be required and simultaneously decrease unnecessary time of exposure to radiation. Concurrently, a smooth capsule surface prevents the capsule from snagging on any tissue it comes in contact with.

FIGURES

FIG. 1A shows a schematic of the capsule.

FIG. 1B shows the relative positions of the body tissue with the tumor nodule (an example of 4 mm. depth is shown) which is being targeted disposed on said tissue. A simplified diagram of a shroud containing a locator mechanism is shown over the tissue, with the cassette (usually called a capsule in the description) containing the radioactive substance, and the general disposition of the capsule on a robotic arm, also sometimes referred to in the trade as a "instrument" which "instrument" on the DaVinci surgical system is mounted on the DaVinci surgical system robot arm.

FIG. 3 shows the position of the slide door, aperture disk and radioisotope relative to the capsule in various positions.

Figure 9:
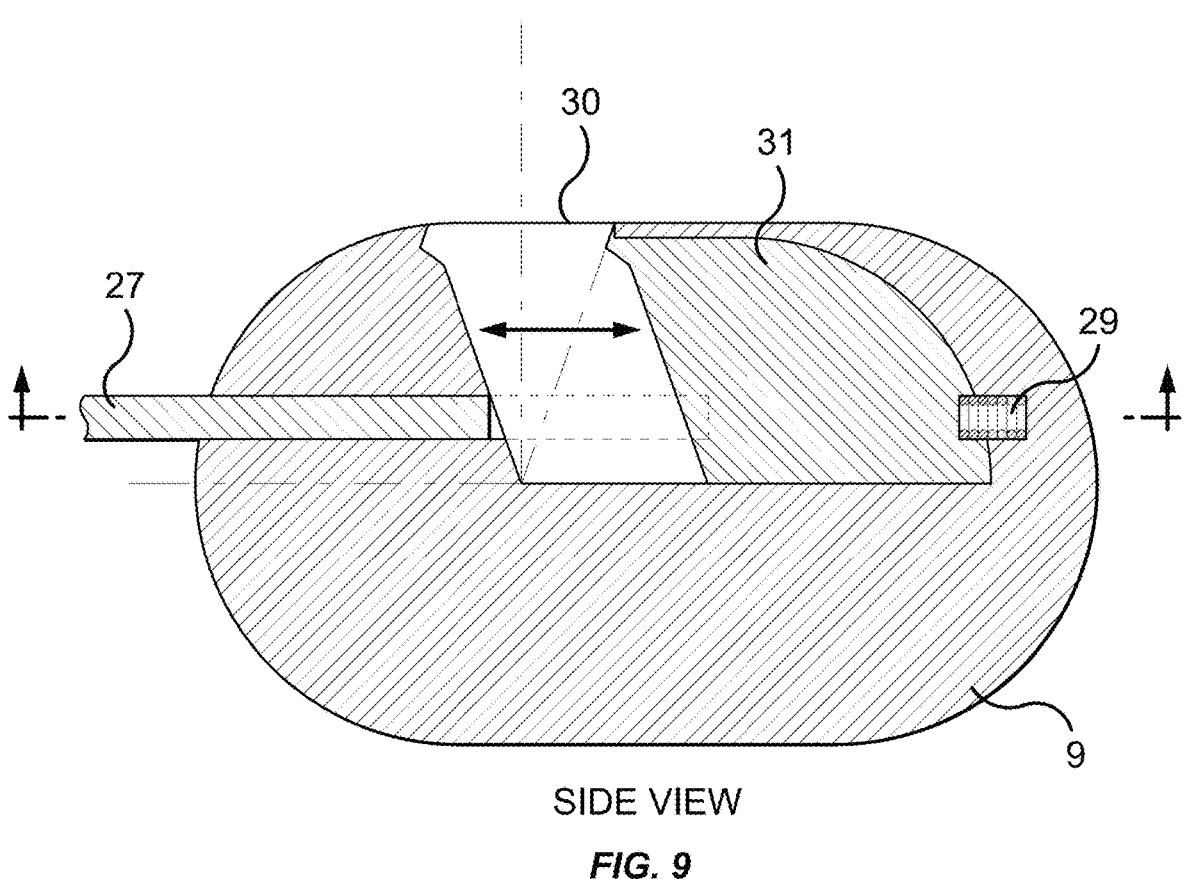
FIG. 9 shows a side view cross-section of a capsule with a movable shutter with a push rod moving the shutter against a spring.
Figures 11, 12:
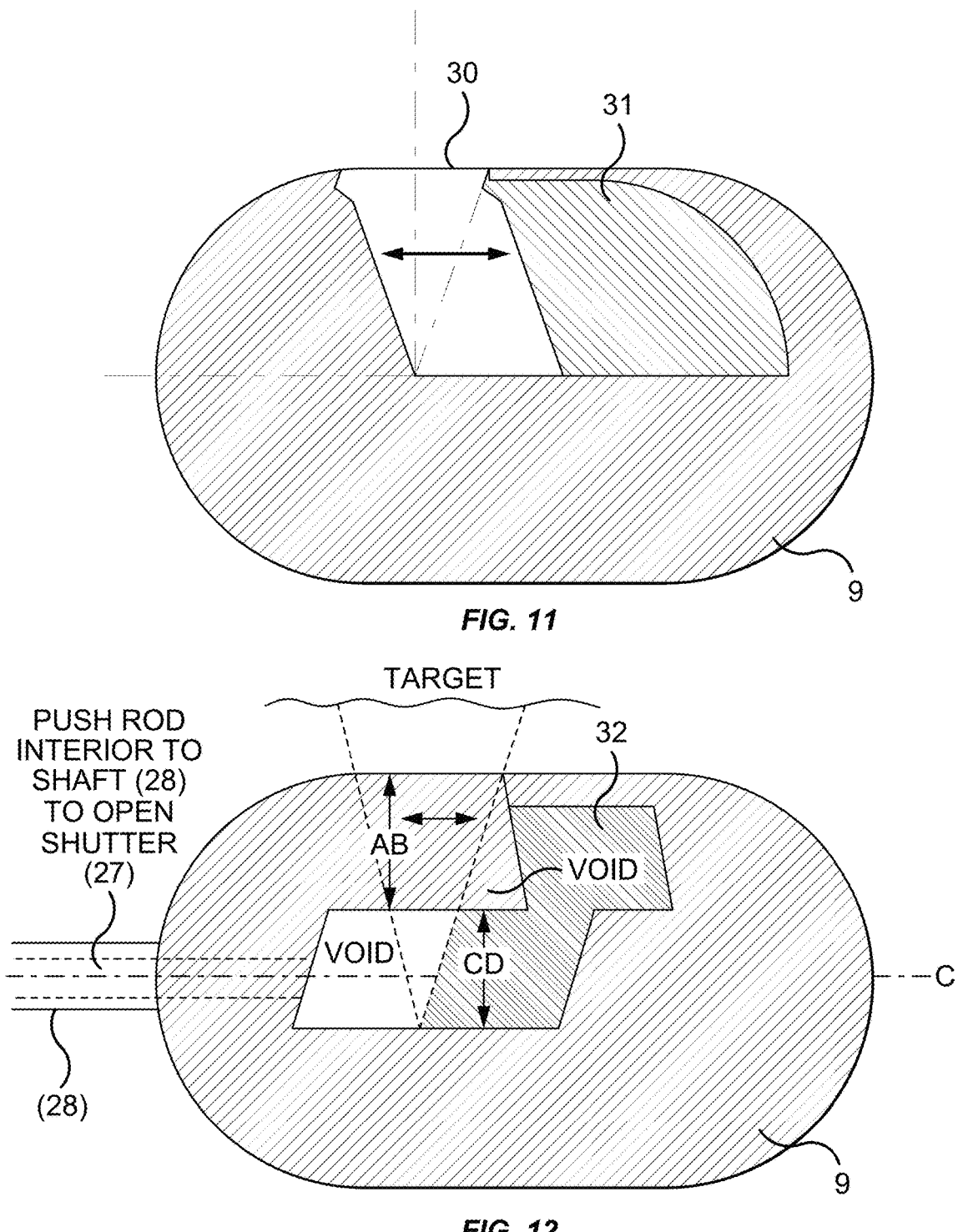

FIG. 11 I a simplified view showing the geometry of FIG. 9.

FIG. 12 is another shutter design operated by a push rod.

Figure 13:
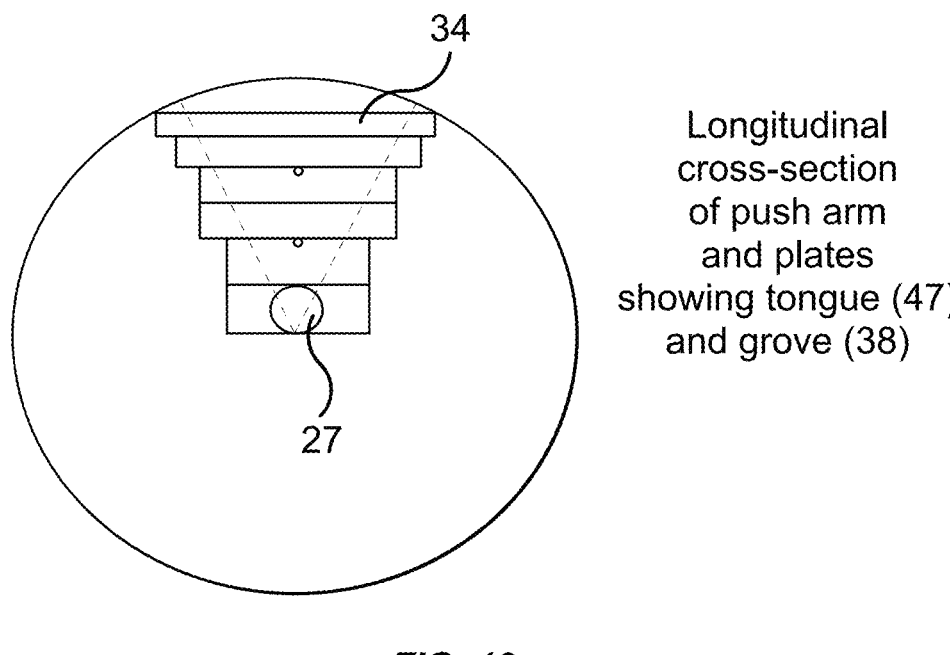
Figure 14:
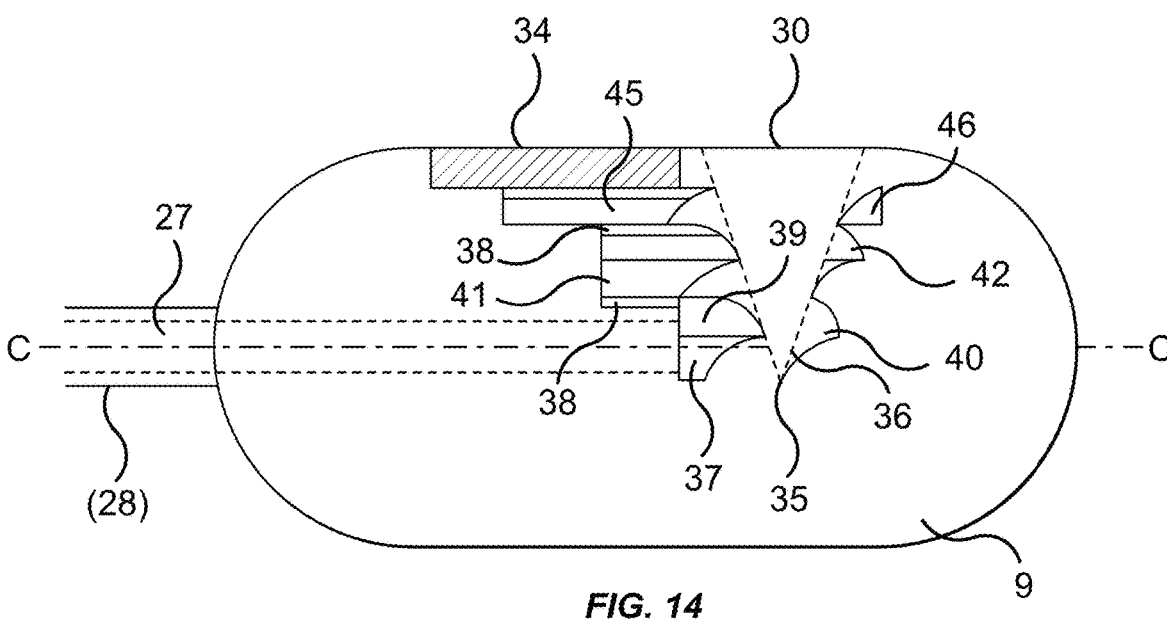

FIG. 13 is an end view of the capsule showing the multiple plate design of FIG. 14.

FIG. 14 is a detail view of the multiple plate design operated by a push rod moving the plates constituting the shutter into moving plate receptacles.

Figure 15:
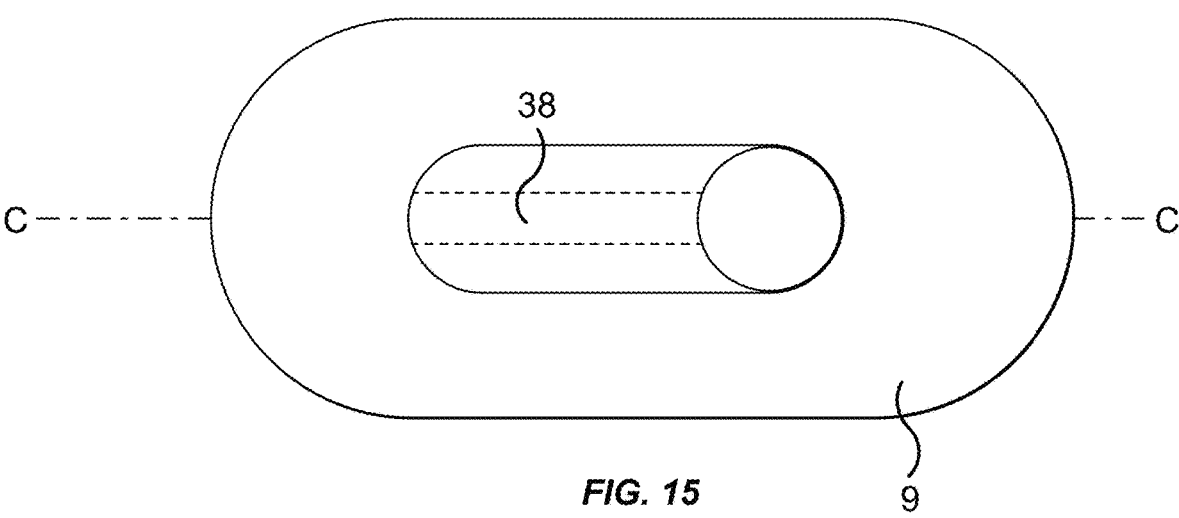

FIG. 15 is a top view looking down toward the aperture of the capsule showing the relative location of the moving plates constituting the shutter to occlude the radionuclide.

Figure 16:
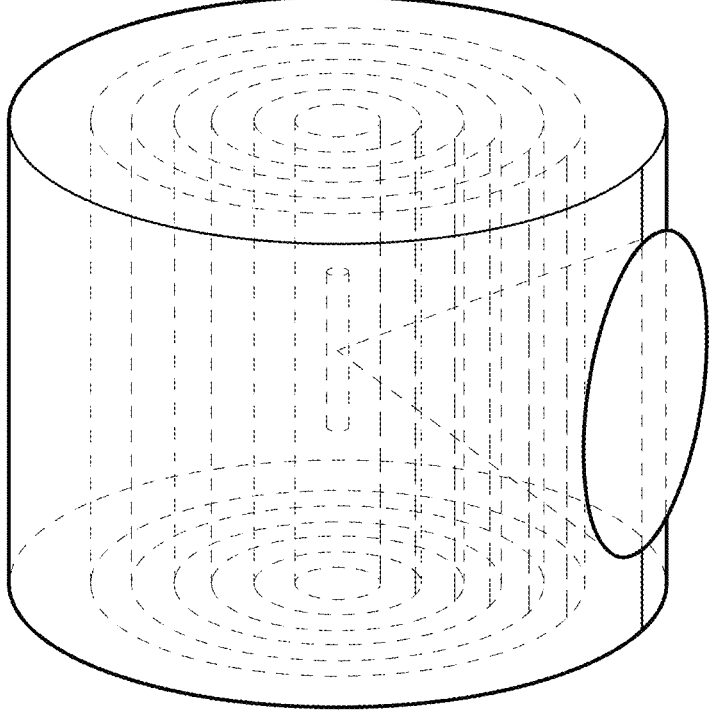

FIG. 16 shows a cylindrical shell radiation shutter system showing radiation source at center, concentric shells with apertures aligned allowing exposure through the outermost beam port (emission aperture located on the capsule).

Figure 17:
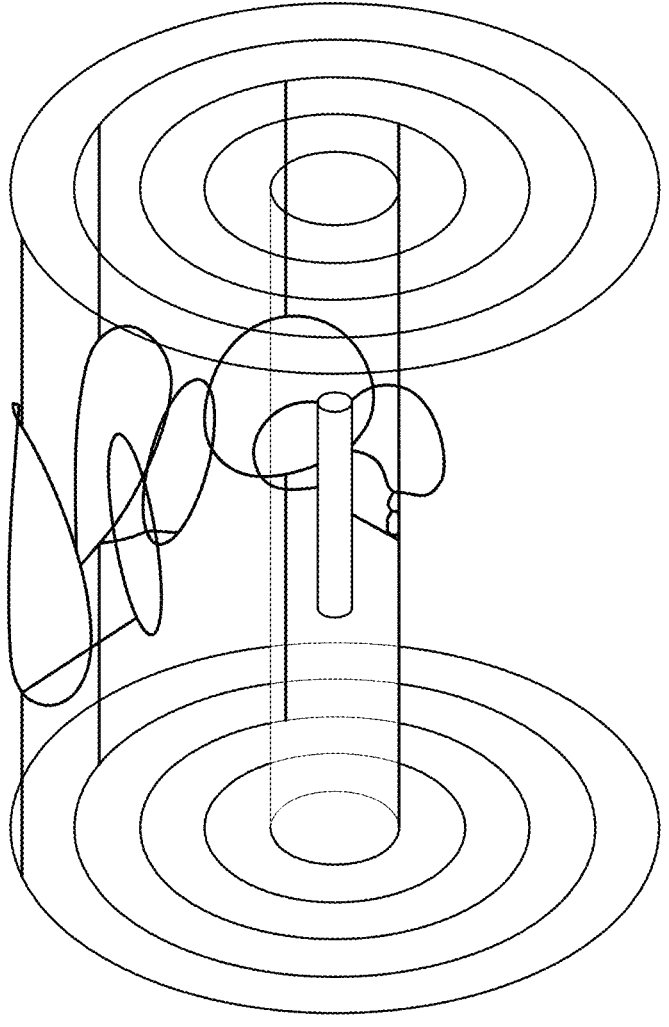

FIG. 17 shows a cylindrical shell radiation shutter system showing source at center with all cylindrical shell apertures offset from each other thereby obstructing the source and shielding the radiation source from the exterior of the capsule.

Figure 18:
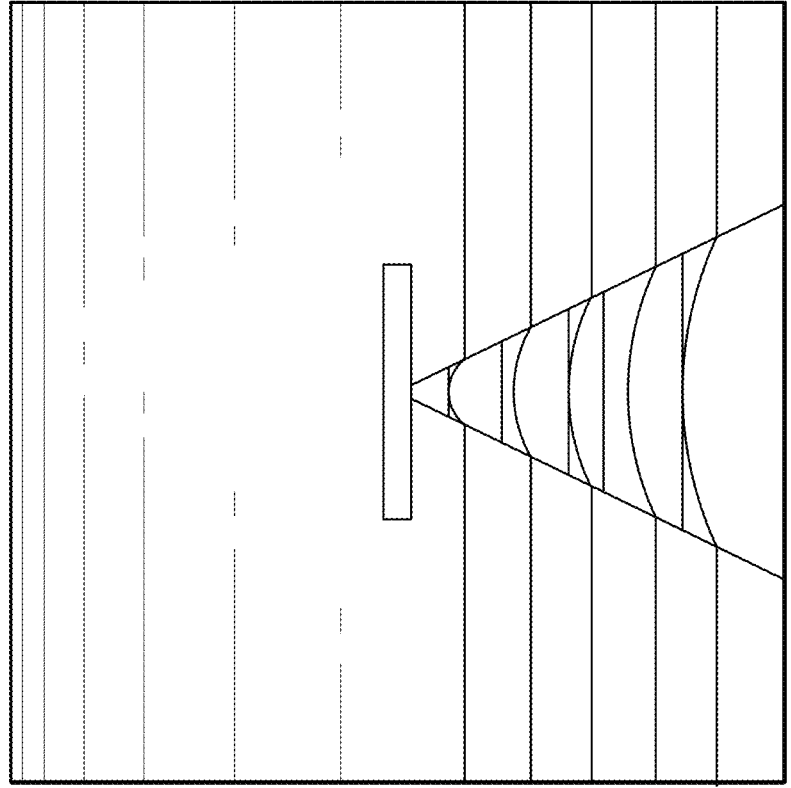

FIG. 18 shows a cylindrical shell radiation shutter system lateral view showing shutters open. The lines within the spreading cone are intended to generally illustrate the homogeneity of the spreading cone.

Figure 19:
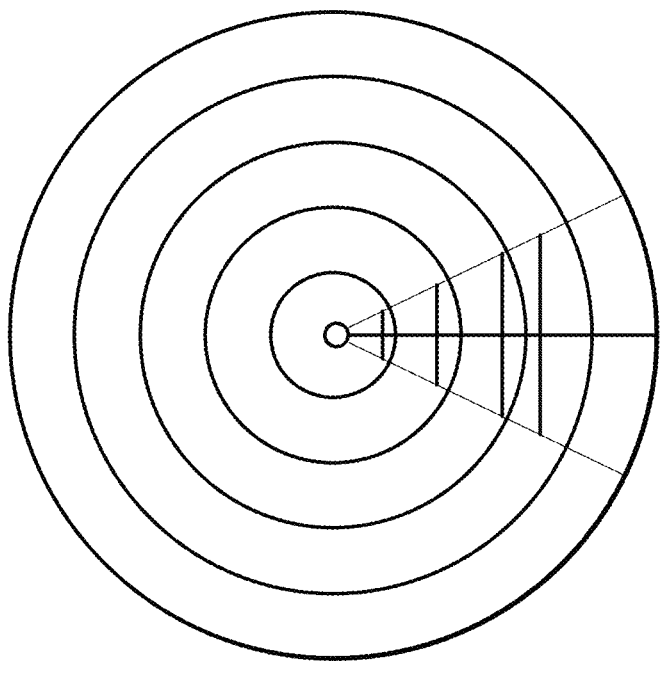

FIG. 19 shows a cylindrical shell radiation shutter system showing source at center with all cylindrical shell apertures aligned with each other permitting irradiation exterior to the capsule along the beam path. The lines within the spreading cone are intended to generally illustrate the homogeneity of the spreading cone.

Figure 20:
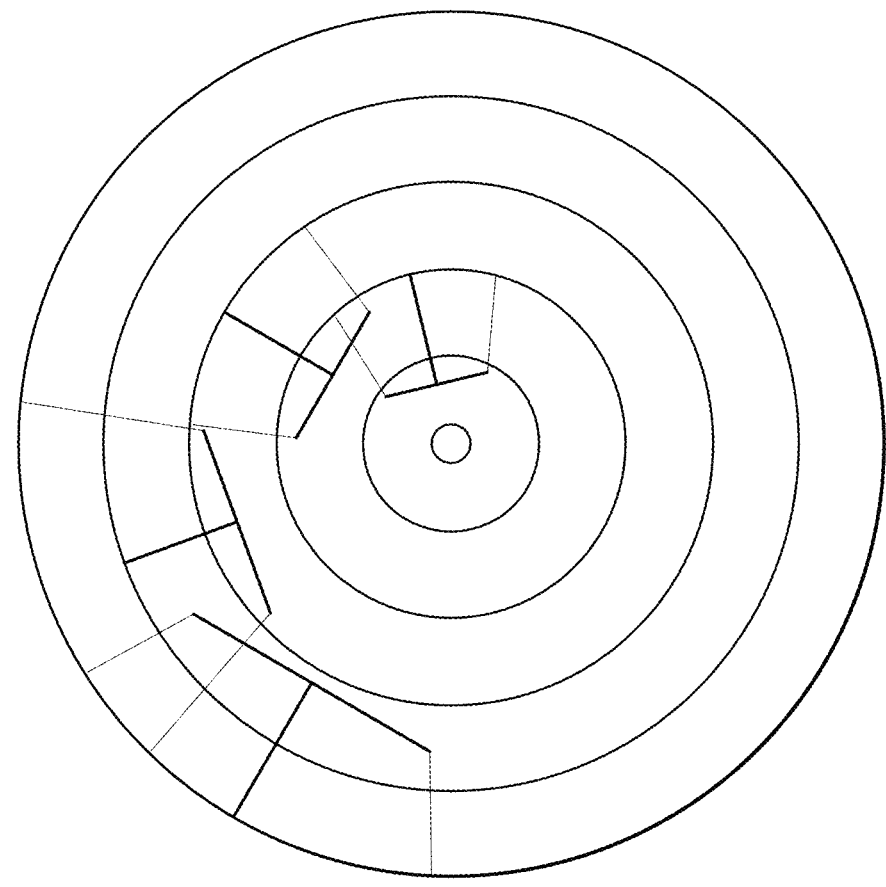

FIG. 20 shows a top view of the cylindrical shell radiation shutter system showing source at center with all cylindrical shell apertures offset from each other occluding the source and preventing significant irradiation exterior to the capsule. The lines appearing as a "T" are meant to approximately illustrate the gradually widening cone from cylindrical shell to cylindrical shell which, when the cylindrical shells are aligned, will result in the homogeneity of the spreading cone.

Figure 21:
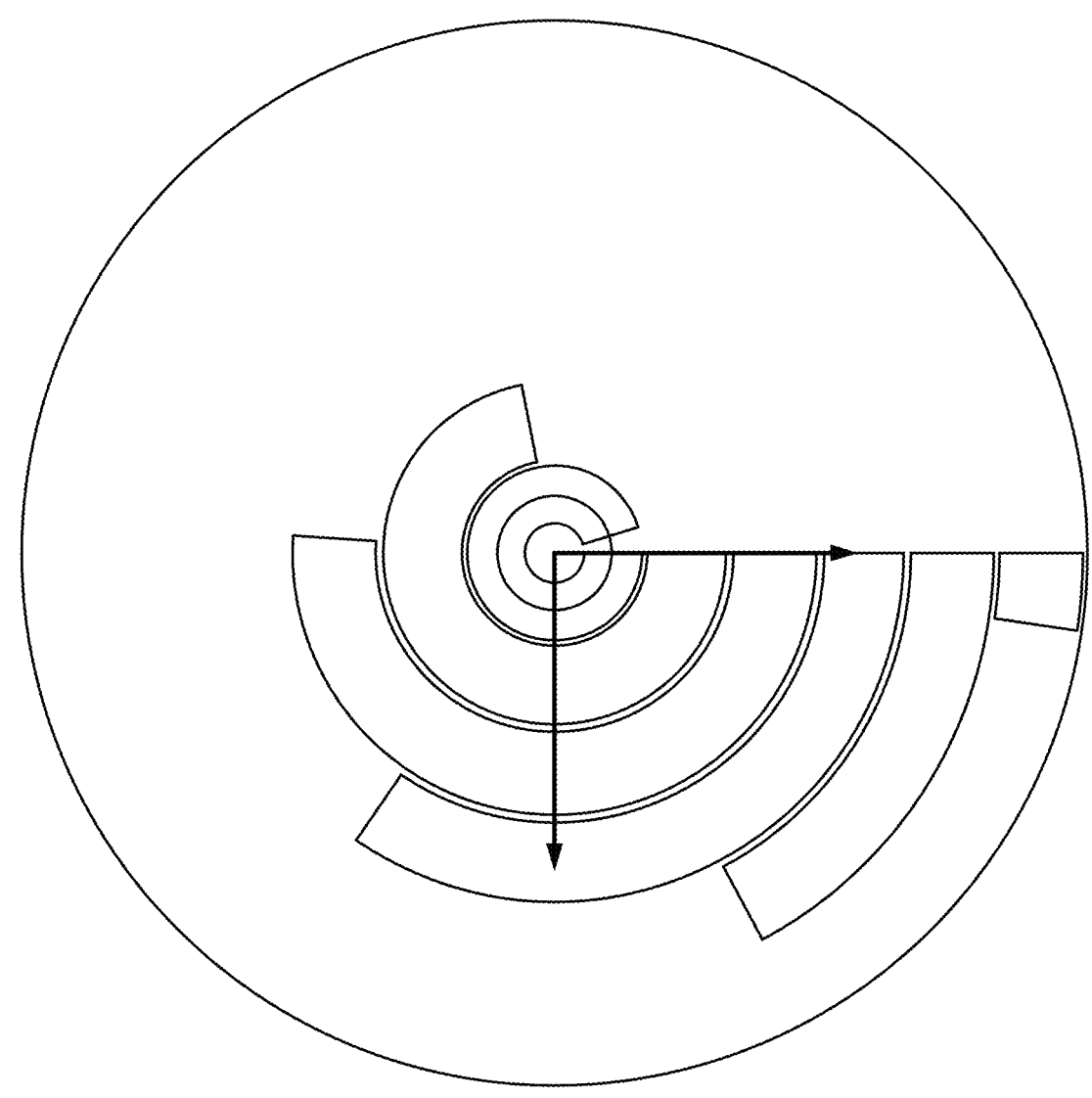

FIG. 21 shows a proposed gear plate: The gear plate in this figure shows variable length slots, all with one edge aligned in a series of 6 tracks in this example, but could consist of any reasonable number of tracks, corresponding with shutter thickness desired and number of shutters (in this instance a number of six shutters has been selected, but the number can vary in a range of 1, 2, 3, 4, 5, 6, 7, 8, 9, 10 or integral numbers up to 20, although after a point the more shutters, the air gaps created and the less cost-effective the device will be; here the numbers of shutters is selected as six to illustrate the invention (inner to outer, which have been labeled A, B, C, D, E, F arbitrarily). The slots when rotated clockwise align the apertures with the case aperture, exposing the source. When rotated counter-clockwise, the shell apertures are not aligned with the source or each other thereby obstructing the source and shielding the radiation source from the exterior of the capsule.

Figure 22:
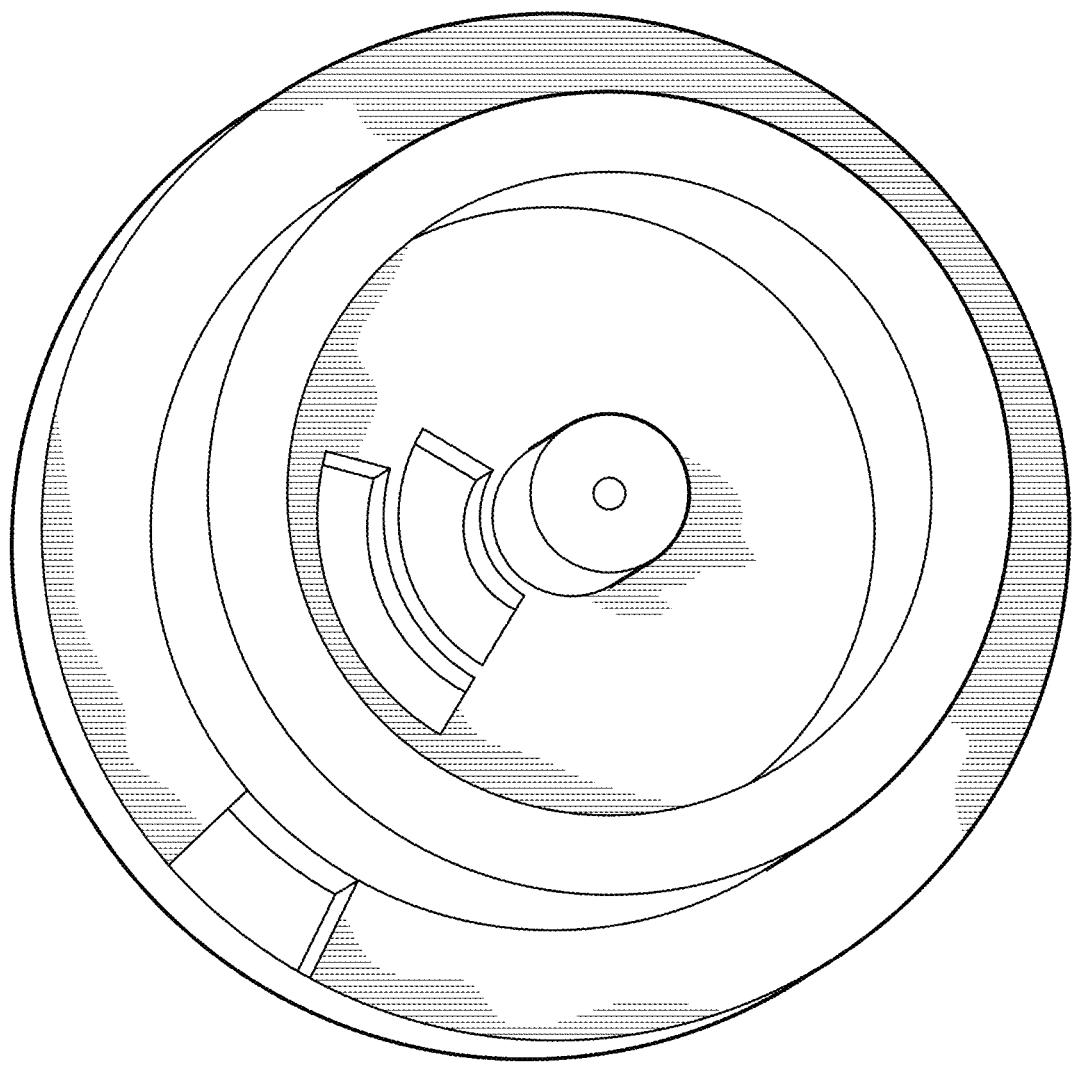

FIG. 22 shows a Top Oblique View of the gear plate top oblique view showing two cylinders of six in this example. The other cylinders have been removed to show the underlying mechanism. Cylinder A (inner most) and Cylinder E (second from outer most) are shown with apertures aligned (open). The gear slots of varying lengths are shown on the gear plate.

Figure 23:
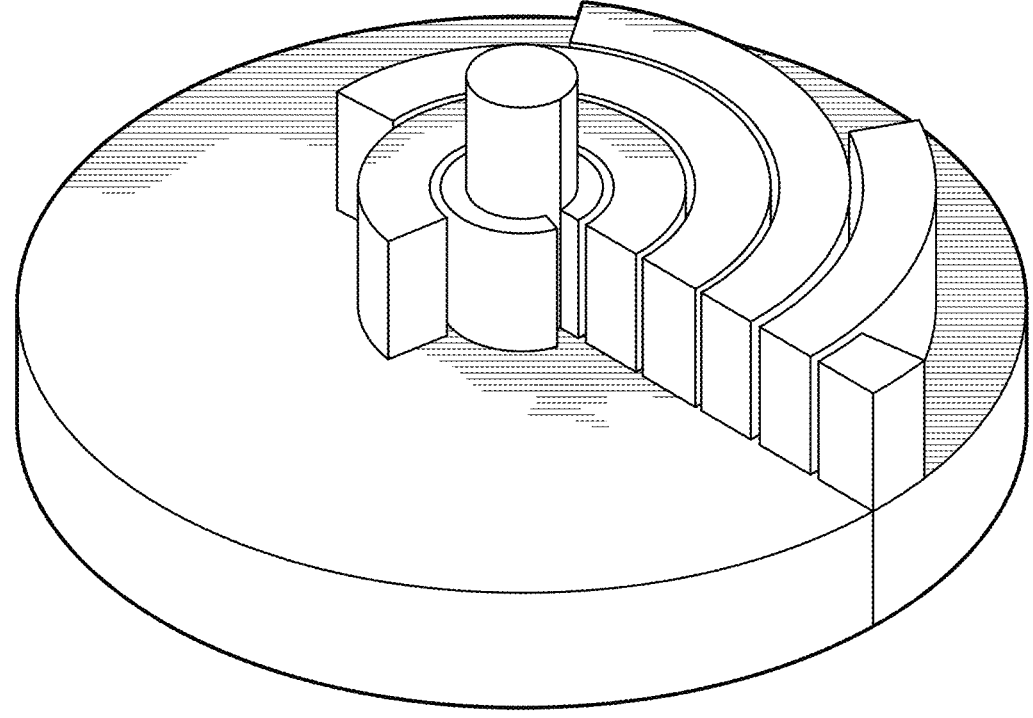

FIG. 23 shows an alternative gear plate showing raised drive surfaces arranged in tracks, which would mate with corresponding slots in each cylindrical shell shutter component causing variable motion and alignment. In this arrangement a cam plate is used, each fixed to each other, or alternatively independently rotatable with individual stepping motors. In this case, the raised surfaces would be either a fixed length with variable independent rotation or as shown with fixed rotation of all tracks.

Figure 24:
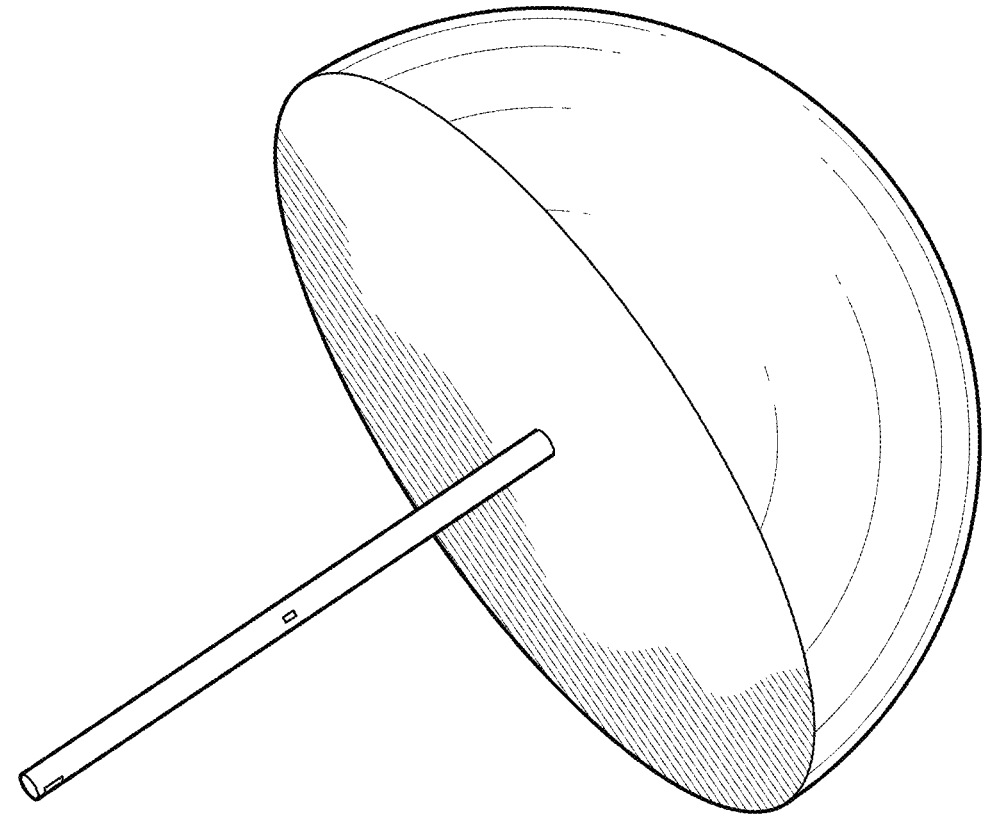

FIG. 24 shows a source rod and cap assembly with source in center of source containment rod. The source is fixed in the central rod which is inserted into the cylindrical shutter system such that the source is precisely located at the center of the aperture beam ports. The lower tab on the source rod demonstrates one means of locking the capsule system into place, thus affixing the source in the desired position.

Figure 25:
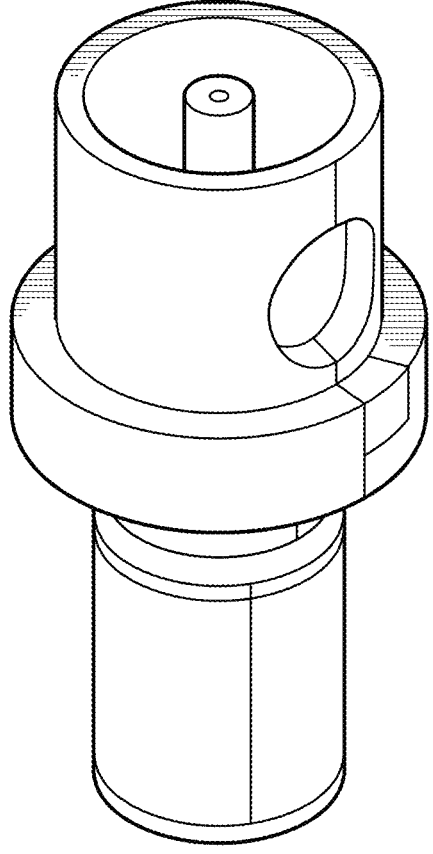

FIG. 25 shows two shutter cylinder components shown in position on gear plate with outer shell removed. The outer track gear slot is shown immediately below the aperture of the next inner shell. The innermost shell is shown in the center of the gear plate assembly, and the drive motor is shown attached to the gear plate below.

Figure 26:
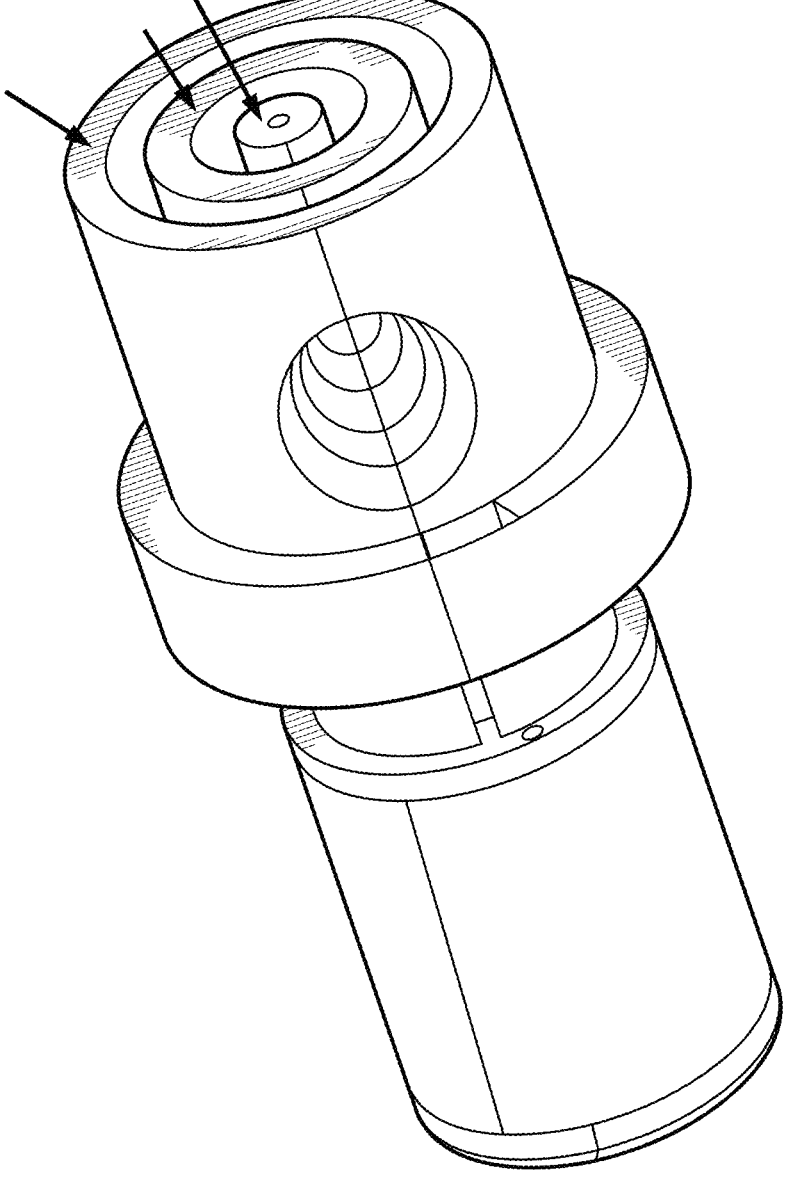

FIG. 26 shows a gear plate assembled in the cylindrical shell radiation shutter system with a motor showing three cylindrical shells (A, C, E from inner to outer). Not illustrated in order to demonstrate the principle involved are cylindrical shells B, D, and F. The arrows show the shells aligned with the aperture. Note in the gear drive beneath the gear plate is a slot just above the motor. This slot is a space for attachment of a mainspring which will rotate the gear plate counterclockwise rapidly in the event of a motor failure, closing the shutters as a fail-safe mechanism.

Figure 27:
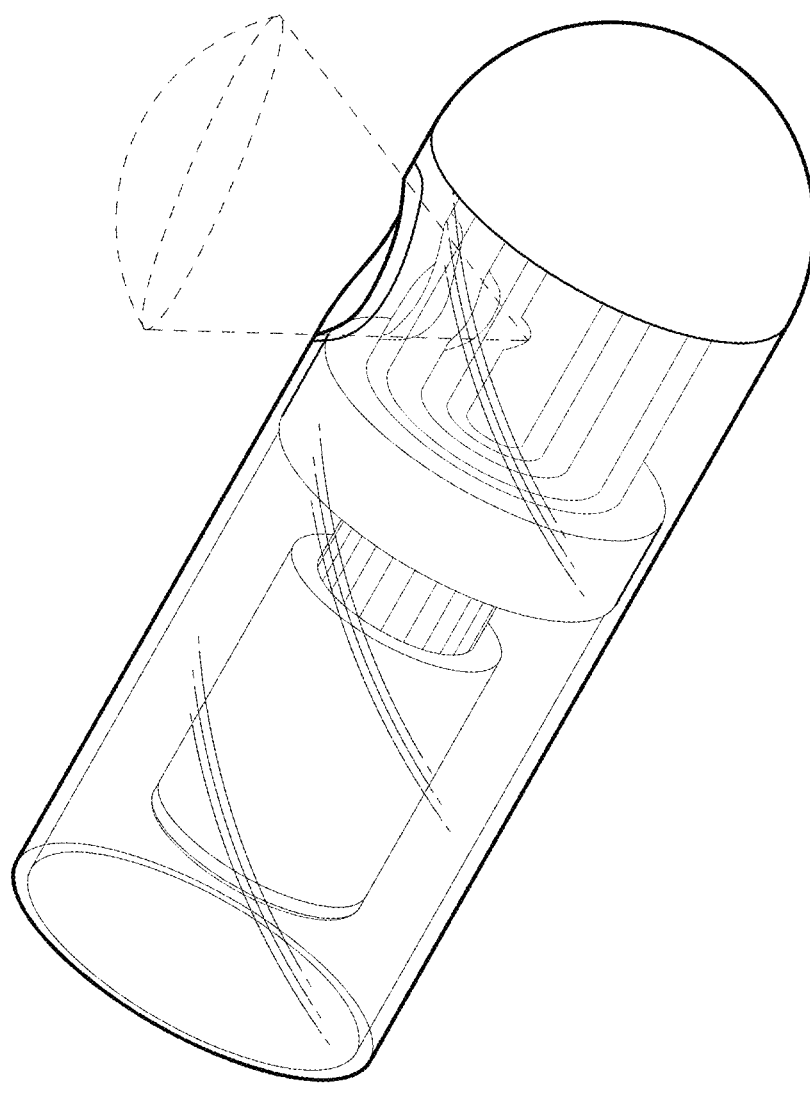

FIG. 27 shows a completed capsule with cylindrical shell radiation shutter system, gear plate and drive motor shown. The radiation source is at the very center of the aperture inside the inner most cylinder.

Figure 28:
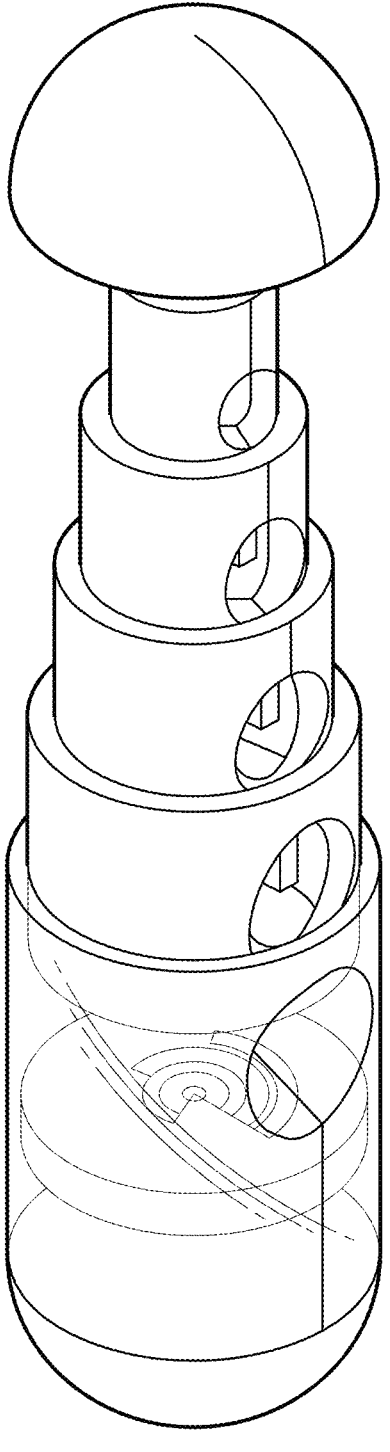

FIG. 28 shows an exploded view showing individual cylindrical shutters in alignment with radiation shielding caps in place top and bottom. The gear plate is visible below the shutters.

Figure 29:
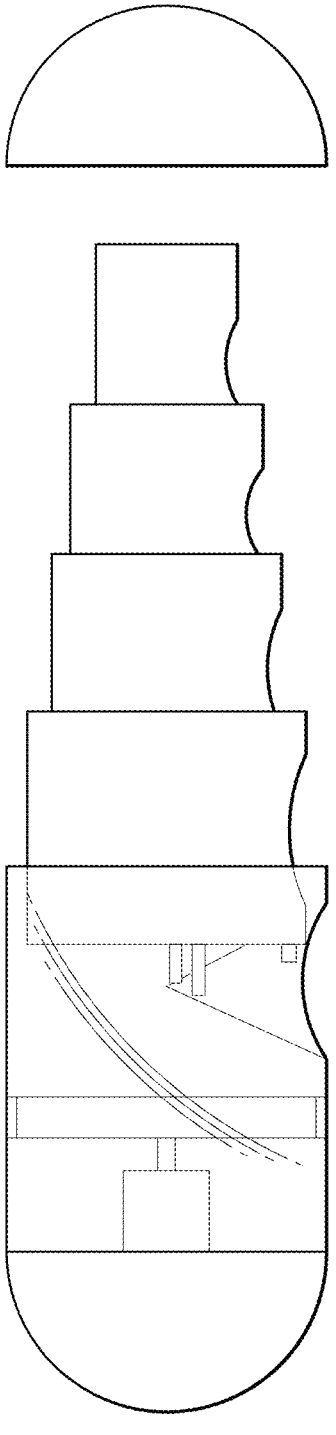

FIG. 29 shows a Side View of the exploded capsule containing the cylindrical shell radiation shutter system showing a) (toward the top) radiation shielding cap above and a radiation shielding cap below (toward the bottom of the figure), b) a Side view of the outermost emission aperture (beam port) and c) the individual cylindrical shutters with ports (apertures) facing right in this illustration.

Figure 30:
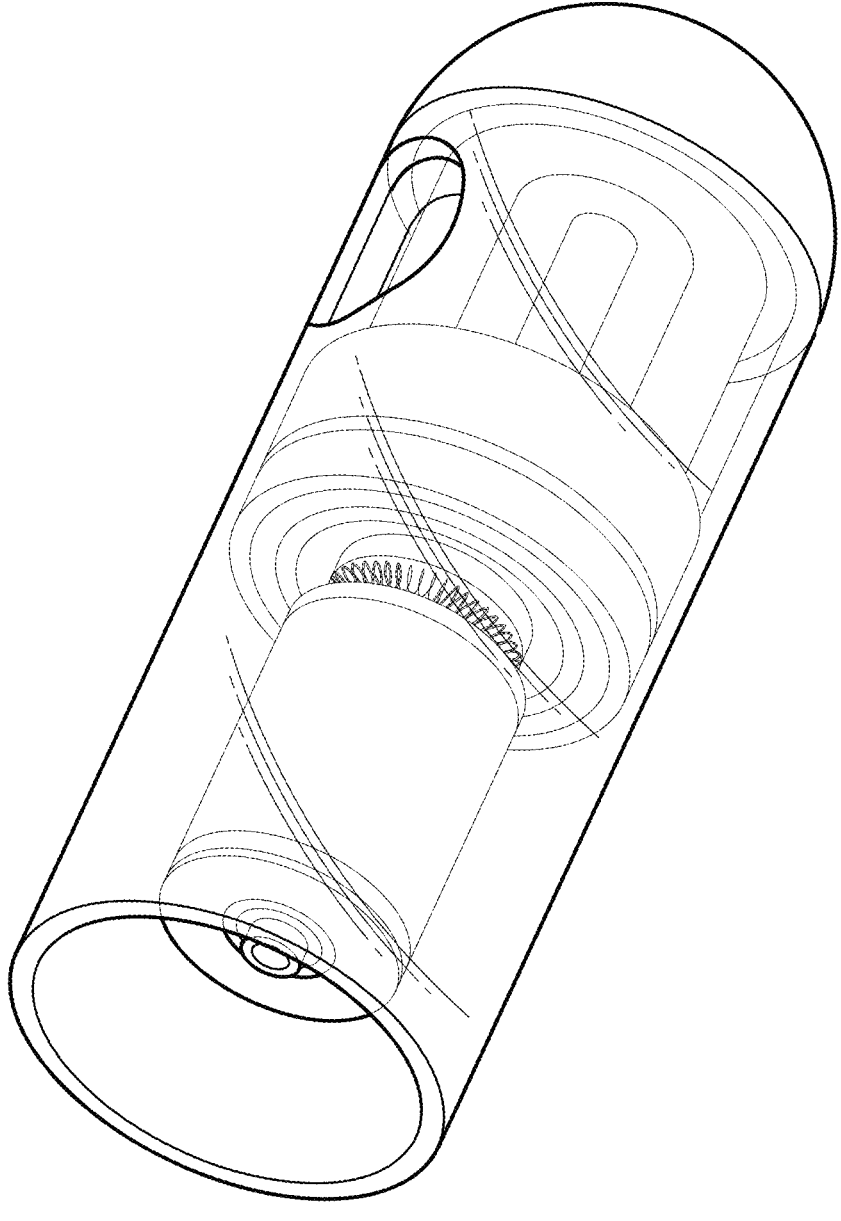

FIG. 30 shows a final assembled capsule with cylindrical shell radiation shutter system showing radiation shielding cap in place, cylindrical shutters (with every other cylinder removed for clarity, gear plate drive mechanism, drive motor, and a means for a fail-safe closed position, here a mainspring emergency fail safe closing mechanism located between the motor to the lower left of the figure and referred to in the description to FIG. 26.

Figure 31:
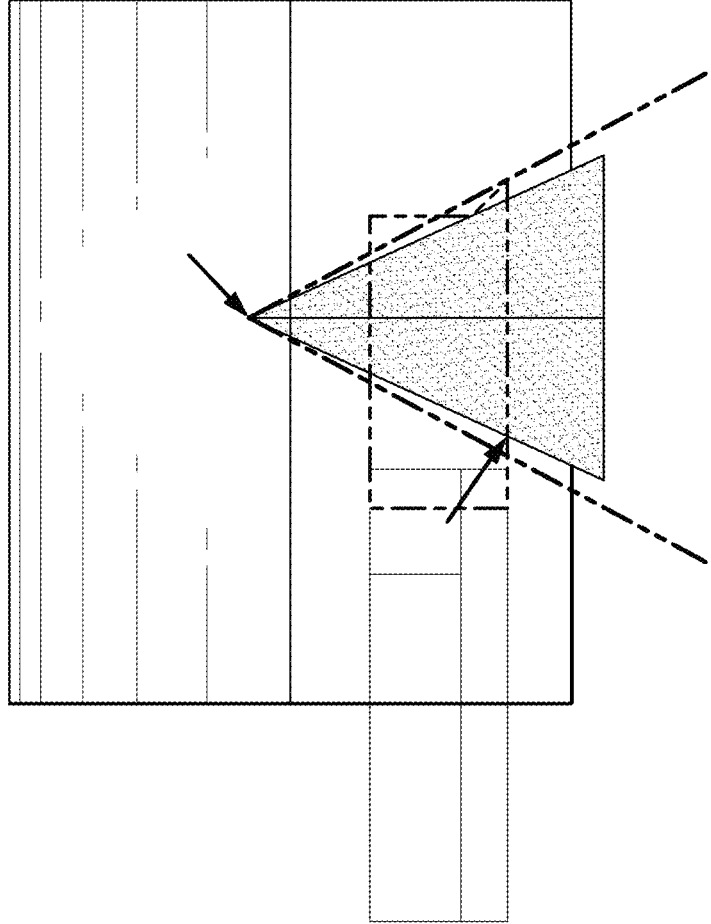

FIG. 31 shows a linear slide shutter assembly showing radiation source indicated by the arrow pointing to it, desired beam path (the shaded cone), shutter and area of shutter interference with desired beam path (shown by the box indicated by the dashed line of a dash and two dots), creating penumbra effect with variance in irradiation dose on the desired target in this region. The dashed line of a dash and two dots just outside of the shaded cone shows the radiation shield gap necessary to accommodate the sliding shutter permitting undesired exposure when the irradiation is in progress. Similarly, the gap between the shaded cone and the dashed line of a dash and two dots shows an air gap in the field permitting undesirable inhomogeneity in the radiation field. The figure illustrates the use in the present invention of a different set of elements and structure in order to achieve homogeneous solid angle divergence of beam port from the radiation source and virtually eliminate significant voids with minimal radiation attenuation in the voids.

Figure 32:
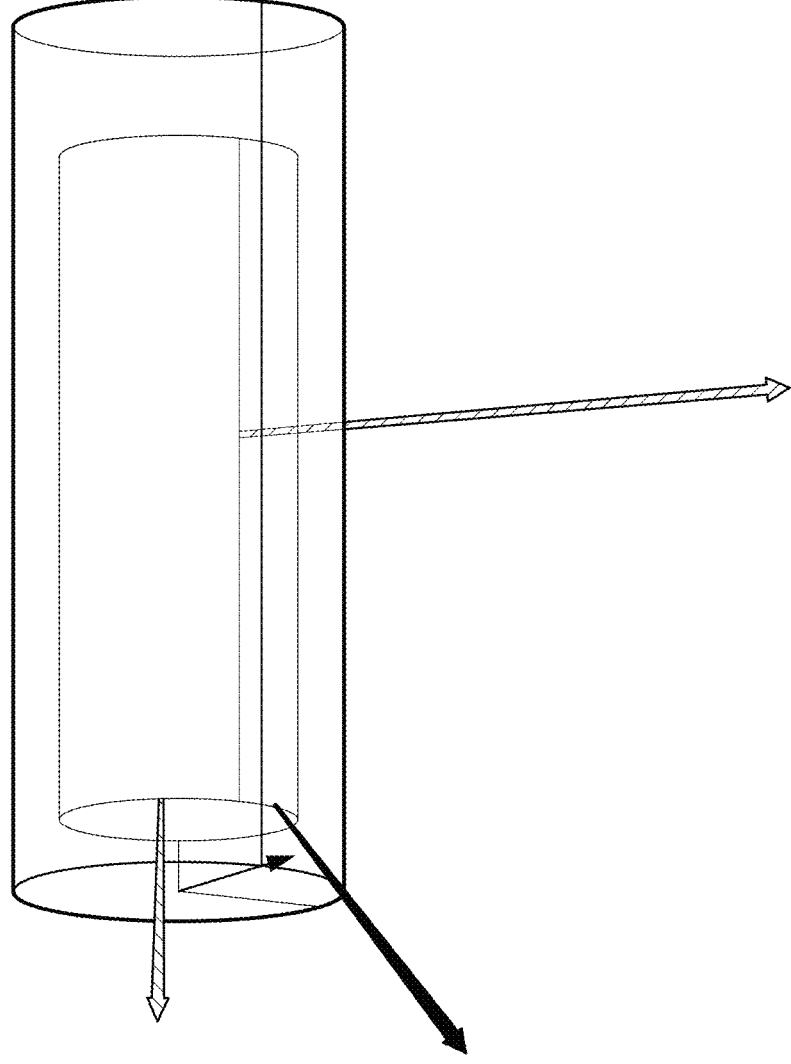

FIG. 32 shows the radiation source geometry. There are two pertinent geometries. The radiation source geometry is associated with the radiation source itself, and consists of a "capsule central axis" from which all pertinent radiation distances are measured (Distance is from the radiation source in this illustration, for the embodiment of emission from the long end of the capsule it is the radiation source as one end of the distance line). This is depicted by the yellow arrow. The green arrow shows an off axis ray, which is not on the central axis. Note this geometry may be the same as the physical geometry of the capsule, or if desired may be independent of the capsule geometry, depending on application requirements.

Figure 33:
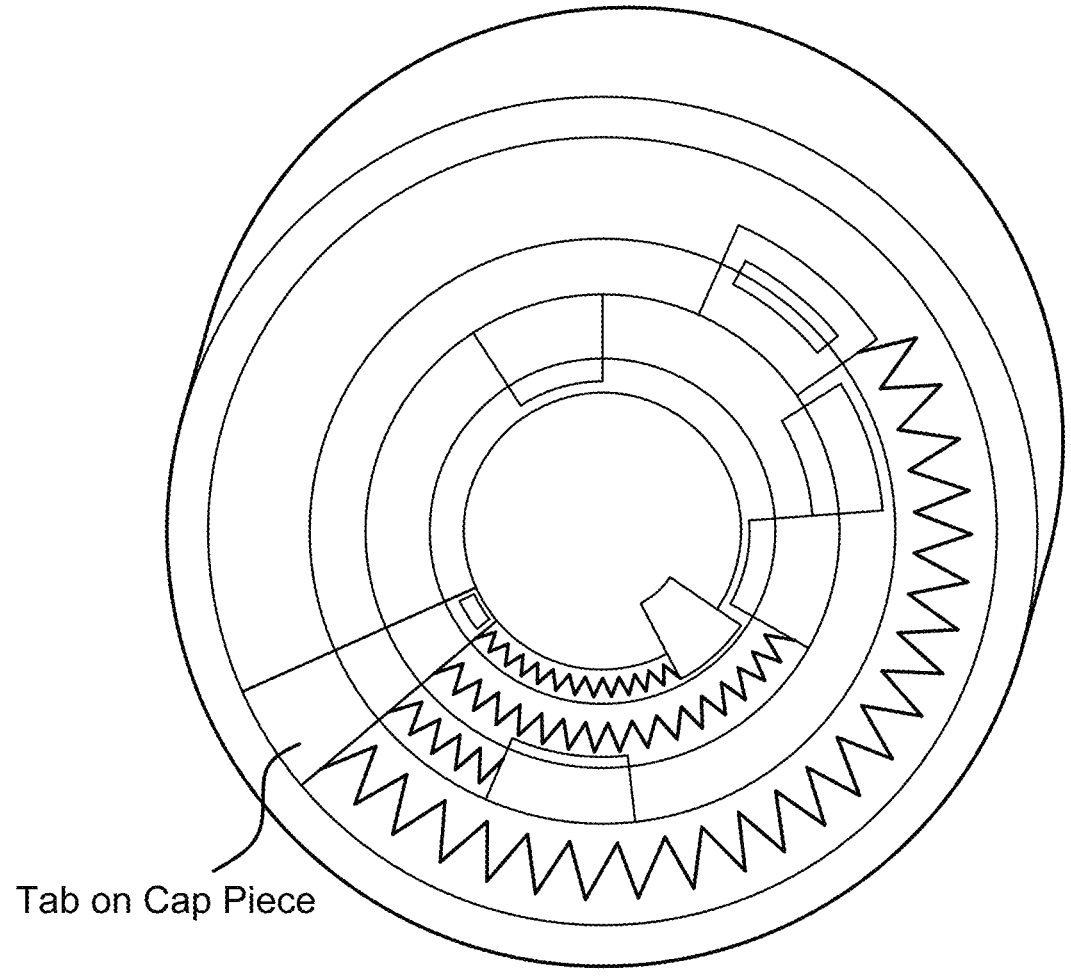
Figure 34:
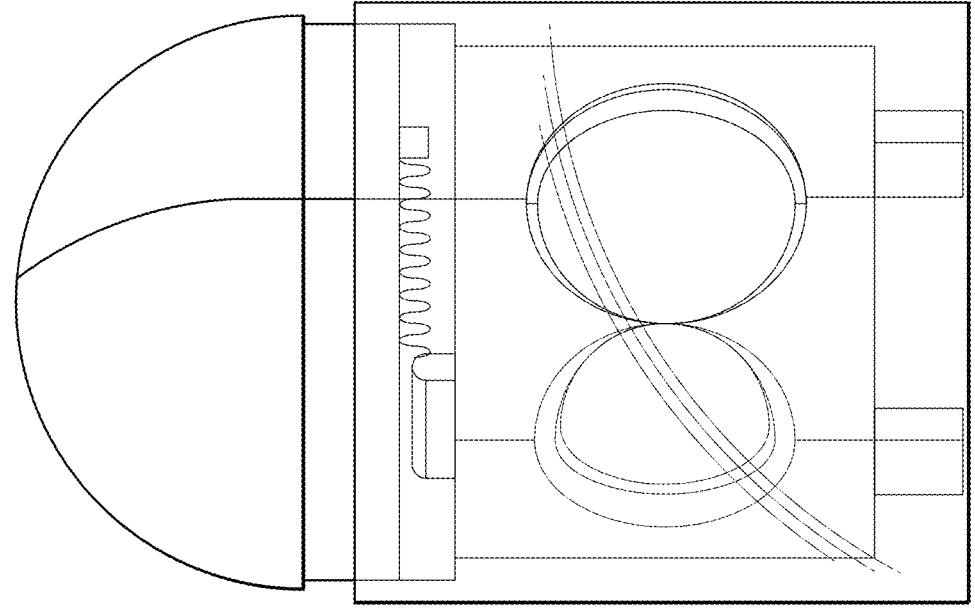

FIG. 33 shows a view along the capsule central axis of a means for a fail-safe closed position, here a coil-spring fail-safe mechanism FIG. 34 shows a view perpendicular to the capsule central axis of a coil-spring fail-safe mechanism engaged with respect to a tab, gear tooth or cam against a cooperating tab, gear tooth or cam such that if power is lost, the spring causes the particular shutter or shutters operated in cooperation with that particular shutter to occlude radiation.

Figure 35:
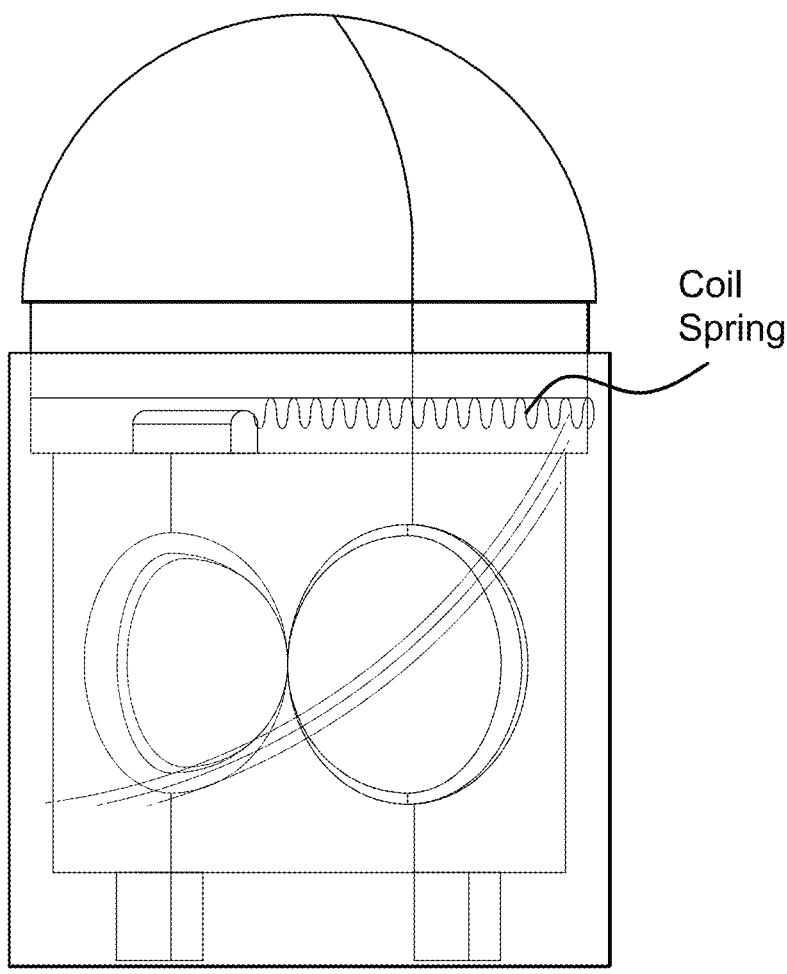

FIG. 35 shows another view of the internal disposition of a coil-spring fail-safe mechanism.

Figure 36:
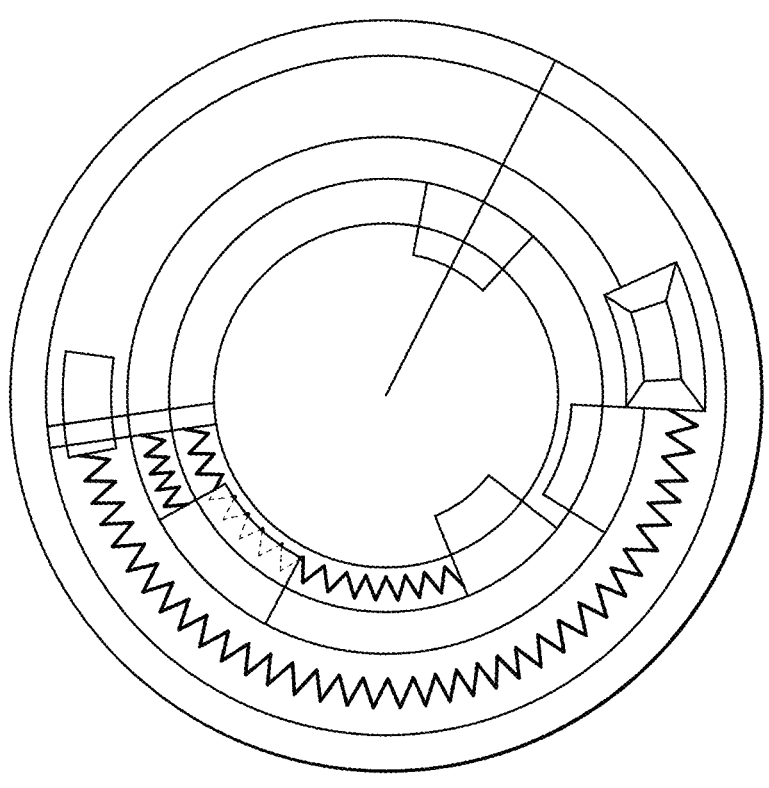

FIG. 36 shows a cross section of multiple coil-spring fail-safe mechanisms disposed in cooperation with a series of gear teeth or cams such that if power is lost, the spring causes the particular shutter or shutters operated in cooperation with that particular shutter to occlude radiation.

Figure 37:
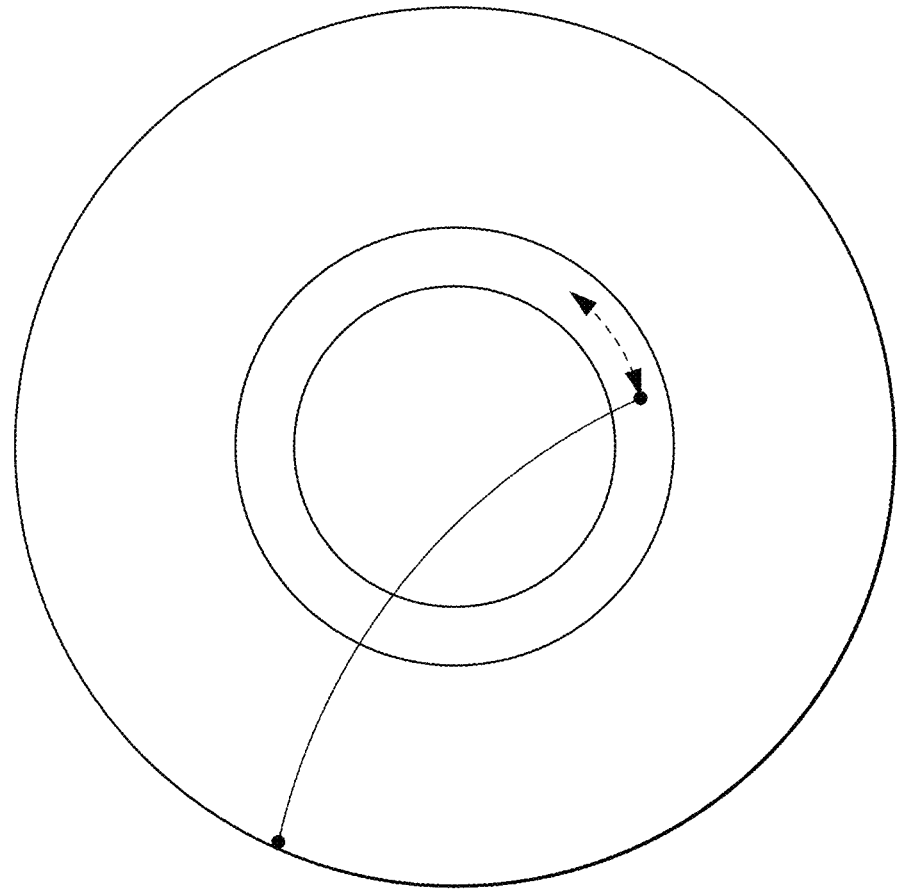

FIG. 37 shows a means for a fail-safe closed position, here a leaf-spring fail-safe mechanism which is connected to a sample cylindrical shell with the cylindrical shell being driven open by the operation of the capsule to align the shells and returning upon no longer being driven to a rest/fail-safe position.

Figure 38:
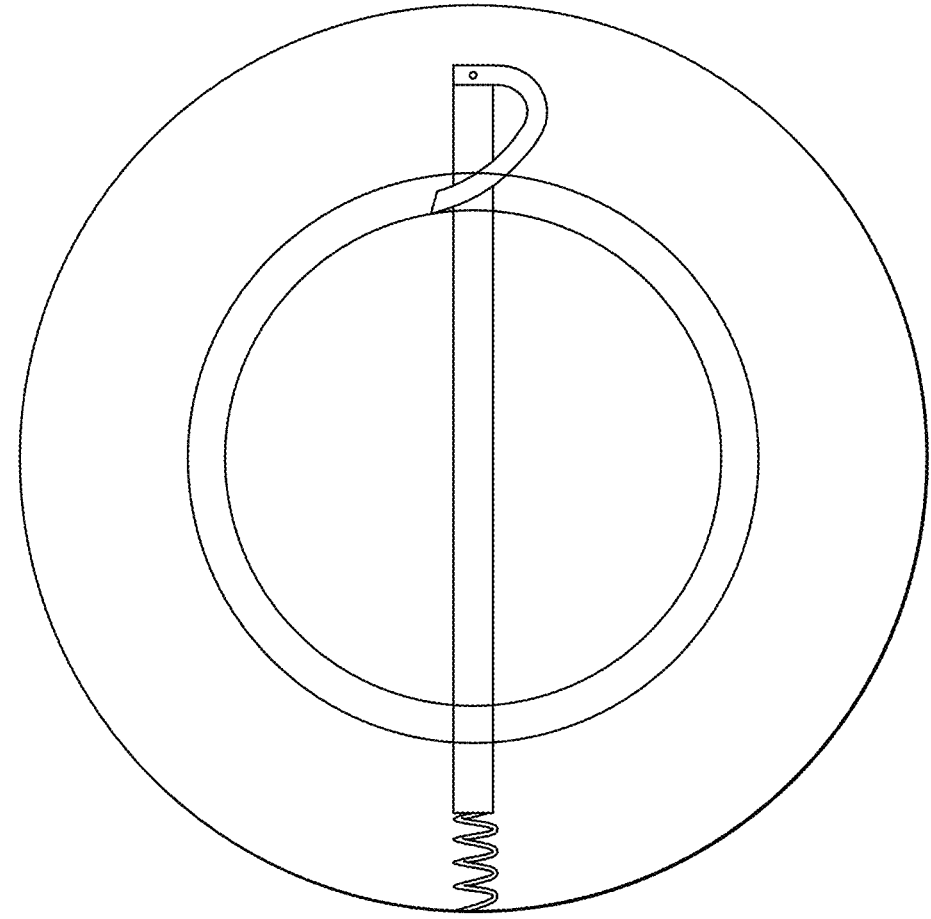

FIG. 38, shows a means for a fail-safe closed position, here a longitudinally acting spring operating a cantilevered arm which is connected to a sample cylindrical shell with the cylindrical shell being driven open by the operation of the capsule to align the shells and returning upon no longer being driven to a rest/fail-safe position.

FURTHER BACKGROUND

The effective undesired dose outside of the beam path which traverses necessary gaps in shielding material is given by the formula $I=I_0 e^{(-\mu x)}$ where $\mu$ is the mass attenuation coefficient and x is the total thickness of the shielding material (less air gaps). As can be seen in above the beam port in FIG. 15, an air gap must exist to accommodate closing the shutter, which reduces the shielding thickness with a consequent increase in undesired radiation leakage outside of the desired radiation field. Where x=0 (within the beam path, there is no attenuation from shielding. Where there are air gaps in the shutter the value of x is reduced by the path length of the air gap resulting in differing shielding attenuation, increasing undesired leakage and restricting the beam port shapes to those shapes easily mechanically accommodated.

Conversely, below the beam port, the shutter itself creates a variable air gap due to its physical characteristics, which will partially attenuate the beam causing a variance in beam intensity (penumbra) resulting in undesirable overdose/underdose at the field edge.

This leaves the following potential dose in-homogeneity:

Source to device surface distance along the mechanical discontinuity: 2.8 cm.

Shielding Available (shielding—mechanical space air gap): 1.4 cm

Which leaves a total shielding thickness of 2.8 cm–1.4 cm=1.4 cm

If a maximum typical exposure time is 75 minutes with an unshielded source of 177 cGy/minute, and lead is used in the device (for the purposes of this example), the tenth value layer (TVL) of lead is 0.6 cm.

$$\frac{(1.4 \text{ cm})}{(0.6 \text{ cm})} = 2.3 TVL$$

The resulting dose attenuation is:

$$177\frac{cGy}{\min}10^{-2.33} = 0.83\frac{cGy}{\min}$$

If there were no air gap at all in the shielding, the dose attenuation would be improved to $$\frac{(2.8 \text{ cm})}{(0.6 \text{ cm})} = 4.67 TVL$$

and the leakage will be reduced to $$177\frac{cGy}{\min}10^{-4.67} = 0.00378\frac{cGy}{\min}$$

Thus this air gap is significant and inhomogeneities in shielding can cause remarkable differences in radiation field doses. If a typical desired irradiation of 24 Gy is desired, the exposure time will be 24 Gy/1.77 Gy=14 min 6.6 seconds. The leakage from a shield with an air gap (discontinuous) will be 0.83 cGy/min×14.12 minutes=11.7 cGy. With a continuous shield the undesired exposure will be reduced to 0.05 cGy. This the elimination shielding discontinuities has a significant impact on reduction in unwanted radiation dose.

DESCRIPTION OF THE INVENTION

The preferred mode of invention proposes to first select an interchangeable irradiating capsule with a shutter as set forth below. Based on the depth and size of tissue to be treated, a radiation source will be selected for placement in the capsule and mounted on the robotic arm of the SRIORT. The arm would then be moved to the proper location for irradiation of the tissue, under direct visualization, with or without assistance from alternative imaging modalities or any combination of these.

Expanding on the above, the key invention components are:

A radiation source

A capsule mountable on an robot arm, or on an instrument connected to a robot arm, with an emission aperture opening to a cavity containing the radiation source with certain control electronics and devices designed to be connected to the surgical robot and inserted into the patient's body through the laparoscopic/surgical robotic incisions For a lesion, tumor, tissue, or organ, a mechanism for displaying pre-operative medical imaging, fused pre-operative medical imaging, including CT, MRI, Ultrasound, functional MRI, PET, PET/CT and nuclear medical scanning in the operating room in real time visible to the manipulation station of the surgical robot preferably on a video screen or computer monitor or other means for display.

A mechanism for identifying and tracking the real time coordinates of the radiation source capsule within the body and displaying the 3-dimensional location of the capsule on the pre-operative imaging with a projection of the presently programmed radiation field distribution on the images and a control means such as a general purpose computer to make real-time updates to the tissue position relative to the surgical robot, avoiding overdoses to desired tissue.

A mechanism for tracking, visually, preferably on a video screen, computer monitor, or means for display the internal position of the capsule within the body and for advancement and positioning under direct visualization using visible, infrared and ultraviolet light or any combination of these.

A mechanism for identifying the tumor, and tumor depth (using a combination of the above or ultrasonic echoes)

A mechanism for setting an aperture size, accepting a desired dose and calculating the exposure time based on the selected radiation source physical parameters and characteristics.

A mechanism for activating the now properly positioned radioactive source in the cavity to deliver the desired radiation dose, and field size and shape to the desired volume of the tumor while preventing exposure to the operating room personnel. Normally this would mean an electromechanical actuator opening a closed shutter in the capsule. However, a mechanical connection could be made so that an actuator, such as a pin, in the surgical robot arm actually activates the shutter to open. A spirally opening and closing iris shutter of the style used in a camera, or a simple door mechanism can provide an adjustable aperture.

A mechanism for identifying and tracking the real time coordinates of the radiation source capsule within the body and displaying the 3-dimensional location of the capsule on the pre-operative imaging, a post-radiation report to show radiation field distribution on the images, on for instance, a video screen, computer monitor or means for display, and probable damage to irradiated tissue.

These components and mechanisms will be described in detail below.

The application of the invention would be as follows for cancers:

The physician would have pre-imaged the patient's body according to standard medical procedures to locate the tumor and any other areas of suspected cancer activity, sometimes known as "hot spots". These are areas that are identifiable in a variety of medical imaging modalities, including PET, CT, MRI and nuclear medicine scans. The physicians would have visually identified any other areas of suspected cancer involvement during the course of surgical intervention.

The physician will then make an incision in the abdomen and the SRIORT is activated. The SRIORT has a television camera mounted on a robotic arm. The SRIORT has accessories mounted on a robotic arm and are controlled by remote control. The surgical SRIORT is then used to incise the interior membranes and a cutting implement is used to perform a resection by the physician. The surgeon can cauterize and clean as needed and ultimately view the remaining tissue through the camera on the SRIORT arm, and in conjunction with medical imaging as described above, determine what further areas need radiation treatment.

In the case of ovarian cancer, when the maximum surgical debulking possible has been obtained, frequently, studs of disease remain which involve the surface of the liver, the diaphragm and areas of the bowel. It is not possible to treat these areas generally with external beam (whole abdominal radiation therapy), conventional brachytherapy or loose isotope therapy or conventional intraoperative radiation therapy using accelerators due to the inability to deliver a precisely enough targeted and sufficient dose of radiation to eliminate cancer metastases without causing substantial morbidity and even mortality, or exposing operating room personnel to unacceptably high exposures to radiation.

Based on the depth of tissue desired to be penetrated and the desired dose to be delivered, a particular radiation source, which may be a radioisotope or device generated radiation (x-rays), of appropriate emission type, energy and strength would be selected for placement in the capsule on the SRIORT arm. This capsule would be either permanently mounted on the SRIORT arm or preferably would be an interchangeable module to accommodate differing physical characteristics of radiation sources. The capsule must be designed to balance size of the device with necessary shielding for both direction and size of radiation field and personnel protection from leakage radiation. The capsule would then be selected under robotic control from its storage location, mounted on the arm of the SRIORT and moved into the proper position inside the patient in the proper location for irradiation. The physician would then move the capsule and proposed beam location to the angle and desired beam angle to the lesion. The SRIORT has a camera enabling direct visualization of the lesion. An alternate imaging device, appropriate for the tumor could be used in addition to a camera, such as an ultrasound transducer or probe. A laser could be mounted to identify and illuminate the spot of radiation beam application.

Traditional TORT using linear accelerators external to the body have used doses in the range of 10-20 Gy (Gy=gray=joule/kg energy deposited in matter by ionizing radiation). These doses can be delivered with a variety of devices and isotopes, most commonly those with high specific activity such as Ir-192 or Cs-137, or more recently x-ray diodes and solid state x-ray generators, can be used. In addition, other emitters such as Sr-90 (beta emitter with energy of 0.195 MeV). The table below gives examples of byproduct material and typical energies and half-lives.

| Typical Isotope | Emission/Energy | Half Life |
|---|---|---|
| Cs-137 | Gamma/662 keV | 30 years |
| Ir-192 | Gamma/442 keV | 70.2 days |
| Sr-90 | Beta/195 keV | 29 years |
| Cf-252 | Neutron/fissile spectrum | 2.6 years |

Dose calculations are given by the following formula for isotopes:

$$\text{Dose} = (\Gamma_{AKR})(ISF)^2(\text{Strength})(timeofexposure)$$

Figure 1A:
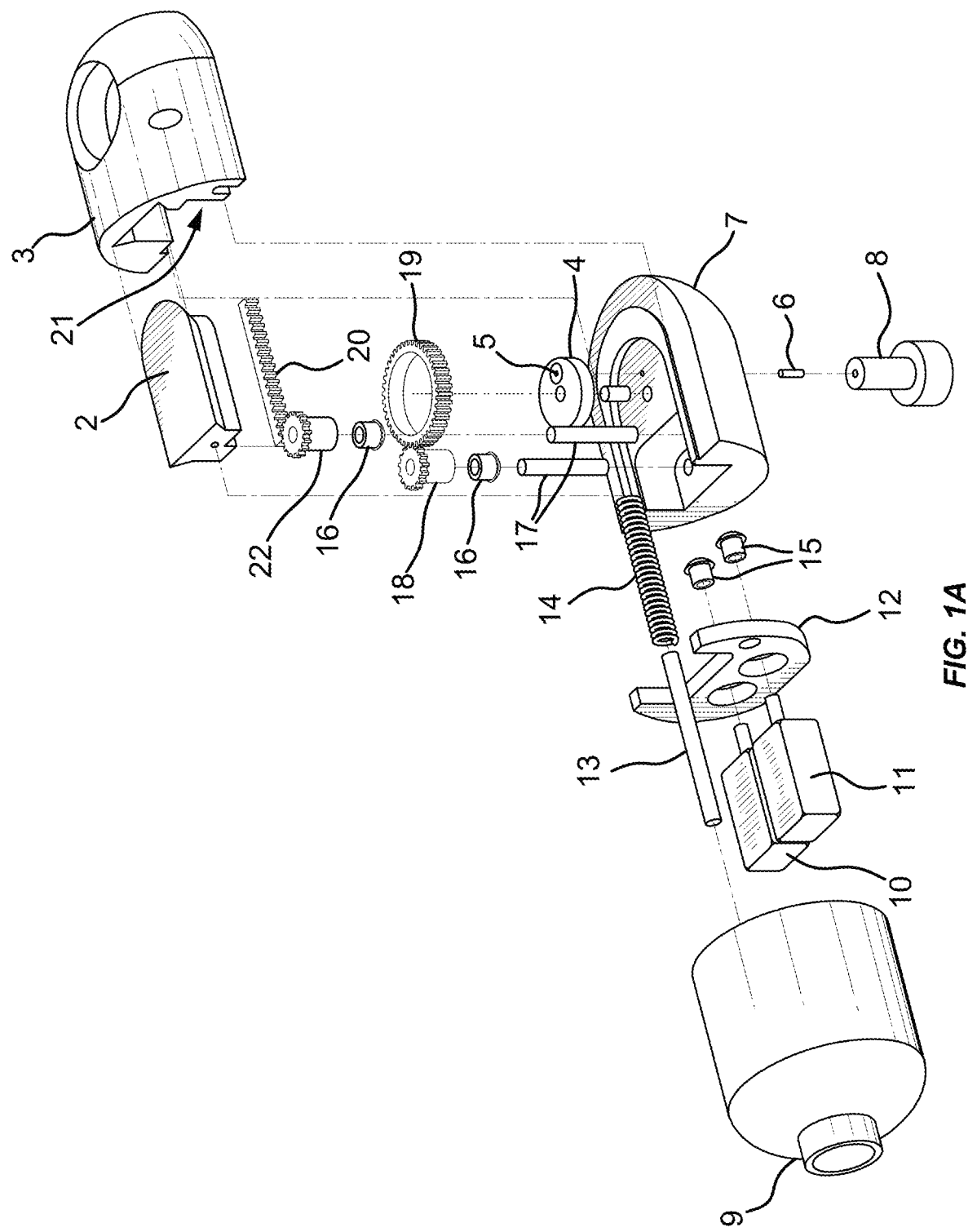
Figure 1B:
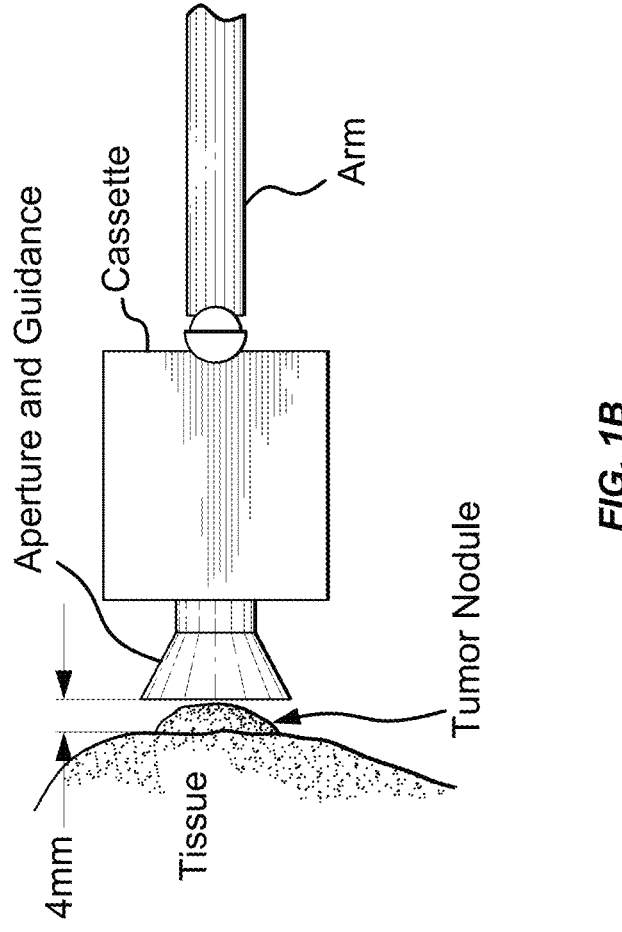
Figure 2:
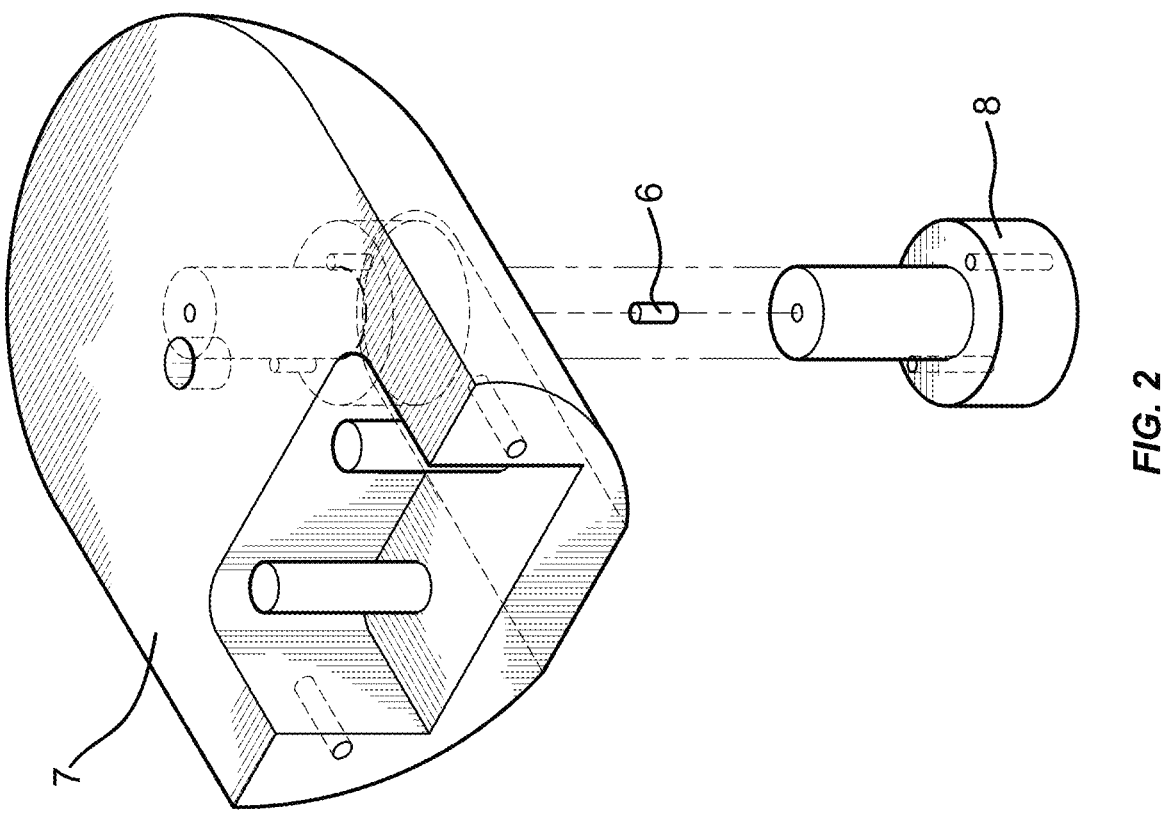
FIG. 2 shows the detail of radioisotope loading
Figure 4:
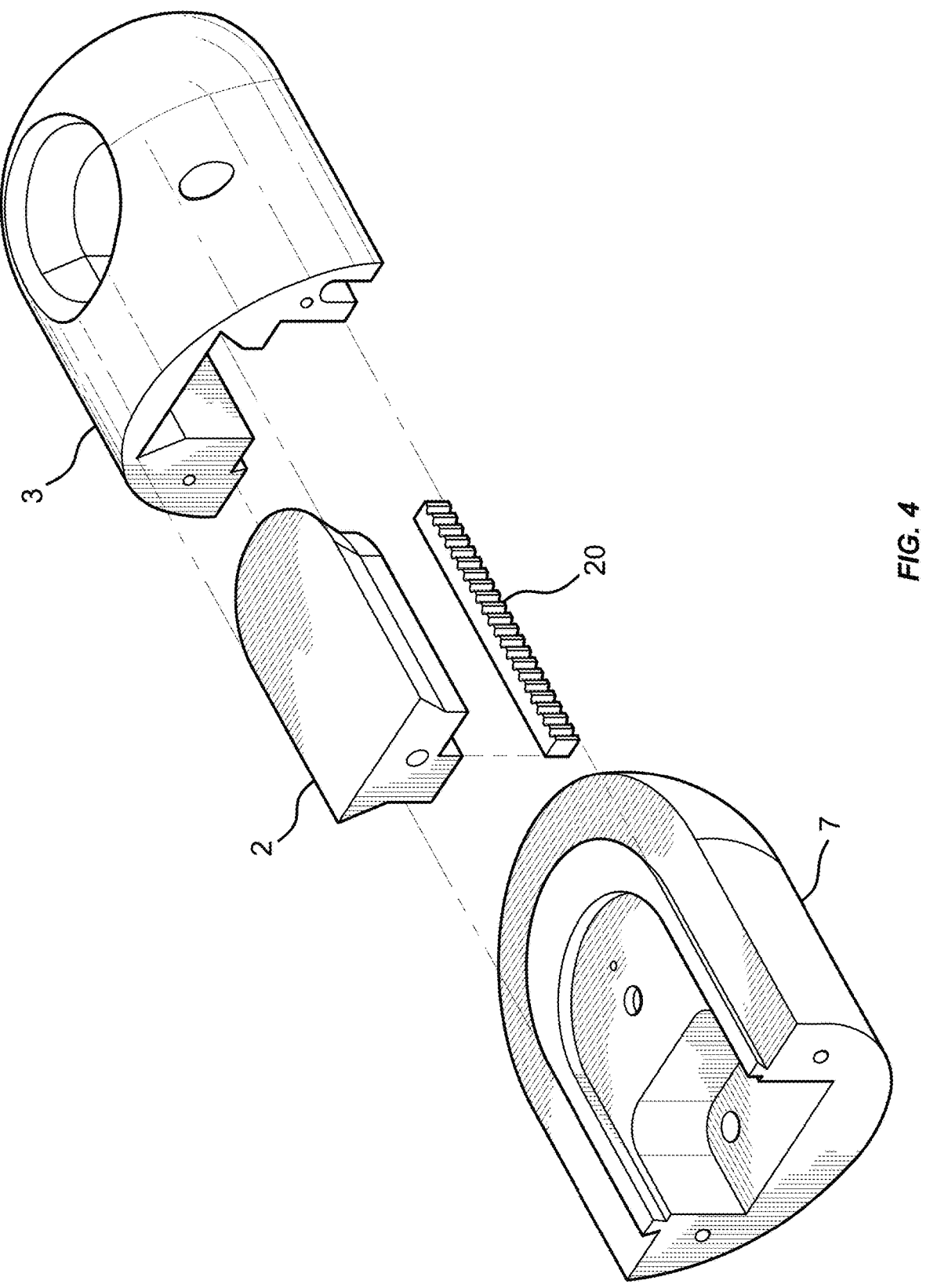
FIG. 4 shows the subassembly detail of the front mount and back mount and slide door and rack.
Figure 5:
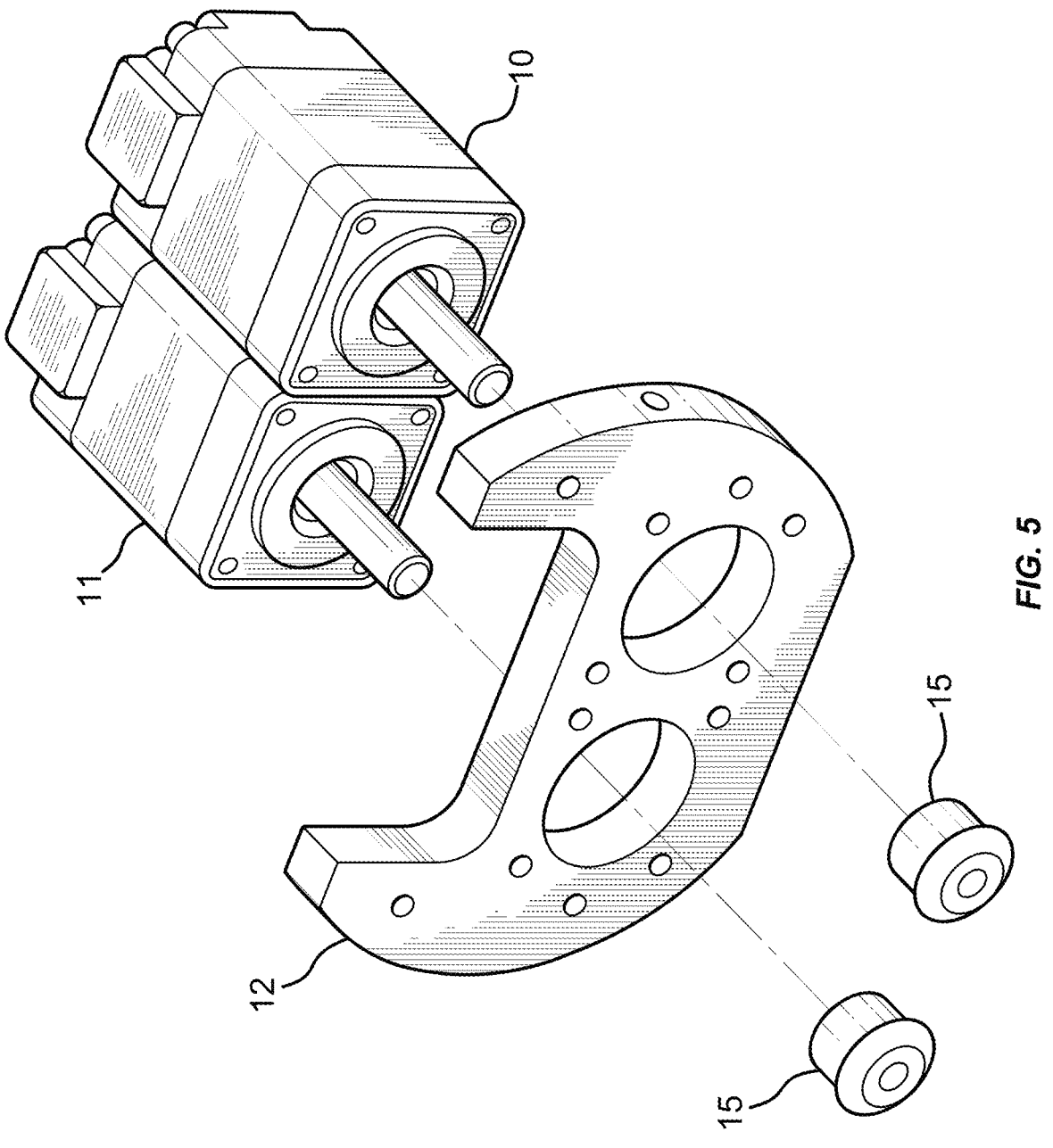
FIG. 5 shows the subassembly detail of the motor mounting plate relative to the stepper motors and the disposal of bevel gears on the shafts of the stepper motors.
Figure 6:
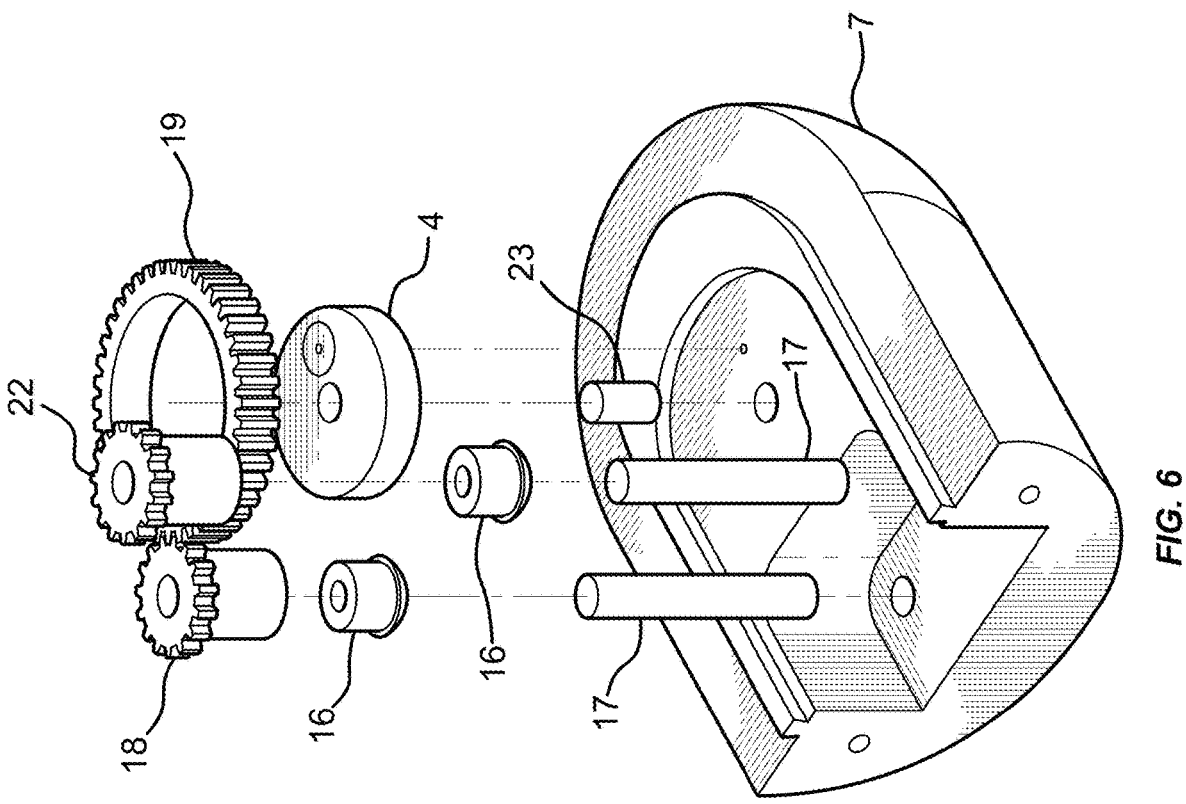
FIG. 6 shows the subassembly detail and relative positions of the spur gear and pinion spear gear, and bevel gears mounted on the shafts and the relative positions of the aperture spur gear and spur gear.
Figure 7:
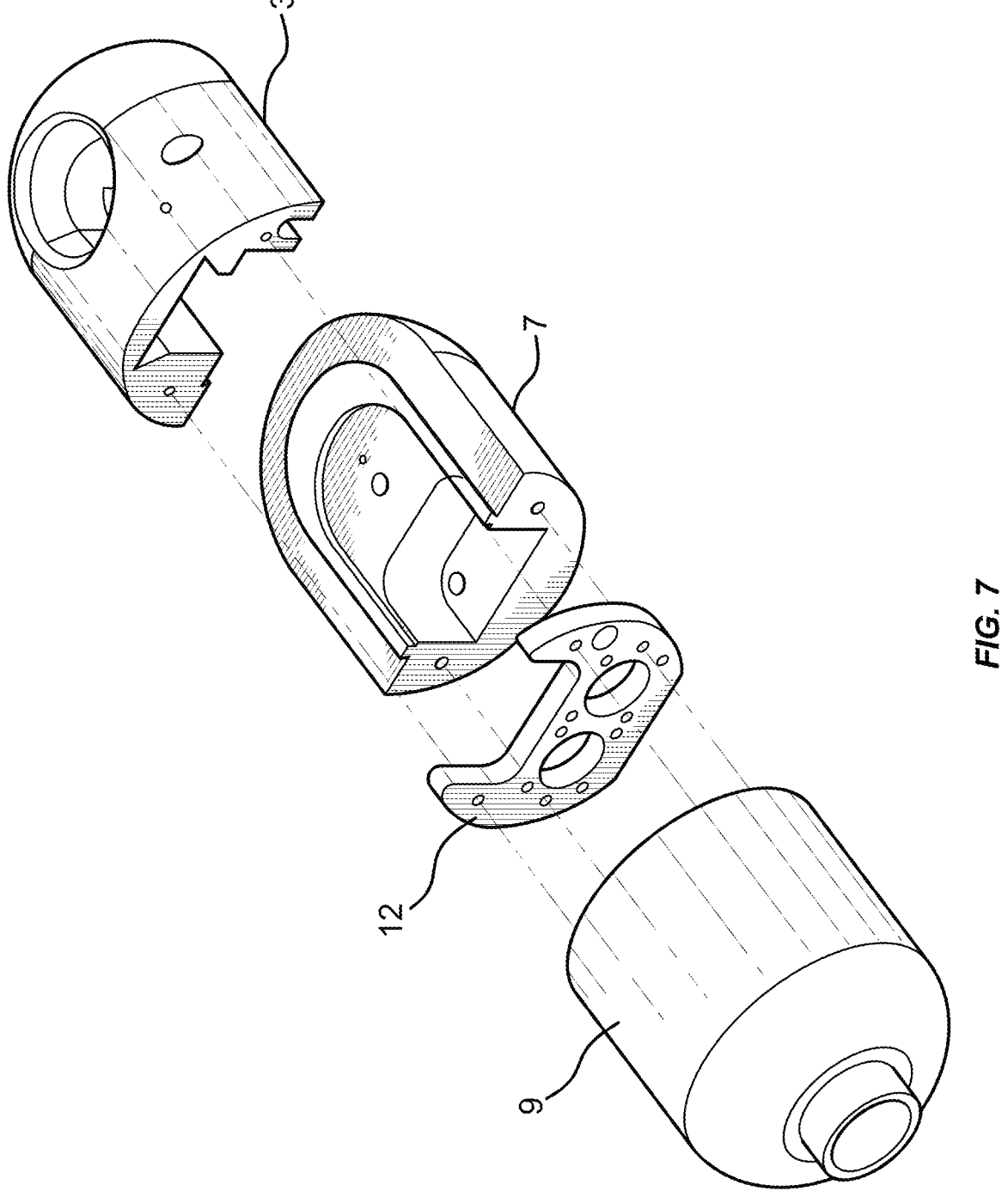
FIG. 7 shows the gross assembly detail of the end cap, motor mounting plate, front mount and back mount.
Figure 8:
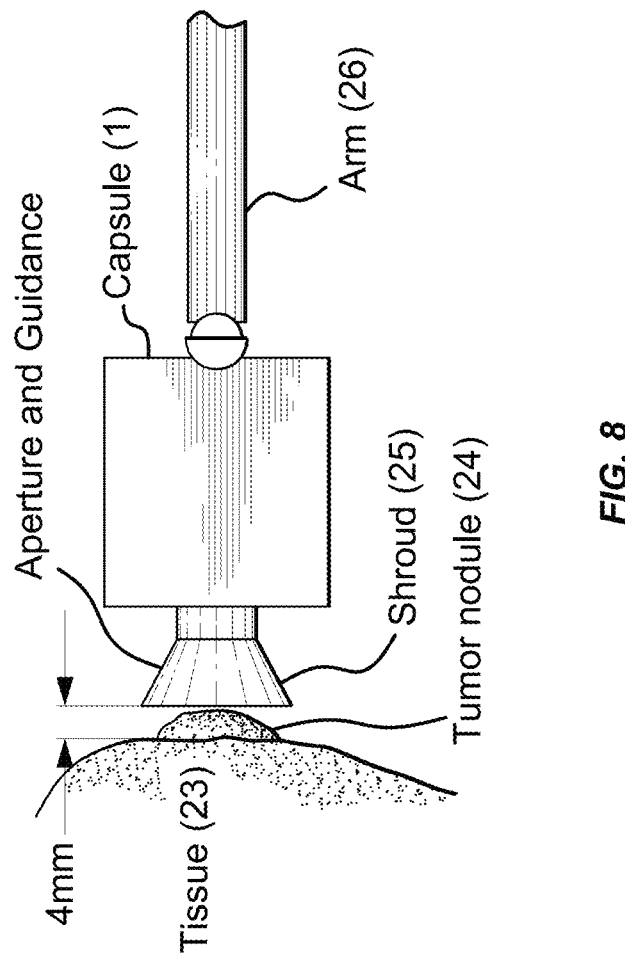
FIG. 8 shows another general concept and captures the overall concept of the invention.

These sources and other sources will generally have activity in the range of 5-10 Ci (10 Ci=370 GBq). For example, to deliver 20 Gy to a depth of 5 mm (4 mm+1 mm margin) for the 4 mm tumor shown in FIG. 1, from the applicator capsule, assuming a 10 Ci source strength, using Iridium-192, which has a specific air KERMA constant $$(\Gamma_{AKR} = \frac{(1.115\mu Gyxm^2)}{(GBqxhr)}$$

used to convert activity into dose, the following exposure would be required:

$$2000cGy = (370GBq)\frac{(111.5cGy - cm^2)}{(GBq - hr)}\left(\frac{1}{(0.25\ cm)}\right)^2\left(\frac{1\ hr}{60\ min}\right)t$$

which yields an exposure time of 2000/11001=0.181 minutes or 10 seconds exposure, assuming the above parameters. The quantity 0.25 cm. was selected in order to have a typical source to surface distance. Therefore, each lesion could be treated in under 1 minute, with precise control of exposures, field placement and size under real time guidance in the operating room using the SRIORT.

Due to the absolute criticality of distance in this exposure range, to delivered dose per unit time, the capsule will have an independent electronic distance measuring device using optical ranging.

Where organ motion is a concern, the device can be placed at an increased distance such as 0.5 cm from the tumor at the physician's discretion. Adjustments can be made to accommodate organ motion or relative motion of the patient. For this distance the above calculation would yield an exposure time of 0.67 minutes or 40.2 seconds.

The exposure time would be electronically controlled with a dual timer backup system whereby if the primary timer set time expires, then a backup secondary timer will engage and close the aperture to stop the radiation exposure. Both of these timers will have a clearly visual display at the operator's console with an alarm, both visual and audible when the cassette has radiation present and a second alarm both visual and audio if the cassette's control electronics fail to close the aperture (in the case of a radioactive source) or stop power to the radiation generator (in the case of an x-ray diode device).

The cassette's radiation "safe" chamber and aperture is constructed with radiation shielding in mind. Since the device is capable of using both high and low dose rate sources, shielding is mandatory for several reasons, the most important of which is to protect patient tissue from stray radiation emission from the device and to protect operating room personnel while the device or radiation source is in transit.

The shielding calculations are based on using either depleted uranium, lead or tungsten. Due to its superior shielding characteristics, the preferred shielding is uranium since uranium shielding will be thinner and allow for a more compact cassette which will be easier to insert into a laparoscopic wound (1-3 cm) and manipulate under robotic control, once it is inserted into the body. A typical source size (based on the Nucletron and Varian sources presently in use), is 0.5 mm in diameter by 5 mm long. To reduce the dose to acceptable levels during the time the source is in the patient, for this proposed calculation example, an assumption is made that a procedure with the source in the patient could last up to an hour. During this time the source will be emitting radiation and in the medical therapeutic use of radiation 60 cGy of exposure during a treatment can be administered at low risk. Since operating room personnel exposure must be kept lower than this, additional external shielding will be placed around the patient to meet ALARA radiation safety limits. The robotic workstation can be placed physically far from the patient, further minimizing the need for external shielding. The shielding calculation equation is $$10Cix\frac{37GBq}{Ci}x\frac{111.5cGy\ cm^2}{GBq - hr}\times\left(\frac{1}{10\ cm}\right)^2 = 412.55\ cGy/hr$$

The 10 Ci is selected as the source strength. The quantity 37GBq per Ci is a conversion factor. Ten centimeters is a typically selected distance to the patient body surface for the purpose of radiation shielding calculation because the average patient is approximately 20 cm. "thick." To reduce this dose rate to an acceptable level, the dose would be reduced to less than 60 cGy/hr or by a factor of approximately 1 or 2 tenth value layers of shielding. The tenth value layer of depleted uranium for Ir-192 is 6.5 mm so, 1.3 cm of depleted uranium will allow full shielding and reduce the leakage exposure rate at 10 cm from 411 cGy/hr to 4.1 cGy/hr at 10 cm or 16 cGy/hr at 5 cm. If tungsten were chosen, the shielding thickness required will be approximately 22 mm.

Given the source size, shielding requirements, and necessary electronics and adaptors, the preferred mode would be that the final dimensions of the cassette will be 4 cm in diameter×5 cm long or 4 cm×3 cm×5 cm. For the cone portion, if a cone is desired, the divergence of the cone should match the outer diameter of the tissue being irradiated. The cone can be selected in shape to correspond to the tumor shape. The cone can be very short, if used at all, 3 to 4 mm. The cassette can have varying cones mounted on it to conform to irregular tumor shapes. This will give adequate space to enclose a source, associated visualization, measurement and control electronics and mechanical safety apparatus. In SI units the shielding calculation equation is:

$$10Cix\frac{1000mCi}{Ci}x\frac{4.111cGy\ cm^2}{mCi - hr}\times\left(\frac{1}{10\ cm}\right)^2 = 411\ cGy/hr$$

The shutter would have a diameter of at least the maximum field size desired. A cassette designed with a shutter opening of up to two cm. would be the most that would likely be required. The collimation of the radiation is more likely determined by the size of the source, but the shutter size should be larger than the largest desired collimation for a particular treatment regime.

Another preferred mode is a slightly smaller capsule. Its shielding can be increased by leaving cavities in the capsule into which can be inserted tungsten or depleted uranium blocks or other very emission absorbing material. Those materials are very difficult to work or machine and are more easily used in pre formed shapes like blocks or sheets. If lead blocks are used and sealed in by relatively inert metals to body materials, or even sealed in by silicone or other material which does not give insult to body tissue or react with such tissue, this is a way to give lead functionality in the capsule as a shield which would otherwise be less desirable to insert in the body, even for a short time. Lead is easily worked and melted. By using those methods of shielding, less expensive shielding materials can be combined to lower the capsule cost.

A second mode of invention would use the cassette device as a positioning system only and for the delivery of radiation the device would have a transfer tube connector which would allow the use of existing High Dose Rate Remote afterloading devices such as the Nucletron HDR or Varian HDR device to provide the radiation source. These devices have an Ir-192 source similar to that described above which is attached to a cable and is positioned via transfer tubes which are attached to the HDR and the SRIORT cassette. This option would be available for institutions that have such a device available for interstitial radiotherapy. Other than the source delivery mechanism, in this case, the source is not an integrated part of the cassette, but rather delivered once the device is properly positioned. There are numerous disadvantages with this arrangement which make this less preferred than the self-contained system, most notably is that the source is freely radiating while it traverses the transfer tubes, which will require all personnel to leave the operating room, thus dramatically increasing the time it takes to do the procedures.

The advantage of this device is that the device is small, easily manipulated by the SRIORT control systems, in real time, under direct visualization. This enables the surgeon and radiation oncologist to determine during the course of the operation areas of residual and unresectable disease and to deliver a dose of radiation precisely and interactively to sterilize the tumor. Because the capsule radiation source is orders of magnitude smaller than the conventional linear accelerator arms, it can be placed with high precision within the body and using articulating robotic "hands" holding the capsule in place, the field can be directed at the correct tumor site while inserted into the body through the robotic incisions.

Due to the potentially high activity sources in use, an emergency aperture closing mechanism incorporating both electronic and mechanical overrides would be used in the device. The system will also have fail safe mechanisms resulting in the aperture defaulting to the closed position absent electrical and mechanical signals to open the shutter or expose the aperture. In the case of x-ray generators, the fail-safe will not permit current to flow to the device except under direct positive command.

In addition this device, by virtue of having a shielded capsule with a controllable aperture, together with the articulated robotic "wrist" or "hand" apparatus, allows precise positioning of the radiation source prior to opening the aperture and thus protecting normal tissue from radiation until the device is positioned and verified. This is a substantial advance over the current methods of applying intraoperative radiation therapy.

The purpose of using a shielded capsule is to minimize the damage to tissue while the capsule and the radiation source inside is in transit to the desired location. The capsule would be made of a high density shielding material such as lead, tungsten or uranium and the capsule would have a shutter covering an aperture through which radiation particles would be emitted. The shutter would also be of high density shielding material such as tungsten, but materials can be selected from those in the Berger & Seltzer handbook which contains data on mass energy attenuation coefficients sufficient to provide appropriate and necessary radiation protection. The capsule design will permit the adaptation of interchangeable shutters, much like the interchangeable lenses of a camera.

The interchangeable capsule would be stored in a shielded storage device, could be sterilized by steam or gas sterilization as is traditionally used in the operating room environment. The radiation source would be extracted from the storage pig, which is a larger, well shielded storage chamber used to transport and store radioactive source material, usually build of lead or tungsten, immediately adjacent to the patient in the operating room which will minimize the exposure of any personnel and the patient during the capsule transit time. It would be impractical to shield all gamma radiation from a source emitting gamma rays, but the distance allowed by the robotically assisted intraoperative radiation therapy applicator coupled with a reasonable amount of shielding would allow the device to be used while minimizing exposure to personnel to be in conformance with NCRP limits of exposures to radiation workers. The device will include adequate shielding in the form of mobile shielding units installed in the operating room to protect operating personnel in accordance with the ALARA—as low as reasonably achievable—philosophy of radiation protection and well below the accepted occupational exposure limits for the planned procedures. Survey instruments will be built into the apparatus and workstations to measure and record total in-room exposures. Mobile patient shielding would be available, depending on the radioisotope, to shield the patient, preferably with an aperture for the surgical entry site only so that any exposure of the patient is minimized. That mobile patient shielding could be in the form of one or a series of hooded containers such as lead shields on mobile casters, or a one or a series of lead aprons.

The cassette could be designed to either have contacts connected to internal wiring that meet control contacts on the robotic arm, or the internal wiring of the cassette can be connected by a wire harness to the robotic arm. An alternative preferred mode is a wireless control mechanism, but the level of ionizing radiation can be problematic.

For alpha or beta emitters, a lightweight capsule is possible. Under current technology a particle accelerator cannot be used for effective application of alpha particles, protons, electrons or light ions, which at energies useful therapeutically have a very short path length, but within that path length are devastating to the reproductive machinery of cancer cells (DNA and cellular ability to repair fractured DNA). Alpha particles and to a lesser extent, beta particles emitted from radioisotopes are readily obtained from a variety of isotopes, as are gamma rays. [Berger and Selzer, Attix]

Alpha particles are considered high linear energy transfer (LET) particles and deliver substantive damage to DNA in the form of double stranded DNA breaks, which are very difficult for cells to repair properly. Gamma rays, and x rays, in contrast are low LET particles and operate by the generation of radiolysis of water generating hydroxyl free radicals in the vicinity of DNA causing single strand and double stranded breaks following a linear-quadratic curve of cell survival v. dose, culminating in a loss of reproductive integrity of the cancer cells. Likewise beta particles, though low in linear energy transfer can cause double stranded breaks and destroy DNA through clusters of single stranded breaks which can be made permanent by oxygen fixation in non-hypoxic environments.

The capsule mounted on the SRIORT arm enables an alpha or beta emitter to be completely shielded from healthy tissue and to minimize transient damage as the radiation source is positioned at its intended target. Only on setting the aperture to the desired beam size, positioning the aperture in the correct location and desired angle and opening the shutter on the capsule will a beam of radiation be emitted through the aperture in the capsule in the desired direction to irradiate the lesion. In the case of an x-ray generator, the x-ray source will only be turned on when the above parameters are met.

As particle path length in tissue is very predictable, cancerous tissue can be destroyed with a much finer precision while minimizing damage to normal tissue, such as livers, kidneys and bowel. Sr-90 is a typical beta emitter which would be deadly to tissue without appropriate shielding, but when used in the proposed capsule could be safely directed to the targeted area. Likewise isotopes that emit alpha particles, and gamma rays or a source capable of developing x-rays can be used with appropriate shielding design on the capsule. The significant advantage of a beta emitter is enablement by the invention of a new technology of a very effective and predictable radiating isotope, and the miniaturization of the capsule because of reduction of bulk because shielding is much simpler. Any metal, or plastic such as lucite, with appropriate electron stopping power as set out in tables for a source available to a reasonably skilled practitioner, such as the tables in Berger & Seltzer, can be used for the shielding. Much smaller tumors in much smaller and confined spaces can be treated.

The capsule shutter could be simply the equivalent of a door occluding a radiation aperture. A preferred mode is to use an iris type aperture with a clam shell outer cover. The aperture can be opened to various diameters allowing the physician to choose the size of lesion to be treated and the surface area of the volume. A light source can be disposed on the exterior of the cassette for illumination inside the patient of the tumor to be irradiated. An alternate light source to act a as field light behind the aperture through which radiation will be emitted, but behind the iris would enable the physician to continue visible inspection of a lesion as he positions the device for maximum coverage of the tumor before the radiation source is opened by the clamshell. In addition, this mode gives redundant protection should one or the other of the apertures fail while the device is in place, thus allowing the device to be removed from the patient and safely deposited in the shielded pig until repairs can safely be made. A preferred light source is an LED, fiber-optic or solid state light emitter.

Upon completion of the treatment procedures, the SRI-ORT arm and radiation source can be remotely stored in the pig or appropriate storage device where sterilization and preparation for the next case can take place. For convenience sake, the storage device is preferably a table with a shielding container or pig on it. The storage device would likely have multiple pigs. The storage device including a shielding pig is referred to as a shielded source containment table, even if a closet or storage cabinet is used. To insure radiologic safety, each pig shall have a means of detecting radiation presence to insure that a source is present or absent from the pig. By regulation, that would usually be a room detector in the room, and/or a sensor inside the shielded source containment table, such as an ion chamber, electrometer or Geiger-Mueller type device.

In addition to a radiation source, other devices could also be mounted with the unit, including a laser or particle emission device and used adjuvantly for tissue destruction. This device is not limited to the carriage of radioactive sources, but can also be used in conjunction with x-ray diodes or other radiation sources.

Because a surgical robot can have more than one arm, the invention enables more than one capsule to stand ready in the shielded source containment table so that should a physician determine to select a different capsule during irradiation, the capsule in present use can be quickly withdrawn, its path of extraction memorized and an new capsule with the preferred radiation source inserted.

Another important variation on the preferred mode relates to the doors or shutters on the capsule (also referred to as a cassette). The electromechanical movement could also be accomplished by hydraulic means with push pull pressure by an electrical signal to start a pump and then the mechanical action of pumping fluid to move a door. More specifically, a small hydraulic pump could be used to move the shutter or door, and a valve or a second pump used to move the shutter or door back. Also, the doors could be operated against non-toxic gas pressure so that when pressure is applied by a motor or hydraulically, in the event of power loss, the door moves to the closed position because the gas presses against the lost pressure.

The robotic system could be designed to combine the elements into an invention as before except that the non-radiation emitting features and associated control of emissions are separable from the radiation emitting features and associated control of emissions. By the expression "associated control of emissions" is meant the one or more doors or shutters on the capsule containing the radioisotope. As further description, on an effector arm or robot arm, or attachable to it, there would be a standard set of tools and carrier that would be used repeatedly. That will be referred to as the shuttle capsule holder. The capsule holding the radioactive source would be designed with necessary interconnects to control the doors to the shuttle capsule holder.

On the shuttle capsule holder could be other apparatus including tracking apparatus, range finders, laser pointer or camera/visualization apparatus. More specifically, those could be a stand-off remote detection for determining the distance from the radiation source to the tissue being irradiated, an electronic distance measuring device using optical ranging for locating the distance between said tissue being irradiated and said radioactive source, a means for utilizing ultrasonic detection to determine tissue depth, including tumor depth to determine an applicable margin to be irradiated, and one or more means for direct visualization by remote display of tissue adjacent to said capsule, which could be simply a fiber optic cable to transmit the image to an extra corporal screen or image capture device to see the image. The advantage of the direct visualization by remote means of tissue adjacent to said capsule is to ascertain if all diseased tissue has been surgically removed and to ascertain if further irradiation is necessary.

The procedure would be that the shuttle capsule holder would be set up by a technician and could have a range finder, light or laser pointer and other features pointed in U.S. Appl. 60/973,545, and 61/098,225 and PCT Appl. PCT/US2008/077100 entitled "DIRECT VISUALIZATION ROBOTIC INTRA-OPERATIVE RADIATION THERAPY APPLICATOR DEVICE." That shuttle capsule holder would be mounted to the robot, or picked up by the robot, and then remotely carried to the capsule for interconnection and then the dual system inserted into the body for treatment. Among the advantages are that capsule sizes can be smaller depending on which isotope/energy/emitter is selected and/or it enables tighter procedures and the shuttle capsule system allows reuse of the expensive components more easily.

Advantages of this system include the ability to use the more expensive parts repeatedly and to vary the capsules more easily. Capsules can be varied in size or protection depending on the isotope involved and perhaps the size of the incision. Also, the capsule can be shipped alone to a laboratory or radiopharmacy for reloading. The pig in which the capsule is stored could be shipped, the capsule filled with the hot radioisotope, and the pig returned to the hospital or surgical center to be opened by a robot and the operation to proceed as described.

The radioisotope can be mounted in the capsule any number of ways including gluing it on a pin in the capsule, or holding it in a ring like a circular gunsight or by otherwise securing it inside the capsule. The location should be secure and it is preferable it be known or measured because it is preferable to know where the radioisotope is exactly compared to the tumor being ablated. The size of the isotope varies in size and activity. Generally the order of magnitude is between 5-10 mm. For special purposes isotopes it may larger or smaller.

Another way of accomplishing the pickup of the capsule by a robot arm is to design the capsule so that it has a spine of contacts on it. Preferably to the rear of the capsule opposite the opening through which the radioisotope is exposed would be a group of contacts for electrical connection and any fiberoptic connection. Mounting them on a spine appears to be the easiest mode. The robot arm would have on its end a corresponding set of contacts and any fiberoptic connection interior to an alternately opening and closing jaw, and the jaw would be mounted on and then maneuvered on the robot arm or end effector to align the jaw's contacts with the group of contacts on the rear of the capsule and be closed on the contacts to make positive contact. The jaw could also be designed to be the shuttle capsule holder referred to before and/or to accomplish its functions. The jaw could be designed "inside out" particularly in the shuttle capsule holder design to have the contacts aligned inside a slot or aperture in the capsule into which is fitted a jaw which has the contacts on its exterior and is expanded to make positive contact. The jaw would preferably have material for attenuating radiation emissions similar to that of the capsule in order to preserve a relatively uniform radius of radiation attenuating material around the radioisotope.

Another preferred mode is to design a capsule in which is disposed a plunger. This mode would hold a "loose isotope", i.e. an unsealed radioactive source, in solution or in a form that is injectable into the tumor with a plunger from inside the capsule, enabling the use of a "hotter" isotope. This could be used with P-32 or I-131 or alpha or beta emitters, including Y-90.

EXAMPLES OF APPLICATIONS OF PREFERRED MODE OF INVENTION

In the following two examples, a narrative description of how the SRIORT device and system will be used in actual practice. Several physicians will, of necessity be directly involved in these procedures due to the differences in training between the specialties. The key players in each case will be a surgeon and a radiation oncologist. The surgeon will be specifically trained in a pertinent area and the radiation oncologist is trained in the appropriate use, application and dosing of radiation for the treatment of tumors. In addition, a medical physicist, specifically trained in the use of radiation sources in conjunction with the radiation oncologist, must be available for the planning of radiation delivery using the SRIORT device.

Example: Abdominal Tumor (Ovarian Cancer Stage IIIb)

Initially, the patient will be informed of the nature of the procedures to be performed in the treatment of the cancer. After being informed and after the patient acknowledges this information and gives her consent, the patient will be taken to the operating room and placed on the operating table in the supine position. Following this the patient will be anesthetized using general anesthesia supplied by the anesthesiologist.

After adequate general anesthesia is instilled, the patient will be examined under anesthesia to determine, if possible, the extent of disease. Following this, the patient will be prepped and draped in the usual sterile fashion and a sub-umbilical transverse incision will be made extending approximately 1-1.5 cm. Following this, a laparoscopic trochar with a TV camera in the bore will be advanced through the incision and under direct visualization into the peritoneal cavity. Following entry into the abdomen, the abdomen will be insufflated with carbon dioxide gas to distend the abdominal wall away from the intra-abdominal organs. Following this, again under direct visualization via the TV camera, a series of similar incisions will be made and trochars introduced into the abdomen which will allow the placement of robotic arms in the course of the surgery. Once these trochars are in place, the robotic actuating system will be placed into position at the operating table and the robotic arms will be placed in the ready position. The physicians will then move to the SRIORT control station, which will be located in the operating room behind a radiation shield of sufficient physical characteristics to provide as low as reasonably achievable radiation protection during the period of time that the intra-operative radiation device is in operation. The workstation will have visualization system originating from the robotic cameras placed in the patient, and selectable views. The control station will also have ergonomic robotic hand manipulators which will allow the physicians to move and manipulate the robotic arms in a natural way, under the control of computer and associated electronic circuitry.

The surgeon will then place the appropriate robotic arms into the patient via the previously placed trochars which will then be manipulated from the control station to perform the operation. The surgeon will generally use the robotic arms to place suction into areas of peritoneal fluid collections which will be sent to pathology for microscopic analysis for metastatic cancer cells. Following this, the abdomen will be washed with sterile water and that too will be collected and sent to pathology for analysis.

From this point, the surgeon will perform the hysterectomy, bilateral salpingo-oopherectomy and pelvic and para-aortic lymph node dissections. Once this part of the procedure is complete, the surgeon will turn his attention to the remainder of the abdomen. Generally in locally advanced ovarian cancer, the omentum is also removed. Following this, the surgeon will inspect the remainder of the bowel using the robotic devices and cameras for further evidence of cancer. S/he will examine the bladder, rectum, bowel, peritoneal surfaces, the liver and the underside of the diaphragm. If lesions are found, the surgeon will resect, to the greatest extent possible, any visible disease within the peritoneum, using the robotic surgery system. During the debulking process, the surgeon using the SRIORT system will activate a marking device which will record the spatial coordinates of all sites of known or suspected cancer that has been identified and/or resected within the abdomen or surgical field. These coordinates will then be available to identify, post-operatively and in future procedures, potential locations where further radiation therapy might be considered for the treatment of microscopic disease.

The marking device will consist of an electronic control which will signal the control computers to record the present spatial position and settings of the robotic arm, viewing system and controls to, in essence, create a stored anatomical "waypoint" allowing the surgeon to select the location at some point in the future, display the waypoint on the operating room imaging monitors either alone or overlaid on the pre-operative imaging. This will allow the surgeon and the radiation oncologist to return to the area of interest in the patient for further study, irradiation or procedures. In addition, the device will allow the surgeon to place a gold seed marker in tissue to identify the suspect tissue radiologically at a future point, post-operatively. Adjustments could be made to waypoints during surgery to accommodate changes in position.

Once the surgeon has completed his work, the radiation oncologist, in cooperation with the surgeon will place on monitors in the operating theatre the pre-operative medical imaging, including, but not limited to computed tomography scans (CT/CAT), positron emission tomography scans (PET or PET/CT), magnetic resonance imaging scans (MRI), ultrasonic imaging and any other imaging techniques which may be helpful in localizing position and radiation within the patient. Once the surgeon and the radiation oncologist determine the sites to be irradiated, the radiation oncologist, in consultation with the medical physicist, the shielding equipment will be moved into place in the operating theatre to protect personnel necessary to the operation from the radiation sources used in the treatment of the lesions.

Following this, a cart containing the SRIORT robotic applicator arms capable of attaching cassettes containing the radiation sources, along with the cassettes and radiation sources will be brought into the operating theatre.

Once the radiation oncologist has selected the appropriate radiation sources and doses to be used in the treatment of lesions, the medical physicist will pre-program the SRIORT device using a separate computer workstation to identify the sources to be used, the beam size to be used and the depth of irradiation and doses of radiation to be delivered. Once these parameters have been programmed into the device, the delivery of the radiation can then proceed.

Typically, as is presently done, for instance in prostate seeding, once the lesions are marked, a simulation of the proposed procedure would be performed. Techniques of radiation simulation that are presently available would be incorporated in programming of a general purpose computer used in conjunction with the system.

The radiation oncologist will select the appropriate arm to be used and will, using the SRIORT device move the arm into position to extract the selected cassette from the radiation source storage cart (pig, in the case of a radionuclide source). The cassette will have electrical connections which will enable the cassette to identify itself to the SRIORT manipulator and hence back to the control station. The SRIORT will compare the cassette identification with the pre-programmed source selection and radiation dose planning previously done by the physicist to insure that the proper cassette has been mounted with the correct source. The source, while still in its shielded chamber (pig) will then have its aperture set to a specific set of sizes and each size will be measured to verify the accuracy of the aperture size controls prior to extraction. The shutter will then be opened, as well to expose a radiation detector to verify the source activity/strength matches the predicted values calculated and referenced in the pre-programmed controller. This will allow the radiation oncologist and the physicist to resolve any discrepancies prior to actually introducing the device into a patient.

Once verification of the planning and exposure parameters have taken place, the SRIORT control system will allow the physician to remove the cassette and manipulate the robotic arm carrying the cassette into position within the patient via the appropriate trochar. The cassette will also contain a locator transducer which will identify its precise spatial location within the operating theatre and more importantly within the patient. This location will also be transmitted to the imaging workstations containing the medical images and the location of the radiation source within the patient can be depicted on the operating room monitors, as well as directly visualized within the patient on the SRIORT vision system. While this will generally be done with visual spectrum of light, it will also be possible to map non-visual spectrum such as infrared spectra to the visible spectrum to allow the radiation oncologist to observe physiologic activity which might not be observable with ordinary visible light, thus enhancing the physician's ability to identify and treat areas of potential residual cancer and prevent recurrences.

Under these visualization schemas, the physician from the SRIORT control station will advance the radiation cassette into the proper position to deliver the radiation to the intended target. The radiation oncologist will then set an aperture size appropriate to treat the lesion, and then visually identify this aperture by means of a self contained field light which will replicate the actual radiation field through the aperture. Comparing this field light with the area of interest, the physician, in real time will make fine adjustments to the position of the source and aperture size to conform precisely to the area to be irradiated. The field light can be supplemented with an aiming laser device attached to the cassette or the SRIORT arm carrying the cassette.

Once this is done, the SRIORT will perform final exposure rate and time calculations and the shutters will be opened, allowing the cassette's radiation source to irradiate the lesion to the dose and depth desired for proper disease control. The radiation oncologist will have the ability to review and examine directly by manipulation of the SRIORT to the previously stored coordinates of areas of interest, the imaging studies and via direct visible and extra-visual spectral mapping information.

This process will be repeated as many times as is necessary to properly treat each and every lesion identified for the best hope of permanent eradication of the cancerous lesions. In each case, the radiation oncologist and the medical physicist will have the ability to select from a variety of cassettes, the appropriate intra-operative radiation applicator for each lesion to be treated with radiation at the time of the surgery and to manipulate and program the sources in real time for the best possible chance of cure of cancer and neoplastic diseases.

In the case of other sites, such as the head and neck, brain or chest, these procedures described above will be equally applicable, with appropriate modifications for the site of disease. This SRIORT device will permit the use of radiation to treat areas previously untreatable intraoperatively due to the inability to position accelerators precisely. Other devices, such as Med-Tech's brachytherapy intraoperative applicator, are incapable of the precision necessary to spot treat lesions of interest without causing unacceptable morbidity for lesions located on or adjacent to radiosensitive organs.

While the invention has focused on a procedure relating to incision surgery and resection of tissue, and follow-up by irradiation to achieve adequate margins, the invention is applicable to surgery where resection is deemed undesirable, such as so-called "inoperable cancers." These involve lesions which for instance are adjacent to the aorta where resection has too high a risk of mortality. This invention enables a stand-off from a critical vessel or organ, and use of irradiation, potentially in a step-by-step manner, to destroy tissue iteratively, avoiding physical contact with the radiosensitive tissue, and/or permitting healthy tissue to grow back.

Another variation is to utilize a sensor on a moving organ or in conjunction with a moving organ and coordinate the output from that sensor with the opening and closing of the shutter and aperture, and the positioning of the capsule. Thus, for a lesion on heart tissue, an EKG lead could be connected and integrated with a general purpose computer so that radiation exposure would be timed to only occur at certain points in the relative movement of tissue vis a vis the capsule. Alternatively, a range finder, either visual, optical, or ultrasonic, on the capsule could be coordinated with the aperture so that radiation exposure occurred only in certain distance ranges. This would enable certain heart and pulmonary-aortic lesions to be treated by a stand-off tissue irradiation with considerably less danger to a patient. The capsule could be moved in conjunction with rhythmic tissue movement.

The invention can be used, for example, in conjunction with intraparenchymal lesions in the liver. The liver is radiosensitive tissue and the intraparenchymal lesions are not ordinarily amenable to radiation therapy without lethal consequences.

The invention enables stereotactical radiosurgery type techniques where the physician can, in real time, determine the depth of effect of irradiation, and make real time adjustments in dosages, hopefully eliminating another invasion of the patient's body.

The invention contemplates a means for positive attachment of the capsule by which is meant that the robot arm has a clasp, finger, bayonet, clamp or slide mechanism to positively lock the capsule, and further, has an electrical feedback mechanism that operates only when positive lock has occurred meaning the capsule is securely attached to the robot arm. A means for positive attachment also includes a surgical end effector as defined in U.S. Pat. No. 6,246,200 cited earlier.

The invention contemplates that other arms of the surgical robot may be engaged in surgery, or in tissue manipulation to facilitate entry of the capsule for irradiation.

If multiple consoles are contemplated, prior art describes and this invention would use an arbitration mechanism to preferably give priority at all times to the handling of the capsule containing a radioactive substance absent a specific command to the contrary.

Potentially a speech interface could be included to assist in direction on pre-defined axes, but it is important to remember of radiologic safety reasons, close manual override and control is needed.

While the preferred mode of electrical communication and control is a physical electrical connection and control by pins on the capsule against contacts on the robot arm or vice versa, another mode of invention is to use telecommunication between the surgical robot, or to the surgical robot, and/or telecommunication to the capsule.

The term means for imaging is intended to include CT (computer tomography), MRI (magnetic resonance imaging), ultrasound or ultrasonic imaging; functional MRI, PET (positive emission tomography), PET/CT and nuclear medical scanning.

The term means for direct visualization or direct visualization includes the use of visible infrared and ultraviolet light or any combination of those to enable direct visualization.

Also proposed is the concept of placing two means of direct visualization enabling true internal stereoscopic visualization through more than one mounted means for direct visualization on the capsule.

The term means for direct visualization or direct visualization includes the use of visible, infrared and ultraviolet light or any combination of those to enable direct visualization, including an endoscope or a laparoscope.

Also proposed is the concept of placing stereoscopic endoscope or stereoscopic laparoscope, meaning two means of direct visualization enabling true internal stereoscopic visualization through more than one mounted means for direct visualization on the capsule.

The term "stand-off remote detection" includes radar and electric signaling for determining distance; in this invention the stand-off remote detection is primarily intended to determine the distance from the radiation source to the tissue being irradiated, taking into account the tare length of the radiation source to the edge of the capsule, or the end of the shroud if one is used. Other forms of stand-off remote detection are also discussed such as ultrasound and laser optical finders.

A fail-safe closed position means that if power is lost, particularly power to operate the shutter, the shutter closes occluding the aperture through which radiation is being emitted into the patient.

This invention describes a capsule containing a series of cylindrical shells which contain an aperture, which aperture may be conically shaped, or other shape such as a square, rectangle or ovoid, or any other pertinent geometry, which when the cylindrical shells having apertures are rotated into position by remotely operable means for controlling the shutters, preferably a mechanical means, and preferably a stepper motor, will result in the apertures be aligned to expose the radiation source to the outside of the capsule and patient tissue. When closed, the shells will rotate to occlude the source, preventing full-strength exposure and the apertures in the cylindrical shells will be offset from one another minimizing radiation leakage through the closed shutter apertures from the radiation source. By this means, a compact shutter mechanism can occlude a radiation source sufficiently to eliminate undesired full strength exposure and reduce leakage from the radiation source by distributing the apertures in the cylindrical shells across a variety of thin shells of a cylinder and offsetting them from one another when the source is "off," thereby functioning as a shutter and being a compact shutter system.

The materials, elements, description, and methods described and illustrated in the Description of Figures, and the Figures themselves, are adopted by reference into this description of the invention. FIGS. 16-38 show various embodiment and design details of the invention using cylindrical shells to occlude the radiation source. There could be one cylindrical shell, but multiple shells have many more advantages as will be explained.

This invention is contemplated as a significantly improved shuttering mechanism for the Direct Visualization Robotic Intra-Operative Radiation Therapy Applicator Device described in U.S. Pat. No. 8,092,370, and more generally, surgical robots, but will also find application in other fixed source exposure systems where a reasonable amount of leakage is acceptable but compact devices are desired or necessary. Conventional shutters consist of large and bulky collimation systems which require heavy servomotors to drive shutters into place. By using a cylindrical shell radiation shutter system also referred to as a cylindrical shutter system or a cylindrical shell shutter system, the shutters can rapidly open and close a source by spinning into position in the open and closed position. This invention describes an alternate means of control of radiation exposure to ablate cancers and other material(s) used in the radiation ablation capsule described in US 2012/0016175A1 and U.S. Pat. No. 8,092,370. Because a sliding shutter closure system consisting of a single thick sliding shutter may not fully occlude or alternatively will create significant radiation penumbra, or leave air voids with low radiation attenuation, the invention provides a better means of exposing and occluding the source is required. The cylindrical shell mechanism described overcomes this limitation. Mechanical gaps in a sliding shutter arrangement permit radiation leakage. The invention, by means of concentric shutters substantially reduces the release of undesired radiation by minimizing such air gaps and eliminating edge leakage. Where compact irradiation devices are essential, this technique will decrease the bulkiness of the device.

The cylindrical radiation shutter system has a solid radiation source, generally a photon emitter, but sources emitting other radiation, including beta, alpha and neutron particles are equally acceptable. In the capsule contemplated by this invention, this defined central axis of the capsule is preferably perpendicular to the longitudinal longer dimension of the capsule (referred to as the "capsule central axis" or "defined capsule central axis"). The other important axis is the axis from the central point of the radiation source to the outermost beam port (referred to as the "radiation central axis"). The concentric cylinders described in the next paragraph are preferably perpendicular to a line drawn from the radiation source on the capsule central axis to the center of the opening of the capsule through which radiation will be emitted (the "outermost beam port") which outermost beam port opens perpendicular to the radiation central axis, but is located on the side of the capsule (also referred to as the "outermost beam port") parallel to the defined capsule central axis. Alternatively, the defined capsule central axis could be perpendicular to the longitudinal longer dimension of the capsule, and the outermost beam port can be on one end of the central capsule axis. In that design, the concentric cylinders described in the next paragraph are preferably perpendicular to a line drawn from the radiation source on the central capsule axis to the center of the outermost beam port opening at the end of the capsule through which radiation will be emitted, and are also perpendicular to the central capsule axis. The alignment of the outermost beam port opening and radiation central axis could be at any desired angle from the capsule longitudinal central axis so long as it does not irradiate in a direction to damage the operating mechanism of the capsule.

On that defined central capsule axis, in a preferred mode, surrounding the central radiation source are a series of thin concentric cylindrical shells (also referred to as "cylinders"), each with a cylindrical shell aperture cut into the cylindrical shell. The apertures depicted are circular and diverge with a solid angle divergence from the source, but could be designed with any number of shapes depending on the desired projected radiation field when radiation exposure is desired. These shapes could include a round shape as depicted, a square shape, a rectangular shape or any irregular polygon for which a divergent series can be cut in each of the shutter cylindrical shells. The exit port of the shutter can be any size, limited only by the size of the radiation source, which is generally an isotropic or nearly isotropic source. The calculations for irregular shapes are determined using a Sievert integral.

When the device is activated, the cylindrical shells are rotated such that their apertures are aligned, exposing the source and permitting radiation to exit the source through the aperture, while the remainder of the source is shielded by the walls of the shutter, and the cap thus permitting unidirectional and precise control of irradiation at the full intensity of the source. A traditional sliding or closing obstructing jaw shutter can be combined with the cylindrical shell.

When no radiation exposure is needed, (i. e. full-strength radiation is occluded from being emitted thought the outermost beam port to ablate issue, and is "off" or "closed"), the cylindrical shells are mechanically rotated such that there is no overlap of any of the cylindrical shell apertures. Thus, the radiation source is protected with no air gaps in the closed shutter assembly, reducing leakage of radiation. In the closed position, the inner cylinder is rotated sufficiently to offset the outer port opening, the next shell (cylinder) adjacent to the innermost shell is rotated further to insure no overlap in the beam aperture between the inner and second cylinders. The third cylinder is rotated further so that its aperture overlaps neither the first, nor the second, providing minimal air gaps in the shutters which will reduce radiation leakage through the shutter mechanism. This is repeated until all the shutter cylindrical shells have their apertures offset from one another and from the outer most beam port. The number of shells can be 1, 2, 3, 4, 5, 6, or any integral number up to 20.

Each cylindrical shutter will contain a gear tooth affixed to at least one edge, preferably its lower edge. This tooth will fit into a gear plate with a slot to cause selective movement with the rotation of the gear plate.

The gear plate will consist of a number of concentric tracks, (arbitrarily labeled a, b, . . . ) each track of variable angular length which will move each shutter a variable length calculated to insure no overlap of the apertures of each of the cylindrical shutters with each other and with the outermost beam port (emission aperture) on the surface of the capsule when the cylindrical shell shutter system is "off" or "closed.". Each track will have a variable angular length slot and will correspond with each cylindrical shell component of the shutter which will move each shutter component a variable length calculated to insure no overlap of the apertures of each of the cylindrical shutters with each other and with the shell port and source port when no irradiation is desired. In each track, there will be a variable length arc to cause selective motion of each individual shutter cylinder.

The gear tooth on each shutter will align with the aperture in such a way so as to cause all the apertures to align when the gear plate is rotated clockwise, opening the port by aligning all the apertures and exposing the source when irradiation is desired.

When the gear plate is rotated counter clockwise, the first cylindrical shutter A (labeled arbitrarily A, B, . . . [up to the number of cylindrical shells] corresponding to each track on the gear plate) will turn away from the radiation source and outermost beam port on the surface of the capsule. Once shutter is fully turned away, the next shell B with its gear tooth set in a variable length slot on the next inner track (b) of the gear plate will engage and begin rotating away from the shell aperture (or radiation source opening described below). Once this shutter shell has turned far enough to occlude the more interior cylindrical shell aperture, the next inner shell C gear tooth will be engaged by the next inner most variable length track (c) on the gear plate and begin turning away from the outermost beam port and interior cylindrical shell apertures until all cylindrical shells are offset from each other and the outermost beam port. The source itself can be situated in a conical setting and the exterior of the cone facing the outside of the capsule, termed a radiation source opening, and in this variation, any interior cylindrical shell would be rotated away from the radiation source opening.

To open the shutter system, the gear plate will rotate in a clockwise direction which will bring all the gear teeth on each of the cylindrical shells to bring the cylindrical shell apertures into alignment and turn until the cylindrical shell apertures are all facing the outermost beam port and the radiation source or radiation source opening. This will expose the radiation source permitting un-attenuated radiation in the shape of the apertures, which are designed to account for a near point source, or any other arbitrarily shaped source in the geometry. Ideally, the cylindrical shell apertures are cut conically cylindrical shell by cylindrical shell with the conical shape widening toward the exterior of the shell so that a smooth 3-dimensional symmetric cone with a straight gradient from the radiation source to the exterior diameter of the outer emission aperture in the capsule is created, minimizing penumbra.

The gear plate is turned by a stepping motor with a direct drive shaft affixed to the center of the gear plate. The motor will turn the gear plate counter-clockwise the correct angular distance to fully close (offset the apertures) or turn the plate clockwise to fully open the cylindrical shell apertures such that their individual apertures are all aligned with the beam port, thus irradiating the desired target.

A mechanical failsafe mechanism to act as a means for a fail-safe closed position is incorporated into the cylindrical shell shutter system such that in the event of a failure of the drive motor, the failsafe will rapidly snap the shutters to the closed position by turning the gear plate counter-clockwise, causing the shutters to cease alignment with the beam port, offsetting each other and occluding the radiation source. This spring will be a main-spring which will be wound when the shutters are opened by the drive motor. The motor will hold the shutters open against the force of the spring with an idle current. Should that current fail, indicating a loss of power or control to the motor, the spring will rotate the gear plate under mechanical force, closing the shutters, permitting the device to be safely retrieved. Alternatively, a spring could be contained within a circularly shaped groove and stretched when the cylindrical shell shutter system is operated, and if power fails, the spring returns to its rest position and drags the cylindrical shells to offset the apertures and prevent full-strength radiation. Alternatively, a circular coil spring similar to a clock mainspring can be attached to a tab on for instance the outer shell and a series of tabs mounted on the interior shells that are engaged by that outer shell tab so that when the device fails or is not operated, the circular coil spring draws the outer shell to its rest position and engages the tab on the next interior shell which engages the tab on the next interior shell until the innermost shell is moved and all of the rest positions leave the apertures rotationally offset from each other.

The advantage of the present invention compared to a typical shutter alternately moving in one plane is that the air gaps or voids from the space vacated by the linear shutter are eliminated as are potential lines of radiation leakage.

The effective undesired dose outside of the beam path which traverses necessary gaps in shielding material is given by the formula $I = I_0 e^{(-\mu x)}$ where is the mass attenuation coefficient and x is the total thickness of the shielding material (less air gaps). As can be seen in above the beam port in FIG. 15, an air gap must exist to accommodate closing the shutter, which reduces the shielding thickness with a consequent increase in undesired radiation leakage outside of the desired radiation field. Where x=0 (within the beam path, there is no attenuation from shielding. Where there are air gaps in the shutter the value of x is reduced by the path length of the air gap resulting in differing shielding attenuation, increasing undesired leakage and restricting the beam port shapes to those shapes easily mechanically accommodated.

Conversely, below the beam port, the shutter itself creates a variable air gap due to its physical characteristics, which will partially attenuate the beam causing a variance in beam intensity (penumbra) resulting in undesirable overdose/underdose at the field edge.

This leaves the following potential dose in-homogeneity:

Source to device surface distance along the mechanical discontinuity: 2.8 cm.

Shielding Available (shielding—mechanical space air gap): 1.4 cm

Which leaves a total shielding thickness of 2.8 cm–1.4 cm=1.4 cm

If a maximum typical exposure time is 75 minutes with an unshielded source of 177 cGy/minute, and lead is used in the device (for the purposes of this example), the tenth value layer (TVL) of lead is 0.6 cm.

$$\frac{(1.4 \text{ cm})}{(0.6 \text{ cm})} = 2.3 TVL$$

The resulting dose attenuation is:

$$177 \frac{cGy}{\min} 10^{-2.33} = 0.83 \frac{cGy}{\min}$$

If there were no air gap at all in the shielding, the dose attenuation would be improved to $$\frac{(2.8 \text{ cm})}{(0.6 \text{ cm})} = 4.67 TVL$$

and the leakage will be reduced to $$177 \frac{cGy}{\min} 10^{-4.67} = 0.00378 \frac{cGy}{\min}$$

Thus this air gap is significant and inhomogeneities in shielding can cause remarkable differences in radiation field doses. If a typical desired irradiation of 24 Gy is desired, the exposure time will be 24 Gy/1.77 Gy=14 min 6.6 seconds. The leakage from a shield with an air gap (discontinuous) will be 0.83 cGy/min×14.12 minutes=11.7 cGy. With a continuous shield the undesired exposure will be reduced to 0.05 cGy. This the elimination shielding discontinuities has a significant impact on reduction in unwanted radiation dose.

As an alternative, the shutter system base will contain a pair of opposed pins extending below the shutter system with its cylindrical shells which will have a base that rides on a circular cam plate and acts as a cam follower. The cam wheel itself will have a raised surface of varying lengths based on displacement of each cylindrical shutter shell from the radiation central axis. This surface length along each arc of the cam will cause each cylindrical shell to move a requisite arc length to avoid overlaps of the apertures, thus maximizing shielding and minimizing leakage. When the shutter is opened, the cam will rotate in the opposite direction and a second raised surface on the cam plate will move the shutter in the opposite direction to align the aperture openings and expose the source, permitting irradiation to take place.

Alternatively, a series of concentric cam plates can be utilized, with placement of a hole for a pin from each cylindrical shell shutter and an actuating mechanism which could consist of either individual drive motors or a single drive motor with a cam shaft and keyed slot in each of the cam plates permitting variable, independent rotation. A complicated variation which enables variance in treatment strength is to not move one of the cylindrical shells and in a calculating manner, reduce the otherwise full-strength radiation directed to a tissue in a patient.

Using this shutter system, a much less bulky and more compact radiation source shutter system can be developed. Present mechanisms require thick and heavy single sliding shutters. This improvement reduces the gaps in shielding necessary to accommodate a thick sliding shutter, minimizes air gaps which reduce shielding effectiveness and permits an overall more compact shutter system as well as reduced leakage from the space necessary to accommodate a thick shutter.

This alternative shutter mechanism also simplifies source loading and unloading. The source may now be contained as part of the capsule cap. (FIG. 9). With this loading technique, the source rod is mounted centered on a cap with the radiation source at the opposite end of the source rod, and the radiation source is kept in a receptacle with the cap partly shielding the source when the source/cap assembly is retrieved to insert into the irradiation device. The centered source rod containing the source is then inserted into the cylindrical shutter assembly and locked into position. The device is now ready to be used. At the midpoint of the cylindrical shutters on that central capsule axis is a solid core in the capsule that fits with the capsule cap and is made larger in diameter than the radiation source so that the radiation source cannot by a straight line beam pass interior to the first moving cylindrical shell and exterior to the solid core. Thus the radiation source is shielded by the cap and source rod itself on one end along the central capsule axis and by the solid core on the other end.

An alternative embodiment is to orient the cylindrical shells perpendicularly to the capsule central axis and have the aperture through the capsule at the end of the capsule through which aperture from the cavity the patient is exposed to radiation. The shells preferably have a similar shape to the shape of the end of the capsule to enable them to be mounted more closely to the end, the gearing can be to the side of the shells and the cams can be used for positional guidance as opposed to be driven, but the same principles apply to calculations of the thickness of the shells. The loading would be optimally from the side, that is perpendicular to rather than parallel to the capsule central axis with the radiation source again generally centered among the cylindrical shells.

A camera can be mounted such as a small CMOS camera. A so-called raspberry pi embedded control or Arduino board using I2C logic can be utilized for control. A Mouser LI-5M05CMAF available from Mouser Electronics, Inc. of Mansfield Texas is an example that can be used.

Radiation shielding efficiency increases substantially and makes practical new compact irradiation devices which where heretofore larger and bulkier. This is demonstrated through the following calculations for uniform thickness shells in an example which would be used for human irradiation in an operating room:

Pertinent Example Dose Rate Calculations $$^{192}\text{Ir}$$

Iridium-192 Physical Characteristics:
Air Kerma Rate Constant ($\Gamma$):

$$\frac{\left(108\mu Gy\ \text{m}^2\right)}{(GBqx\ \text{hr})} \text{ and the } Pb\ TVL = 0.6\ \text{cm}$$

AAPM defines U as $$\frac{\left(1\mu Gy\ \text{m}^2\right)}{\text{hr}} = \frac{\left(1cGy\ \text{cm}^2\right)}{\text{hr}}$$

Simplifying the Air Kerma Rate Constant:

$$\Gamma_\delta = \frac{(108U)}{GBq}$$

Note: Glasgow uses 111 for Ir-192.
Given this, the specific exposure rate at 2.5 cm source to surface distance (SSD) for a 10 Ci (370 GBq) source is 110 cGy/min and the time of exposure to deliver a 24 Gy does is about 21 minutes. To deliver 16 Gy takes about 15 minutes per site.
Leakage Calculations:
1. Patient undesired exposure with shutter open and exposing tissue.
Exposure rate at 2 cm through full thickness shield of 2 cm of Pb equivalent material.

$$370GBq\left(\frac{1}{(2\ \text{cm})^2}\right)\left(\frac{111cGy\ \text{cm}^2}{(GBq\ \text{hr})}\right)\left(\frac{(1\ \text{hr})}{(60\ \text{min})}\right) = 111cGy/\text{min.}$$

for unshielded exposure rate.
The Tenth Value layer thickness of Pb is 0.6 cm. The total shielding from the capsule is 2 cm giving $$2.0\ \text{cm}\left(\frac{(1TVL)}{(0.6\ \text{cm}\ Pb)}\right) = 3.33$$

The final leakage rate at the surface is $$L = \left(111\frac{cGy}{\text{min}}\right)10^{-3.33} = 0.051cGy/\text{minute}$$

Assuming a 24 Gy primary target irradiation for 5 sites, the maximum normal tissue exposure is approximately 75 min-utes×0.051 cGy/minute=3.86 cGy, which is an acceptable dose.

Next, we must determine the maximum leakage at the surface for the shutter mechanism with the aperture closed. Assuming uniform shutter wall thickness (worst case scene) there will be a reduction in shielding due to the aperture air gap for any given shell. This will reduce the effective shielding thickness by 0.5 cm, giving a shield path of 1.8 cm instead of 2.0 cm of Pb (or equivalent) or 3.33 TVL. This yields an exposure of 8.3 cGy which is also reasonable, especially given the fact that when the shield is closed and it is highly unlikely that the applicator will remain in a fixed position for 75 minutes. Thus, the design is very reasonable. A typical exposure time for each site treated would be _75 minutes/5=_15_minutes.

Finally, we must consider personnel exposure and ICRP occupational dose limits. The likely closest exposure point would be anesthesia personnel at the head of the patient or about 1 M from the abdominal cavity, and somewhat less in the thoracic region. For the purposes of discussion we will assume 1 meter Source to nearest OR personnel. As the OR will be a radiation control area, we will have all personnel badged and trained. This calculation assumes no lead apron shielding, although in practice, it is likely that OR personnel will don lead aprons, further reducing potential personnel exposure.

Exposures to Occupied Space at 1 meter with capsule aperture closed:

$$370GBq\left(\frac{1}{(100\ cm)^2}\right)\frac{(111cGy\ cm^2)}{(GBq\ hr)}\left(\frac{(1\ hr)}{(60\ min)}\right) = 4.107cGy/\text{min}.$$

With 2 cm of Lead equivalent shielding, the exposure rate drops to $$L = \left(4.07\frac{cGy}{min}\right)10^{-3.33}\left(\frac{(60\ min)}{hour}\right) = 0.114cGy/\text{hour}$$

at the surface of the capsule.

This is a raw value which does not account for tissue attenuation or supplemental portable shields which may be easily placed between the patient and the OR staff. Nor does it account for lead apron shielding which may be available for personnel. Assuming a typical irradiation procedure is 2 hours from the time the source is loaded from the container to the time it is returned to the container, for radiation safety discussion purposes, this exposure is 0.00228 Sv at 1 m.

The NRC occupational dose limits, (10 CFR 20.1201) permits an annual limit of 0.05 Sv. Without additional shielding, a total of 17 cases could be performed. In practice, we try to achieve a much lower dose to personnel (ALARA). By moving personnel to 2 m, rotating OR staff and physicians, and/or placing a minimum of portable shielding we reduce this dose easily to very reasonable levels. At 2 meters from the source, (6 feet) the exposure for a lengthy procedure is reduced by 4 from 0.00228 Sv at 1 m to 0.00057 Sv at 2 m. The annual limit would permit the same team to perform a total of 87 cases per year, without additional shielding.

In practice, an additional 2 cm of Pb in a portable shield would reduce this dose much further, and it is highly unlikely that the source will be in use for a full 2 hours/procedure, thus the ability to consistently perform 1 or 2 cases per day is readily achievable without exceptional shielding.

Shielding advantage is given by the formula:

$$I = I_0\left(\frac{1}{r^2}\right)e^{\left[-\left(\frac{\mu_{en}}{\rho}\right)_E \rho x\right]}$$

Where there are multiple attenuators of differing atomic composition in the beam path, the amount of attenuation, overall is a function of the sum of the attenuators and the inverse square of the distance from the emission source. Thus, the relative attenuation for the cylindrical shell shutter is:

$$I = \sum_{n=1}^{n} I_0 e^{-\left[\left(\frac{\mu_{en}}{\rho}\right)_n \rho x_n\right]}\frac{1}{r_n^2}$$

where I is the emitted radiation at a point of interest in space after passing through layers of materials of thickness x and having mass-energy attenuation coefficients $\mu/\rho$, $\mu$ being the mass-energy attenuation coefficient for the shielding material, $\rho$ being the density of each layer, with x the thickness of each layer of x and r is the distance from the source at the outer surface of the shell.

When multiple attenuators are arranged in the radiation emission path, the final emission is dependent on the atomic number of the intervening absorbers and corresponding mass attenuation, and the inverse square of the distance. In the simplified drawing below a comparison is made to the relative increased shielding efficiency by using a cylindrical thin-shell shutter as compared with the more conventional massive sliding shutter:

Case 1: Mono-thickness massive shutter:

Source at position (0,0,0)

Shutter travel length 5 cm

Shutter thickness 2 cm

Source to shutter distance when closed ~0 mm

Source to shutter housing gap when closed=x sin 45°=2.7 cm

Thickness of attenuator at surface (housing thickness)=5 mm

The total distance from the source to the closest point on the shutter housing will be 3.2 cm. For a point source of initial intensity $I_0$, a gamma emitter of energy 0.4 MeV, and tungsten shielding, the mass attenuation coefficient is 0.1925 cm^2/g, and density is 19.25 g/cm^3. Air attenuation for this purpose can be neglected. Therefore the path distance in air is a proximately 2.7 and the attenuation available is from the shutter housing alone, which is 5 mm. This yields an attenuation of 0.0153.

With the cylindrical shutter, at the same position, the source will benefit from the full thickness of the material from which the cylindrical shutter is made (in this example, tungsten) giving an attenuation thickness of 3.2 cm instead of 0.5 cm, and an attenuation factor of 6.8 E-7, as opposed to 0.0153, or 6 orders of magnitude better.

In the direct beam path, the effective loss of shielding is in line with the source and the apertures in each of the cylindrical shell shutter components, giving a maximum air gap of 0.5 cm in the example shutter cylindrical thickness. The inverse square distance is also in operation, with the smallest aperture closest to the source, and the largest furthest from the source where the inverse square reduction in intensity is the greatest.

The radiation leakage path will contain full thickness shielding less the thickness of the shells which can be varied to meet shielding criteria. In addition, this invention using the cylindrical shells also permits a variety of aperture shapes permitting a much more flexible tailored design, in contrast to a single-piece, relatively-more-massive sliding shutter. The only accommodation required for novel shutter aperture shapes is that the size be small enough to avoid overlap of aperture windows in each of the cylindrical shells when they are in the closed position and the aperture cannot be so large relative to the source that the beam begins to form a penumbra.

Radiation intensity decreases by the square of the distance from the source. Because of this, an alternate implementation is a cylindrical shell shutter with varying thicknesses of the shells instead of a monolithic uniform shell thickness for each shell, with the inner cylindrical shells being thicker where the aperture is smaller. The aperture size is a function of arc length and is given by the distance from the inner shell wall from the source and the ultimate size of the aperture. For the purposes of this disclosure, we use 2 cm aperture size at a 2 cm given source-surface distance, requiring a 1.8 cm arc length on the outer shutter shell, but the same concept applies at any aperture size and device size. This leaves an aperture angle of 52°. This will permit complete offsets of each shell aperture from one another.

An alternate implementation is to use equi-attenuation cylindrical shells, rather than equi-thickness shells. This is advantageous since the inner shells have a smaller aperture in each shell than outer shells, which will result in less radiation reaching the outer shells and a thinner outer shell may be feasible, as an equivalent radiation shielding thickness is less, due to the inverse square reduction in radiation present at the inner surface of the outer shells. If we desire to use equi-attenuation at each shell distance, the calculation for shell thickness changes, allowing outer shells that are further from the source to be thinner than the inner shells to achieve the same attenuation effect. Thus radiation leakage is reduced with this method over conventional massive aperture collimators because the shutter mechanism in conventional radiation beam collimation are massive single piece or sliding, full thickness "fingers." In the cylindrical shell shutter system described in this invention, the cylindrical shells where the aperture is smallest, close to the radiation source can be thicker, resulting in reduced radiation shielding requirements in the next further out cylindrical shell because of both inverse square reduction in field intensity and the fact that the aperture region in the inner cylindrical shell is relatively small due to divergence factors compared with each subsequent shell aperture. This results in a much more compact shutter mechanism with superior radiation leakage characteristics with a relatively simple mechanism. With this scheme, the only limit is the thinness of the material which will guarantee mechanical stability of the thin cylindrical shell. The variable thickness, equi-attenuation shell concept is given by:

$$x = \frac{1}{\mu} \ln\left( \frac{I}{I_0} r^2 \right)$$

Where (as above)

I=desired leakage/acceptable leakage (Sv)

$I_0$=incident radiation intensity (Sv)

r=radius from the radiation source (cm)

μ=density corrected mass attenuation coefficient, i.e. [(μ/ρ)(ρ), with units of cm$^{-1}$]

The cylindrical shell radiation shutter system with cylindrical shells, situated within a capsule, has additional advantages in that it permits the design of compact, highly directional radiation devices. A further advantage is that while the drawings demonstrate a conical aperture, the cylindrical shell shutter permits the design of any convenient beam port shape such as square, rectangular, ellipsoid, or any regular or irregular polyhedron necessary to meet the desired irradiation pattern, consistent with source size and shape. An alternative embodiment of the cylindrical shell shutter system would include a modified gear plate or turntable. The outermost shell would have a pair of opposing teeth which would insert into the gear plate as shown in FIGS. 21-36, particularly FIGS. 21, 32, 35 and 36. It could also include any even number of opposed gear teeth. This will preserve rotational stability of the outer shell during the opening and closing process. The outermost shell will contain on the opposite surface a drive tab which will overlap the next innermost shell. The next innermost shell will not have a gear plate surface drive tooth, but rather contain two tabs on the opposite surface which will be driven by the outermost shell. These will be offset so that when the device is rotated clockwise, the tabs will cause alignment with the beam port in the shutter shells and cause the device to emit full strength radiation. These tabs will be angularly offset such that in the clockwise rotation then fully engaged the shutter aperture will be open. When the outer shell is rotated counter-clockwise, the opposing tab will be engaged on the two shells and will cause the outer shell to rotate away from the beam port opening, and the upper tab will engage the next innermost shell after sufficient angular rotation of the outer shell has occurred to then move the next inner shell port away from the aperture, offset from the outer shell port causing occlusion. A second set of tabs on the next (2$^{nd}$) innermost shell will likewise cause the next (3$^{rd}$) innermost shell and so forth until all of the inner shells are offset from each other and the external aperture, fully occluding the radiation source and attenuating radiation to a safe and non-therapeutic level. In other words, the two opposing teeth that match to the gear plate and are fixed to it when turned in one direction and opposite that direction can have tabs or cams extending into the next shell to engage it with a cam follower to allow that shell to alternately open and close. As a reasonably skilled practitioner would recognize, this arrangement can be reversed so the rotation occurs in opposite directions to those just stated.

With this alternative method of implementation, the opportunity to create a hollow path in the device could be used to also further enhance radiation safety with the use of remote after-loading radiation equipment which could be used to insert a source into the device once it is placed in position and removed once the treatment delivery is completed. This additional implementation would allow "on the fly" changes in radiation sources of varying physical characteristics appropriate to the findings at the time of surgery, substituting one source for another without the need to remove the device from the patient and return it to its docking station for source exchange. Conversely and less desirably, an arrangement can be made whereby the cams can be arranged so tabs are moved by the means of remote control, usually a stepper motor and the cylindrical shells are designed to be moved as if they were the gear plate.

In another embodiment, one or more stepper motors can be used to direct drive a cylinder shell and with judicious use of cams and tabs overlapping to another shell and cam followers, one stepper motor can be used to direct drive more than one shell.

The source could be afterloaded either through an access channel in the cap, robotic coupling or other path into the center of the cylindrical shell by means of a flexible tube as is used in conventional remote source afterloading of fixed catheters. A disk type spring or alternatively, a series of tension springs would insure positive activation of the various shutters for full open/close operation, thus providing an additional redundancy to reduce the probability of shutter activation failure.

A means for a fail-safe closed position means a fail-safe closed position means that if power is lost, particularly power to operate the shutter, the shutter closes occluding the aperture(s) through which radiation is being emitted into the patient.

Another mode of invention is a capsule inserted into a 1-3 centimeter incision the doctor will make in the patient. The invention preferably uses a combination of doors contained on and in the capsule. The first "door" is an aperture disk which has a conical aperture. The aperture disk rotates; when the conical aperture is aligned with the isotope opening, tissue is exposed to the radioisotope. As the conical opening is rotated and no longer aligned, the aperture is in the OFF position and tissue is shielded from the isotope. The second door is a sliding door exterior to the aperture disk that slides up and down a portion of the length of the capsule. This door also has a fail safe mechanism which can be a spring. In the event of power failure, the spring will force the door closed to prevent unwanted radiation exposure.

The capsule can be set up while the radioisotope is in a lead pig on a table, and the capsule can be moved by the surgical robot to pick up a cartridge containing the radioisotope. Alternatively, the robot can pick up the capsule in which the radioisotope is mounted, with the capsule stored in the lead pig.

Using the present invention, a small capsule inside the patient manipulated by a robotic arm would minimize the collateral damage to healthy tissue that is associated with these procedures.

The da Vinci Surgical System® is the robotic surgical device that is to be used to manipulate, control, and direct the radiation capsule while it is inside the body cavity of a human. A surgeon seated at a control station manipulates hand controls with several degrees of freedom. The surgeon can be shielded from a lead pig initially holding the capsule or radioisotope, and from the radiation. These hand controls of the surgical robot translate the surgeons hand motions into end-effector movement. Different end effectors are used for different purposes (i.e. gripping and grabbing tissue, others for cutting, sawing, sewing, or any other action that is conventionally performed by the hand of a surgeon). These end effectors of the da Vinci® arms actually have a wider range of motion than the human wrist.

This invention mounted on to the da Vinci® arms would be capable of attacking tumors from a variety of angles that simply could never be achieved using standard linear accelerator technology.

Additionally, in the present invention, the camera mounted in the capsule provides direct visualization to the radiation oncologist at the operating station so that he can see, in real time, what he is operating on, locating and attacking multiple tumor sites in one operation. The radiation oncologist can, therefore, more effectively destroy cancerous tissue in the body while dramatically reducing collateral damage to healthy, vital tissue. This capability is far superior to standard treatment methods today.

Another preferred way to implement the invention is to build a capsule so it can be assembled together. The oval-shaped capsule (1) has various parts. The oval-shaped capsule is generally made of a radioopaque or minimally radiotranslucent material, including a material selected from the group of radioopaque or minimally radiotranslucent materials, including gold, depleted uranium, tungsten or platinum (for convenience sake, the radioopaque or minimally radiotranslucent material is referred to by the one word "radioopaque"). Starting with a radioopaque slide door (2) (also called a shutter) which can be alternately opened and closed to occlude radiation through an aperture opening in the front mount, that door slides into a radioopaque front mount (3) which has a front mount trapezoidal channel (21). The slide door covers a rotating radioopaque aperture disk (4) which has one or more conical apertures (5) with central cone axis for each aperture. The slide door is shaped similarly to a trapezoid and slides into and out of a front mount trapezoidal channel (21) in the front mount and slides in the spring guide (13) mounted in the end cap. The slide door includes a toothed rack (20) that will be connected to it. The rack of the sliding door is mated with a pinion spur gear and is driven by a remotely operable means for controlling the shutter, preferably a stepper motor. The motion created by the motor-rack-and-pinion (one of stepper motors (11), rack (20), and pinion spur gear (22)) system slides the door up and down the length of the capsule thereby opening and closing the capsule.

The aperture disk can be rotated alternately to occlude radiation, and in cooperation with proper material selection for the capsule, can, in a three cm. diameter capsule, occlude radiation emitted from a radiation source (6), which is an isotope disposed in a radioopaque cartridge (8). The isotope is disposed towards the center of the diameter of the capsule and towards the longitudinal center of the capsule, and interior to the aperture disk (4) and cartridge (8). The aperture disk has the conical openings widening toward the exterior of the capsule and when the slide door is open, the front mount aperture opening designed to be wider than the cone cast by the conical opening in the aperture disk. There can be multiple conical openings in the aperture disk so that the capsule has adjustable aperture size. The radioopaque front mount (3) fits onto a radioopaque back mount (7) which together account for about one-half the outside shape of the capsule. The isotope which is the radiation source is optimally secured in an aperture at the end of a radioopaque cartridge (8) which fits into the back mount into a capsule cartridge aperture. The back mount can have a back mount emission aperture aligned with and adjacent to the aperture at the end of the cartridge through which aperture radiation will be emitted; that back mount emission aperture or the aperture at the end of the radioopaque cartridge will be covered and uncovered and the target tissue will be alternately exposed or occluded from cytotoxic levels of radiation aimed at the target tissue depending on the position of the aperture disk and sliding door. The radioisotope can be mounted in a cavity which is either interior to the capsule in an aperture at the end of the radioopaque cartridge (8), or in a cavity formed by the back mount emission aperture. Either of these latter cavities is referred to as an emission cavity. The combination of the aperture opening in the front mount, an open slide door, and the rotating aperture disk allowing unattenuated radioactive emission through the sliding door is referred to as the emitting aperture. When a conical aperture of the aperture disk is aligned with the aperture at the end of the cartridge, and the back mount emission aperture (if any) and the slide door is opened, the radioactive emissions of the isotope are emitted to the exterior environment along an axis perpendicular to the long axis of the oval capsule. The front and back mounts are secured to a radioopaque end cap (9) with the combination forming an oval cylinder which is the ultimate shape of the radioopaque capsule. The end cap has apertures to contain two remotely operable means for controlling the aperture disk, preferably stepper motors (10) and (11) (sometimes referred to as stepping motors) to operate the aperture disk and the slide door. The motors are disposed so that the central axis of the rotating shaft of each motor is parallel to the long axis of the capsule. The motors are secured into a motor mounting plate (12) in turn secured to the end cap (9) which combination secures the motors into the end cap. The end cap has a spring guide (13) which guides a spring (14) which exerts force against the slide door to force it closed in the event of a power failure to the capsule. The capsule, preferably by the end cap, is mounted on or held by a surgical robot and manipulated by the surgical robot.

Two bevel gears (15) mounted on the motor shafts drive bevel gears (16) on two pin-shaped motor shafts (17) mounted into the back mount and when the motor operates, the bevel gears on the motor shafts rotate the bevel gears on the shafts (17) mounted into the back mount. Through one set of bevel gears (one of (15) and one of (16)), one stepper motor (10) drives a spur gear (18) connected to an aperture spur gear (19) fixed on the aperture disk and causes the aperture disk (5) mounted on a shaft (23) mounted on the back mount to rotate to the desired position of the aperture disk and the conical aperture of the aperture disk. The other stepper motor (11), through the other set of bevel gears (one of (15) and one of (16)), drives one of the spur gears acting as a pinion (22) which drives a toothed rack (20) attached to the slide door (as stated, also called a shutter) which causes the slide door to move parallel to the long axis of the capsule to an open or closed position of the slide door.

For a capsule of 3 cm. diameter and approximately 6.5 cm. long, made of tungsten, for an Iridium192 source, approximately 90% of radiation from the radioisotope emitted through the capsule can be eliminated when the slide door is closed and the aperture disk occludes the radiation source from the slide door.

The capsule can have a cartridge (8) that is removable and/or interchangeable. The cartridge can be secured with screws, or be placed so that a surgical robot arm moves the capsule into a capsule, and fits over the cartridge into a cartridge aperture or hollow in the back of the capsule. A linear actuator having an operating pin interior to the capsule can be moved to secure the cartridge by the pin. The preferred mode is to operate the linear actuator to move the pin out of the cartridge aperture or hollow, mate with the cartridge which has an isotope which cartridge is being stored in a lead pig for radioactive storage, and then turn off the power to the linear actuator. The benefit of this mode is that if power is lost to the capsule, the cartridge remains secured in the capsule.

In order to minimize power requirements, a linear actuator to secure the sliding door open while power is on could be used which is perpendicular to the axis of movement of the sliding door to secure the door open and to enable temporary deactivation of the stepper motor for the sliding door. If power was lost, a small spring surrounding this linear actuator or acting on this linear actuator would cause the actuator to release the door and a spring (14) would cause the door to shut and attenuate the radiation to tissue. Another way to minimize energy is to position a lever arm or linkage operating on a pivot actuated by the sliding action of the sliding door. The longer end of the lever is moved by the sliding door, and the travel of the shorter end of the lever is minimized. A spring acts on the lever and the spring is moved from its neutral or unsprung position by the shorter lever arm. When the sliding door is moved to its operating position, the sliding door acts on the longer end of the lever and the shorter end presses on a spring, minimizing the travel of the spring and the force to keep the sliding door open. A series of linkages of levers could be substituted for a lever on the same principle, and is included in the term lever. A linear actuator that operates if there is power to the capsule could be used to lock the lever and enable the stepper motor to be turned off. The remotely operable means for controlling the shutters can be a gear plate interacting with cams, or a series of gears interacting with a stepper motor and the shutters in any of the embodiments of this invention.

The remotely operable means for controlling the shutters, preferably stepper motors, is controlled via a wiring harness or wireless interface from a computer which will communicate with a stepper motor controller, which controls a stepper motor driver, which ultimately sends electric current to the stepper motor (aided by a power supply) which collectively generate output from the stepper motors. Appropriate stepper motors and controllers which function well are available from McMaster-Carr Supply Company, 600 N. County Line Rd., Elmhurst, Illinois 60126; for instance part number AM1020-ww-ee and its accompanying controller 6627T51. A stepper motor controller conforming to Stepper Motor NEMA 8 Controller Information (R256 Controller with built-in 256 Microstepping Driver) should accomplish the needed control. Computer software can be written so that the stepper motors will rotate incrementally until its respective door has moved to its desired position. A programming development environment such as LabView™ software can be used for the controlling mechanism, in particular version 7.1 or higher. Labview software is a software package developed by National Instruments of 11500 N Mopac Expwy, Austin, TX 78759. In conjunction with PW-100-24 two R256 controllers, a personal computer, DB-9 cables with a 4 pin connector, female-female DB-9 connector and an R232 card, serial to USB converter cable and connecting cables and wiring, the aperture disk and sliding door of the capsule can be controlled and the interval between opening and closing controlled. The wiring or control would be preferably controlled though the robot arm or could be wirelessly controlled. An independent source of electrical power could provided through the robot arm or distinct from it, including from a battery in the capsule. A so-called raspberry pi can be programmed to control the stepper motors.

A computer via software will control the stepper motors electrically through standard computer interface ports, such as a USB, USB2, serial port, parallel port or other well defined standard interface as identified by the IEEE or other international standards organizations. The computer software will be designed and built to provide layered approach to communications with the software and hardware operating in concert, using a simple loop control approach, an interrupt driven approach, or a monolithic software kernel or some combination of these. The software interfaces with device drivers which translate high level software instructions into stepper motor motion and repetition instructions at the hardware device level. These hardware instructions will then command stepping motor controller interfaces which will generate stepping motor holding currents and stepping motor pulses to cause the stepping motors to move in the desired direction or to hold the shutters in a desired position. Power for the interfaces and associated hardware circuits will come from an isolated power supply, and motor winding power will be provided from a stepper motor DC power supply applied and controlled by the stepper motor controller as programmed by the software. The power supply selected was from Lin Engineering of 16245 Vineyard Blvd., Morgan Hill, California 95037, part number PW-100-24, but suitable power supplies are readily available and other parts can be found from general electronic and small parts manufacturers and distributors.

This design maintains good radiation shielding from all directions.

Also contemplated are a fiber optic camera, and a light source to illuminate tissue. They can be disposed in a variety of positions adjacent to the front mount opening in the front mount which opening is alternately occluded by the slide door.

Also contemplated is a circuit to operate an indicator light to verify if the slide door is open or closed.

Also contemplated are two line lasers that will form a cross showing the center target spot of the radiation emission when the door and disk expose the target tissue. This will allow the operator viewing through the camera to see where the capsule is pointing.

A positioning device such as a range finder or ultrasound device is contemplated.

Also contemplated is that if power is lost to the capsule, the electromechanical connection to the capsule would become flexible so that the robot arm, or instrument, can be used to extract the capsule through the incision or orifice through which the capsule was inserted.

Figure 10:
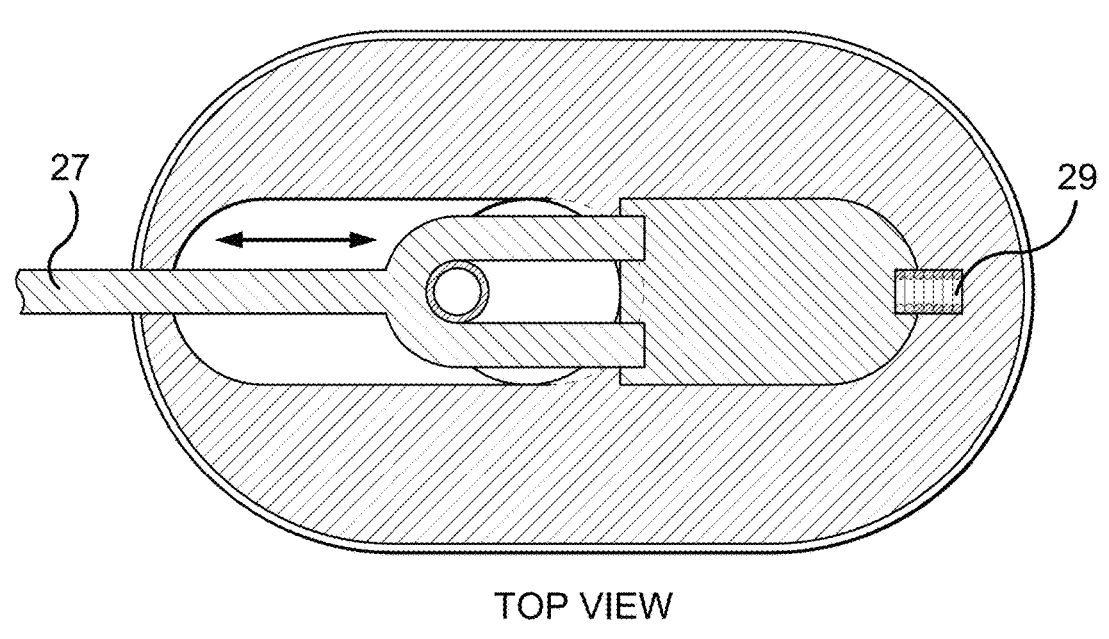
FIG. 10 is a top view of FIG. 9.

Turning to specifics of further design of the shutter mechanism, FIG. 9 shows a simplified picture of the principle of a shutter mechanism. A push rod (27), operated from a surgical robot arm is designed to operate the shutter (31). The push rod is best used moving interior to a sleeve (28) of the robotic arm, shown in FIG. 12. The push rod, or the shutter it is pushing or both, can work against one or more springs (14) that is (are) compressed when the shutter is open (29), seated in an aperture in the capsule (9). The spring gives a fail-safe mechanism to close the shutter if power is lost. The movement of the shutter can alternately open or occlude the radioisotope from emitting radiation out from the shutter through the emission aperture (30) which will be adjacent to the tumor being irradiated. In FIG. 10, a cross section, the push rod (27) has a U-shape surrounding the conical round aperture (30) and preferably shaped to line up with the cone of radiation. A stop (32) for the U-shape is shown, but is not required. FIG. 11 shows a simplified view without all the internal mechanism. FIG. 12 shows another design for the shape of the shutter (33). The distance AB can be optimized so that the combination of radiation occlusion from the sum of the void and the distance through the capsule (9) can be made close to equal to the sum of the void on the opposite side of the aperture cone, plus the distance CD plus the small amount of the capsule to secure the shutter. Because it is difficult to work, if additional shielding is desired, tungsten blocks or tungsten shells can be inserted in the capsule before it is assembled. A proposed location for a tungsten shell plate (34) covering some or most of the capsule, in this case shown as a flat panel, can be seen at the top of FIG. 13.

Yet another design is shown in FIGS. 14, 15 and 13. The radioisotope is numbered (35). A desired cone of radiation from the isotope to an emission aperture (30) is shown. Adjacent to, but not jutting into that cone of radiation when open, is a series of plates. They can all be operated from one side by a push rod (27), or be operated synchronously by levers or a gear mechanism from one or both sides. A push road can operate on the one or more levers to operate the shutters simultaneously from an open position to a closed position and vice versa. The one or more levers simply have to be positioned within the capsule to move the moving plate

(37) the necessary distance from the open to closed position with the lever set so that upon the movement of that necessary distance, the motion of the lever is increased to act to close by the distance necessary to move a more outwardly plate (41) to its closed position and likewise with a linkage to close moving plate 45 from the open position to its closed position covering the cone of radiation. The push rod is shown interior to a push rod sleeve. The plates preferably alternate as follows. They can be referred to as multiple moving plates to moving plate receptacles. If from opposite sides, they are interleaving moving plates to moving plate receptacles. The first moving plate (37) is closest to the radioisotope for this illustration. It can be rounded to correspond to a first moving plate receiving aperture. (36). The first moving plate receptacle simply needs to correspond to the shape of the end of the opposite first moving plate (37) which will move toward it when it closes, but when the shutter is open, neither should infringe on the desired cone of radiation to the aperture (30) to avoid unnecessary penumbra. The first moving plate (37), as with all the moving plates to be described, can be designed to work against a spring in the same vein as in FIG. 10 (spring not shown). A lever mechanism forcing the shutter closed can be used so only when the push rod is operated does the shutter open. This is intended to be a fail-safe mechanism. A small groove (38) is set in the first moving plate and the top of the first moving late receptacle to guide the next second moving plate (39). This is shown in FIGS. 14 and 15. It moves into a second moving plate receptacle (40). The shape of the end of the second moving plate (39) can be rounded, or can be geometrically similar to the shape of the first moving plate receptacle (36). The idea is that each plate in a sense has an opposite fitting characteristic to the underlying plate to better assure no leakage and to accomplish occlusion of radioactivity as much as possible when the shutter composed of the moving plates is closed. In this figure, the first and second moving plates are designed to move together, but they need not be joined, and the moving plates can be set so as to move from left to the right of the drawing, or alternately with the first moving plate moving from left to right and then the second moving plate moving from right to left. In the same vein with similar shapes, three more plates are shown, a third moving plate (41) which moves to a third moving plate receptacle (42), and a fourth moving plate (43) moving to a fourth moving plate receptacle (44). The third and fourth moving plates here are designed to work together and another groove is shown in the top of the fourth moving plate. There can be a groove (38) in each plate with a tongue (47) from the upper plate fitting into the groove. Finally, a fifth moving plate (45) into a fifth moving plate receptacle (46) is shown. FIG. 13 shows the push rod 27. A tungsten shell plate as in number 34 in FIG. 13 can be utilized.

Where the tungsten shell plate is to be located can be a cavity surrounding some, most or all of the capsule which can be sealable, and other materials such as lead, depleted uranium, tungsten as mentioned, or other highly radioactive absorbent materials which are either sometimes toxic or very difficult to melt or work can be inserted in such a cavity.

The embodiments represented herein are only a few of the many embodiments and modifications that a practitioner reasonably skilled in the art could make or use. The invention is not limited to these embodiments. Alternative embodiments and modifications which would still be encompassed by the invention may be made by those skilled in the art, particularly in light of the foregoing teachings. Therefore, the following claims are intended to cover any alternative embodiments, modifications or equivalents which may be included within the spirit and scope of the invention as claimed.

We claim:

1. A surgical robotic intra-operative radiation therapy device having at least one cylindrical rotating shutter defining, in conjunction with a capsule, a defined conical beam of radiation comprising:

a robotic device configured for surgical use having at least one robotic arm configured to be manipulated remotely;

for a patient having a surgical incision, an interchangeable capsule for irradiating at least one patient tissue by a desired width of radiation beam exposure, said capsule for irradiating said at least one tissue and said incision being sized for said capsule to be insertable through said surgical incision;

said capsule having a longitudinal central capsule axis and having an emission aperture opening which opens to an emission cavity internal to said capsule, said capsule having at least one cylindrical rotating shutter rotating on said central capsule axis for alternately occluding and uncovering said aperture opening to said emission cavity;

each said at least one cylindrical rotating shutter having an electromechanical means of rotating each of said at least one cylindrical rotating shutters;

said capsule having shielding selected to attenuate radiation exterior to said capsule;

said capsule having a remotely operable means for controlling at least one of said at least one cylindrical rotating shutters;

a first of said at least one cylindrical rotating shutters having a circular conical aperture conforming to a desired width of radiation beam exposure with an apex of said circular conical aperture being centered on a radiation source centered in said cylindrical rotating shutter, said circular conical aperture of said at least one cylindrical rotating shutter conforming to a defined cone, said defined cone being calculated by the selected distance of said desired width of radiation beam exposure beam from the radiation source through the capsule to the patient tissue;

each at least one succeeding cylindrical shutter from said first of said at least one cylindrical rotating shutters set outwardly from said capsule center axis having a conical aperture conforming to said defined cone, and the series of said at least one cylindrical rotating shutters in combination with said emission aperture opening conforming to said defined cone in a manner that based on each conical aperture of all of said at least one cylindrical rotating shutters being aligned a smooth cone of radiation without penumbra internal to the capsule is formed from the radiation source to the exterior edge of the capsule and configured for projecting the desired width of radiation beam exposure on the patient tissue;

said remotely operable means for controlling each said shutter cooperating with at least one electromechanical means of rotating each of said at least one cylindrical rotating shutters to align all of said at least one cylindrical rotating shutters with said emission aperture opening;

said robotic arm having a first means for robotic arm electrical communication and control;

said device having a shuttle capsule holder mountable on said robotic arm, said shuttle capsule holder having a second means for electrical communication and control compatible for purposes of interchangeability with said capsule;

said capsule being mountable on said shuttle capsule holder;

said shuttle capsule holder having a third means for electrical communication and control compatible for purposes of interchangeability with said first means for robotic arm electrical communication and control;

a means for positive attachment between said robotic arm and said shuttle capsule holder, said means for positive attachment being compatible for purposes of interchangeability with said shuttle capsule holder and said first and second means for electrical communication and control;

said capsule having a means for closing said at least one cylindrical rotating shutters to a fail-safe closed position shielding the patient tissue from a direct line through at least one of said cylindrical rotating shutters to the radiation source based on whether power is lost to said capsule;

a general purpose computer for transmitting data to and from said capsule; and said intraoperative therapy device having said at least one robot arm configured to be manipulated remotely cooperating with said capsule to move said aperture of said capsule adjacent to patient tissue to be irradiated, in a manner that by operating said at least one electromechanical means of rotating, all of said at least one cylindrical rotating shutters are aligned to expose said patient tissue to said radiation source disposed within said capsule.

2. The surgical robotic intra-operative radiation therapy device according to claim 1, further comprising:

a means for utilizing ultrasonic detection to determine tissue depth, including tumor depth to determine an applicable margin to be irradiated.

3. The surgical robotic intra-operative radiation therapy device according to claim 1, further comprising:

a selected radiation source disposed in said capsule appropriate to irradiate said tissue through said aperture;

said capsule being selected to attenuate radiation based on its shielding characteristic for said selected radiation source to minimize excess doses of radiation to said patient while said shutter is in said closed position for the time period said capsule is proposed to be inside said patient.

4. The surgical robotic intra-operative radiation therapy device according to claim 1, further comprising:

a shroud to narrow a beam of radiation emanating from said capsule through said shutter.

5. The surgical robotic intra-operative radiation therapy device according to claim 2, further comprising:

said capsule having an adjustable aperture size.

6. The surgical robotic intra-operative radiation therapy device according to claim 1, further comprising:

said capsule having a removable cap;

said removable cap having a protrusion fitting within the interior diameter of said first of said cylindrical rotating shutters on which a radioactive source is mounted;

said protrusion being of a length that with said removable cap mounted on said capsule, said radiation source is positioned at said apex of said circular conical aperture interior to said capsule.

7. The surgical robotic intra-operative radiation therapy device according to claim 1, further comprising:

a means for mapping physiologic activity detectable by non-visual spectrum.

8. The surgical robotic intra-operative radiation therapy device according to claim 1, further comprising:

at least one means for direct visualization by remote means of tissue adjacent to said capsule to ascertain whether all diseased tissue has been surgically removed and to ascertain whether further irradiation is necessary.

9. The surgical robotic intra-operative radiation therapy device according to claim 1, further comprising:

an interchangeable cartridge fitting into a capsule cartridge aperture in said capsule to dispose said radiation source in said capsule interior to said emission aperture.

10. The surgical robotic intra-operative radiation therapy device according to claim 1, further comprising:

said means for positive attachment being potentially rendered flexible if based on whether power is lost to said capsule.

11. The surgical robotic intra-operative radiation therapy device according to claim 1, further comprising:

a pointer for ascertaining the relative position of said surgical robotic intra-operative therapy device relative to patient tissue to be irradiated.

12. The surgical robotic intra-operative radiation therapy device according to claim 1, further comprising:

a means for stand-off remote determination of the distance from the radiation source to the tissue being irradiated.

13. The surgical robotic intra-operative radiation therapy device according to claim 1, further comprising:

a speech interface subject to manual override to enable voice recognition of an operator of said device to assist in direction of said capsule on pre-defined axes, said speech interface being integrated with said general purpose computer.

14. The surgical robotic intra-operative radiation therapy device according to claim 1, further comprising:

said electromechanical means of rotating each of said at least one cylindrical rotating shutters having at least one cam;

said at least one cam on each said cylindrical rotating shutter being configured for cooperating with said means for closing said at least one cylindrical rotating shutters to a fail-safe closed position in a manner that each said aperture on said cylindrical shell and said capsule are aligned at a rotational angle offset from the rotational angle of any other aperture while said surgical robotic intra-operative radiation therapy device is not operating.

15. The surgical robotic intra-operative radiation therapy device according to claim 1, further comprising:

said electromechanical means or rotating each of said at least one cylindrical rotating shutters having a gear.

16. The surgical robotic intra-operative radiation therapy device according to claim 1, further comprising:

said means for closing said at least one cylindrical rotating shutters to a fail-safe closed position having a spring to shield the patient tissue from a direct line through each said conical aperture to the radiation source if based on whether power is lost to said capsule.

17. The surgical robotic intra-operative radiation therapy device according to claim 16, further comprising:

said means for closing said at least one cylindrical rotating shutters to a fail-safe closed position to shield the patient tissue from a direct line through each said conical aperture to the radiation source based on whether power is lost to said capsule having a lever operating on a pivot disposed between said spring and said shutter with said lever having a longer end juxtaposed to said shutter and a shorter end juxtaposed to said spring to minimize the travel of said spring.

18. The surgical robotic intra-operative radiation therapy device according to claim 16, further comprising:

said means for closing said at least one cylindrical rotating shutters to a fail-safe closed position to shield the patient tissue from a direct line through each said conical aperture to the radiation source if based on whether power is lost to said capsule having a linear actuator with an operating position to secure at least one said shutter after a stepper motor to operate said shutters is operated and said stepper motor is turned off while said capsule is receiving power from said robotic arm and said linear actuator having a closed position which releases said shutter based on said capsule or said linear actuator not receiving power from said at least one robotic arm.

19. A surgical robotic intra-operative radiation therapy device having at least one cylindrical rotating shutter defining, in conjunction with a capsule, a defined conical beam of radiation oriented through the end of said capsule comprising:

a robotic device configured for surgical use having at least one robotic arm configured to be manipulated remotely;

for a patient having a surgical incision, an interchangeable capsule for irradiating at least one patient tissue by a desired width of radiation beam exposure, said capsule for irradiating said at least one tissue and said incision being sized for said capsule to be insertable through said surgical incision;

said capsule having a longitudinal central capsule axis and having an emission aperture opening at the end of said capsule which opens to an emission cavity internal to said capsule, said capsule having at least one cylindrical rotating shutter rotating perpendicular to said central capsule axis for alternately occluding and uncovering said aperture opening to said emission cavity;

each said at least one cylindrical rotating shutter having an electromechanical means of rotating each of said at least one cylindrical rotating shutters;

said capsule having shielding selected to attenuate radiation exterior to said capsule;

said capsule having a remotely operable means for controlling at least one of said at least one cylindrical rotating shutters;

a first of said at least one cylindrical rotating shutters having a circular conical aperture conforming to a desired width of radiation beam exposure with an apex of said circular conical aperture being centered on a radiation source centered in said cylindrical rotating shutter, said circular conical aperture of said at least one cylindrical rotating shutter conforming to a defined cone, said defined cone being calculated by the selected distance of said desired width of radiation beam exposure beam from the radiation source through the capsule to the patient tissue;

each at least one succeeding cylindrical shutter from said first of said at least one cylindrical rotating shutters set outwardly from and perpendicular to said capsule center axis having a conical aperture conforming to said defined cone, and the series of said at least one cylindrical rotating shutters in combination with said emission aperture opening conforming to said defined cone in a manner that based on each conical aperture of all of said at least one cylindrical rotating shutters being aligned a smooth cone of radiation without penumbra internal to the capsule is formed from the radiation source to the exterior edge of the capsule and configured for projecting the desired width of radiation beam exposure on the patient tissue;

said remotely operable means for controlling each said shutter cooperating with at least one electromechanical means of rotating each of said at least one cylindrical rotating shutters to align all of said at least one cylindrical rotating shutters with said emission aperture opening;

said robotic arm having a first means for robotic arm electrical communication and control;

said device having a shuttle capsule holder mountable on said robotic arm, said shuttle capsule holder having a second means for electrical communication and control compatible for purposes of interchangeability with said capsule;

said capsule being mountable on said shuttle capsule holder;

said shuttle capsule holder having a third means for electrical communication and control compatible for purposes of interchangeability with said first means for robotic arm electrical communication and control;

a means for positive attachment between said robotic arm and said shuttle capsule holder, said means for positive attachment being compatible for purposes of interchangeability with said shuttle capsule holder and said first and second means for electrical communication and control;

said capsule having means for closing said at least one cylindrical rotating shutters to a fail-safe closed position shielding the patient tissue from a direct line through at least one of said cylindrical rotating shutters to the radiation source based on whether power is lost to said capsule;

a general purpose computer for transmitting data to and from said capsule; and said intraoperative therapy device having at least one robot arm configured to be operated remotely cooperating with said capsule to move said aperture of said capsule adjacent to patient tissue to be irradiated, in a manner that by operating said at least one electromechanical means of rotating, all of said at least one cylindrical rotating shutters are aligned to expose said patient tissue to said radiation source disposed within said capsule.

20. The surgical robotic intra-operative radiation therapy device according to claim 19, further comprising:
a means for utilizing ultrasonic detection to determine tissue depth, including tumor depth to determine an applicable margin to be irradiated.

21. The surgical robotic intra-operative radiation therapy device according to claim 19, further comprising:
a selected radiation source disposed in said capsule appropriate to irradiate said tissue through said aperture;
said capsule being selected to attenuate radiation based on its shielding characteristic for said selected radiation source to minimize excess doses of radiation to said patient while said shutter is in said closed position for the time period said capsule is proposed to be inside said patient.

22. The surgical robotic intra-operative radiation therapy device according to claim 21, further comprising:
a shroud to narrow a beam of radiation emanating from said capsule through said shutter.

23. The surgical robotic intra-operative radiation therapy device according to claim 21, further comprising:
said capsule having an adjustable aperture size.

24. The surgical robotic intra-operative radiation therapy device according to claim 19, further comprising:
said capsule having a removable cap;
said removable cap having a protrusion fitting within the interior diameter of said first of said cylindrical rotating shutters on which a radioactive source is mounted;
said protrusion being of a length that with said removable cap mounted on said capsule, said radiation source is positioned at said apex of said circular conical aperture interior to said capsule.

25. The surgical robotic intra-operative radiation therapy device according to claim 19, further comprising:
a means for mapping physiologic activity detectable by non-visual spectrum.

26. The surgical robotic intra-operative radiation therapy device according to claim 19, further comprising:
at least one means for direct visualization by remote means of tissue adjacent to said capsule to ascertain whether all diseased tissue has been surgically removed and to ascertain whether further irradiation is necessary.

27. The surgical robotic intra-operative radiation therapy device according to claim 19, further comprising:
an interchangeable cartridge fitting into a capsule cartridge aperture in said capsule to dispose said radiation source in said capsule interior to said emission aperture.

28. The surgical robotic intra-operative radiation therapy device according to claim 19, further comprising:
said means for positive attachment being potentially rendered flexible based on whether power is lost to said capsule.

29. The surgical robotic intra-operative radiation therapy device according to claim 19, further comprising:
a pointer for ascertaining the relative position of said surgical robotic intra-operative therapy device relative to patient tissue to be irradiated.

30. The surgical robotic intra-operative radiation therapy device according to claim 19, further comprising:
a means for stand-off remote determination of the distance from the radiation source to the tissue being irradiated.

31. The surgical robotic intra-operative radiation therapy device according to claim 19, further comprising:
a speech interface subject to manual override to enable voice recognition of an operator of said device to assist in direction of said capsule on pre-defined axes, said speech interface being integrated with said general purpose computer.

32. The surgical robotic intra-operative radiation therapy device according to claim 19, further comprising:
said electromechanical means of rotating each of said at least one cylindrical rotating shutters having at least one cam;
said at least one cam on each said cylindrical rotating shutter being configured for cooperating with said means for closing said at least one cylindrical rotating shutters to a fail-safe closed position in a manner that each said aperture on said cylindrical rotating shutter and said capsule are aligned at a rotational angle offset from the rotational angle of any other aperture while said surgical robotic intra-operative radiation therapy device is not operating.

33. The surgical robotic intra-operative radiation therapy device according to claim 19, further comprising:

said electromechanical means or rotating each of said at least one cylindrical rotating shutters having a gear.

34. The surgical robotic intra-operative radiation therapy device according to claim 19, further comprising:

said means for closing said at least one cylindrical rotating shutters to a fail-safe closed position having a spring to shield the patient tissue from a direct line through each said conical aperture to the radiation source based on whether power is lost to said capsule.

35. The surgical robotic intra-operative radiation therapy device according to claim 34, further comprising:

said means for closing said at least one cylindrical rotating shutters to a fail-safe closed position to shield the patient tissue from a direct line through each said conical aperture to the radiation source based on whether power is lost to said capsule having a lever operating on a pivot disposed between said spring and said shutter with said lever having a longer end juxtaposed to said shutter and a shorter end juxtaposed to said spring to minimize the travel of said spring.

36. The surgical robotic intra-operative radiation therapy device according to claim 34, further comprising:

said means for closing said at least one cylindrical rotating shutters to a fail-safe closed position to shield the patient tissue from a direct line through said apertures to the radiation source based on whether power is lost to said capsule having a linear actuator with an operating position to secure at least one said shutter after a stepper motor to operate said shutters is operated and said stepper motor is turned off while said capsule is receiving power from said robotic arm and said linear actuator having a closed position which releases said shutter based on said capsule or said linear actuator not receiving power from said at least one robotic arm.

37. A surgical robotic intra-operative radiation therapy device having at least one cylindrical rotating shutter defining in conjunction with a capsule a defined conical beam of radiation comprising:

a robotic device configured for surgical use having at least one robotic arm configured to be manipulated remotely;

for a patient having a surgical incision, an interchangeable capsule for irradiating at least one patient tissue by a desired width of radiation beam exposure, said capsule for irradiating said at least one tissue and said incision being sized for said capsule to be insertable through said surgical incision;

said capsule having a longitudinal central capsule axis and having an emission aperture opening which opens to an emission cavity internal to said capsule, said capsule having at least one cylindrical rotating shutter rotating on said central capsule axis for alternately occluding and uncovering said aperture opening to said emission cavity;

each said at least one cylindrical rotating shutter having an electromechanical means of rotating each of said at least one cylindrical rotating shutters;

said capsule having shielding selected to attenuate radiation exterior to said capsule;

said capsule having a remotely operable means for controlling at least one of said at least one cylindrical rotating shutters;

a first of said at least one cylindrical rotating shutters having a circular conical aperture conforming to a desired width of radiation beam exposure with an apex of said circular conical aperture being centered on a radiation source centered in said cylindrical rotating shutter, said circular conical aperture of said at least one cylindrical rotating shutter conforming to a defined cone, said defined cone being calculated by the selected distance of said desired width of radiation beam exposure beam from the radiation source through the capsule to the patient tissue;

each at least one succeeding cylindrical shutter from said first of said at least one cylindrical rotating shutters set outwardly from said capsule center axis having a conical aperture conforming to said defined cone, and the series of said at least one cylindrical rotating shutters in combination with said emission aperture opening conforming to said defined cone in a manner that based on each conical aperture of all of said at least one cylindrical rotating shutters being aligned, a smooth cone of radiation without penumbra internal to the capsule is formed from the radiation source to the exterior edge of the capsule and configured for projecting the desired width of radiation beam exposure on the patient tissue;

said remotely operable means for controlling each said shutter cooperating with at least one electromechanical means of rotating each of said at least one cylindrical rotating shutters to align all of said at least one cylindrical rotating shutters with said emission aperture opening;

said robotic arm having a first means for robotic arm electrical communication and control;

said device having a shuttle capsule holder mountable on said robotic arm, said shuttle capsule holder having a second means for electrical communication and control compatible for purposes of interchangeability with said capsule;

said capsule being mountable on said shuttle capsule holder;

said shuttle capsule holder having a third means for electrical communication and control compatible for purposes of interchangeability with said first means for robotic arm electrical communication and control;

a means for positive attachment between said robotic arm and said shuttle capsule holder, said means for positive attachment being compatible for purposes of interchangeability with said shuttle capsule holder and said first and second means for electrical communication and control;

said capsule having a means for closing said at least one cylindrical rotating shutters to a fail-safe closed position shielding the patient tissue from a direct line through at least one of said cylindrical rotating shutters to the radiation source based on whether power is lost to said capsule;

at least one means for direct visualization by remote means of tissue adjacent to said capsule to ascertain whether all diseased tissue has been surgically removed and to ascertain whether further irradiation is necessary;

a means for stand-off remote determination of the distance from the radiation source to the tissue being irradiated;

a laser pointer;

a general purpose computer for transmitting data to and from said capsule; and said intraoperative therapy device having at least one remotely manipulatable robot arm cooperating with said capsule to move said aperture of said capsule adjacent to patient tissue to be irradiated, in a manner that by operating said at least one electromechanical means of rotating, all of said at least one cylindrical rotating shutters are aligned to expose said patient tissue to said radiation source disposed within said capsule.

38. The surgical robotic intra-operative radiation therapy device according to claim 37, further comprising:

said capsule having a removable cap;

said removable cap having a protrusion fitting within the interior diameter of said first of said cylindrical rotating shutters on which a radioactive source is mounted;

said protrusion being of a length that with said removable cap mounted on said capsule, said radiation source is positioned at said apex of said circular conical aperture interior to said capsule.

39. The surgical robotic intra-operative radiation therapy device according to claim 37, further comprising:

a means for mapping physiologic activity detectable by non-visual spectrum.

40. The surgical robotic intra-operative radiation therapy device according to claim 37, further comprising:

said means for positive attachment being potentially rendered flexible based on whether power is lost to said capsule.

\* \* \* \* \*